United States Patent
Cate et al.

(10) Patent No.: US 9,670,515 B2
(45) Date of Patent: Jun. 6, 2017

(54) METHODS FOR PRODUCTION OF XYLOSYLXYLITOL OLIGOMERS

(71) Applicant: The Regents of the University of California, Oakland, CA (US)

(72) Inventors: James H. Doudna Cate, Berkeley, CA (US); Xin Li, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/379,453

(22) Filed: Dec. 14, 2016

(65) Prior Publication Data

US 2017/0096693 A1   Apr. 6, 2017

Related U.S. Application Data

(63) Continuation of application No. PCT/US2015/037115, filed on Jun. 23, 2015.

(60) Provisional application No. 62/016,555, filed on Jun. 24, 2014.

(51) Int. Cl.
| | |
|---|---|
| *C12P 19/04* | (2006.01) |
| *C12P 19/12* | (2006.01) |
| *C12N 9/02* | (2006.01) |
| *C12N 15/81* | (2006.01) |
| *C07K 14/37* | (2006.01) |

(52) U.S. Cl.
CPC ............ *C12P 19/12* (2013.01); *C07K 14/37* (2013.01); *C12N 9/0004* (2013.01); *C12N 15/81* (2013.01); *C12N 15/815* (2013.01)

(58) Field of Classification Search
None
See application file for complete search history.

(56) References Cited

FOREIGN PATENT DOCUMENTS

| UY | WO 2011011796 A2 * | 1/2011 | ............ C07K 14/37 |
|---|---|---|---|
| WO | WO 2013059326 A1 * | 4/2013 | ................ C12P 7/18 |

OTHER PUBLICATIONS

Galazka et al., "Improving the bioconversion of plant biomass to biofuels: A multidisciplinary approach", Energy Environ. Sci. 4:3329-3333, 2011.*
Frankova et al: "Trans-alpha-xylosidase, a widespread enzyme activity in plants, introduces (1 >4)-alpha D-xylobiose side-chains into xyloglucan structures ", Phytochemistry, vol. 78, 2812, pp. 29 43, XP882743289, See p. 33 (Figure 3b), p. 35 (left column , and p. 36 (Figure 6b) 2012.
Pena et al: Arabidopsis irregular xylems and irregular xylem9: Implications for the complexity of glucuronoxylan biosynthesis, The Plant Cell, vol. 19, 2887, pp. 549-563, XP882589991, * See p. 559 (Table 5) * 2007.
Znameroski et al: Evidence for transceptor function of cellodextrin transporters in Neurospora crassa, The Journal of Biological Chemistry, vol. 289, Jan. 31, 2014 (Jan. 31, 2014), pp. 2610-2619, XP002743326, See p. 2617 (Figure 7)
Cai et al: Evidence of a critical role for cellodextrin transporter 2 (CDT-2) in both cellulose and hemicellulose degradation and utilization in Neurospora crassa, PLOS ONE, vol. 9, E89330, Feb. 2014 (Feb. 2014), pp. 1-10, XP002743296, cited in the application * See p. 1 (Abstract) and p. 8 (Discussion)
Kim et al: Analysis of cellodextrin transporters from Neurospora crassa in *Saccharomyces cerevisiae* for cellobiose fermentation, Applied Microbiology and Biotechnology, vol. 98, Nov. 5, 2013 (Nov. 5, 2013), pp. 1087-1094, XP035328524, *See p. 1087 (Abstract); early online publication.
Chomvong et al: Overcoming inefficient cellobiose fermentation by cellobiose phosphorylase in the presence of kylose, Biotechnology for Biofuels, vol. 7, Jun. 7, 2014 (Jun. 7, 2014), pp. 1-11, XP021188566, * See p. 7 (Figure 6) *.
Galazka et al: Cellodextrin transport in yeast for improved biofuel production, Science, vol. 330, 2010, pp. 84-86, XP002673429, cited in the application * See Figures 1-3.
Li et al: 11 Expanding xylose metabolism in yeast for plant cell wall conversion to biofuels 11, Elife, vol. 4, E05896, Feb. 3, 2015 (Feb. 3, 2015), pp. 1-16, XP002743290, *Publication of the invention; earlier online disclosure on Aug. 9, 2014.

* cited by examiner

*Primary Examiner* — David J Steadman
(74) *Attorney, Agent, or Firm* — Richard Aron Osman

(57) ABSTRACT

The present disclosure relates generally to the production of xylosyl-xylitol oligomers, and more specifically to biological methods for producing xylosyl-xylitol oligomers in host cells.

19 Claims, 33 Drawing Sheets
(30 of 33 Drawing Sheet(s) Filed in Color)

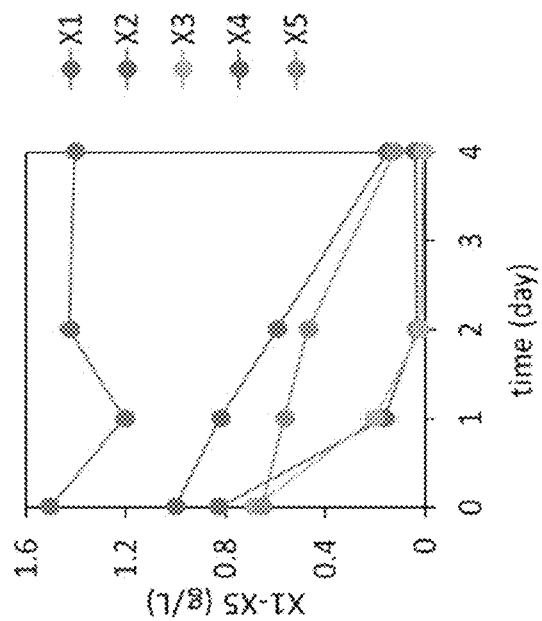
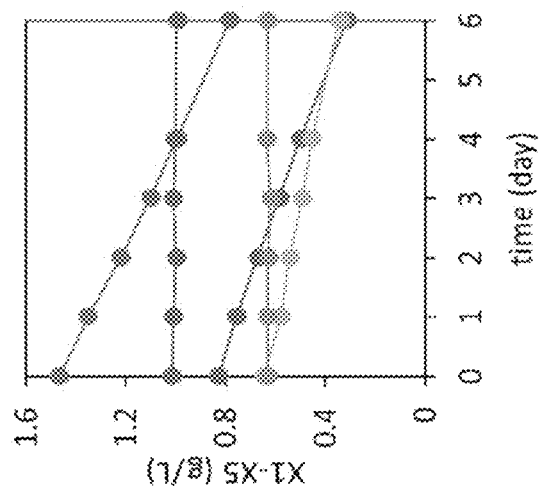
Fig. 2A
Fig. 2B

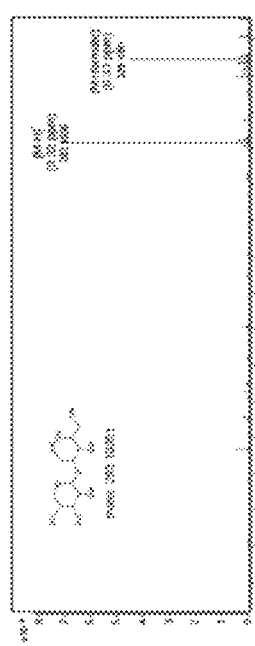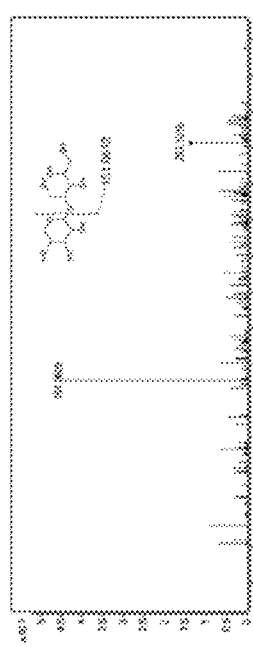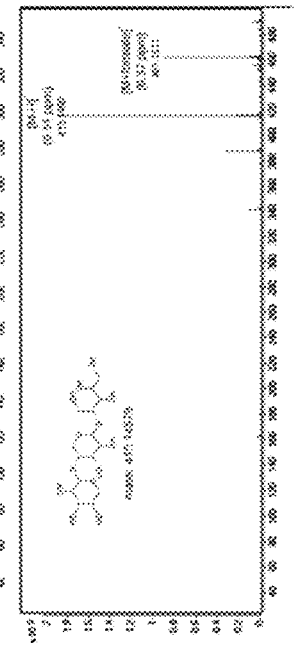
Fig. 4A
Fig. 4B

| Gene# | Glucose | No Carbon | Avicel | Xylan |
|---|---|---|---|---|
| NCU00801(CDT-1) | 4.8 | 86.3 | | 54.8 |
| NCU08114(CDT-2) | 0.6 | 96.9 | | |
| NCU05853(CBT-1)* | 1.4 | 328.5 | | 358.2 |
| NCU06138 | 0.5 | 22.5 | 563.8 | 871.5 |
| NCU01231 | 0.4 | 463.2 | 286.1 | 725.1 |
| NCU10021 | 3.7 | 494.8 | 783.6 | |
| NCU05897 | 0.6 | 371.4 | 730.7 | |
| NCU04963 | 1.7 | 269.2 | 402.7 | 1356.3 |
| NCU05585 | 0.8 | 227.8 | 66.2 | 52.1 |
| NCU01132 | 0.1 | 48.3 | 25.3 | 177.6 |
| NCU00988 | 0.1 | 217.7 | 197.2 | 430.1 | transcription level (FPKM)

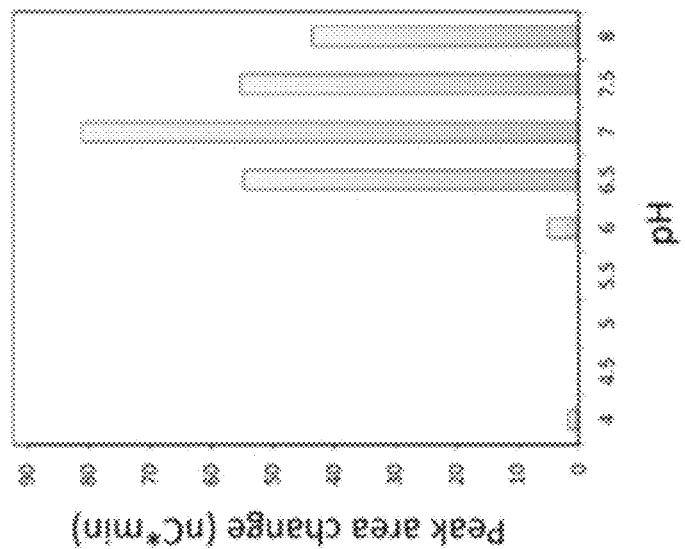
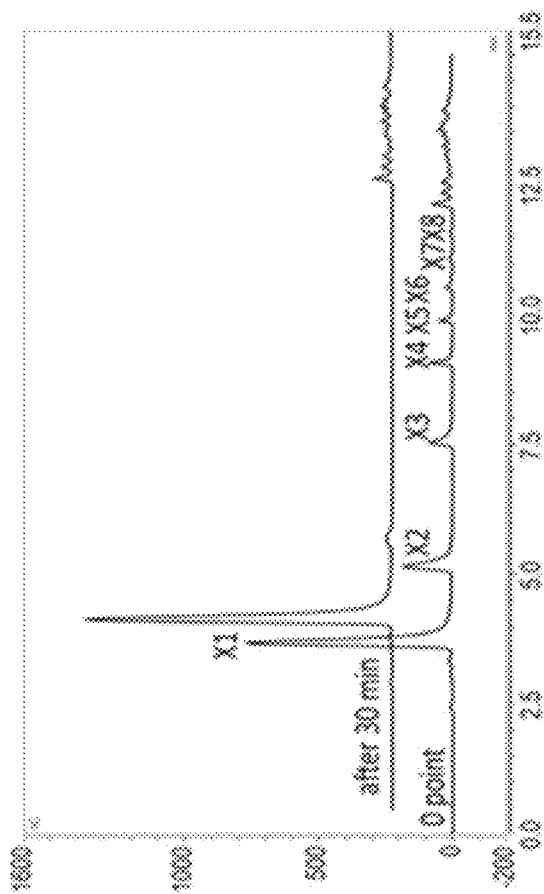
Fig. 20A
Fig. 20B

SEQUENCE LISTING

```
<160> NUMBER OF SEQ ID NOS: 12

<210> SEQ ID NO 1
<211> LENGTH: 525
<212> TYPE: PRT
<213> ORGANISM: N. crassa

<400> SEQUENCE: 1

Met Gly Ile Phe Asn Lys Lys Pro Val Ala Gln Ala Val Asp Leu Asn
  1               5                  10                  15

Gln Ile Gln Glu Glu Ala Pro Gln Phe Glu Arg Val Asp Trp Lys Lys
             20                  25                  30

Asp Pro Gly Leu Arg Lys Leu Tyr Phe Tyr Ala Phe Ile Leu Cys Ile
         35                  40                  45

Ala Ser Ala Thr Thr Gly Tyr Asp Gly Met Phe Phe Asn Ser Val Gln
     50                  55                  60

Asn Phe Glu Thr Trp Ile Lys Tyr Phe Gly Asp Pro Arg Gly Ser Glu
 65                  70                  75                  80

Leu Gly Leu Leu Gly Ala Leu Tyr Gln Ile Gly Ser Ile Gly Ser Ile
                 85                  90                  95

Pro Phe Val Pro Leu Leu Thr Asp Asn Phe Gly Arg Lys Thr Pro Ile
            100                 105                 110

Ile Ile Gly Cys Val Ile Met Ile Val Gly Ala Val Leu Gln Ala Thr
        115                 120                 125

Ala Lys Asn Leu Asp Thr Phe Met Gly Gly Arg Thr Met Leu Gly Phe
    130                 135                 140

Gly Asn Ser Leu Ala Gln Ile Ala Ser Pro Met Leu Leu Thr Glu Leu
145                 150                 155                 160

Ala His Pro Gln His Arg Ala Arg Leu Thr Thr Ile Tyr Asn Cys Leu
                165                 170                 175

Trp Asn Val Gly Ala Leu Val Val Ser Trp Leu Ala Phe Gly Thr Asn
            180                 185                 190

Tyr Ile Asn Asn Asp Trp Ser Trp Arg Ile Pro Ala Leu Leu Gln Ala
        195                 200                 205

Phe Pro Ser Ile Ile Gln Leu Leu Gly Ile Trp Trp Val Pro Glu Ser
    210                 215                 220

Pro Arg Phe Leu Ile Ala Lys Asp Lys His Asp Glu Ala Leu His Ile
225                 230                 235                 240

Leu Ala Lys Tyr His Ala Asn Gly Asp Pro Asn His Pro Thr Val Gln
                245                 250                 255

Phe Glu Phe Arg Glu Ile Lys Glu Thr Ile Arg Leu Glu Met Glu Ser
            260                 265                 270

Thr Lys Asn Ser Ser Tyr Leu Asp Phe Phe Lys Ser Arg Gly Asn Arg
        275                 280                 285

Tyr Arg Leu Ala Ile Leu Leu Ser Leu Gly Phe Phe Ser Gln Trp Ser
    290                 295                 300

Gly Asn Ala Ile Ile Ser Asn Tyr Ser Ser Lys Leu Tyr Glu Thr Ala
305                 310                 315                 320

Gly Val Thr Asp Ser Thr Ala Lys Leu Gly Leu Ser Ala Gly Gln Thr
```

```
                    325                 330                 335
Gly Leu Ala Leu Ile Val Ser Val Thr Met Ala Leu Leu Val Asp Lys
                340                 345                 350

Leu Gly Arg Arg Leu Ala Phe Leu Ala Ser Thr Gly Met Cys Gly
            355                 360                 365

Thr Phe Val Ile Trp Thr Leu Thr Ala Gly Leu Tyr Gly Glu His Arg
370                 375                 380

Leu Lys Gly Ala Asp Lys Ala Met Ile Phe Phe Ile Trp Val Phe Gly
385                 390                 395                 400

Ile Phe Tyr Ser Leu Ala Trp Ser Gly Leu Leu Val Gly Tyr Ala Ile
                405                 410                 415

Glu Ile Leu Pro Tyr Arg Leu Arg Gly Lys Gly Leu Met Val Met Asn
                420                 425                 430

Met Ser Val Gln Cys Ala Leu Thr Leu Asn Thr Tyr Ala Asn Pro Val
                435                 440                 445

Ala Phe Asp Tyr Phe Gly Pro Asp His Ser Trp Lys Leu Tyr Leu Ile
            450                 455                 460

Tyr Thr Cys Trp Ile Ala Ala Glu Phe Val Phe Val Phe Phe Met Tyr
465                 470                 475                 480

Val Glu Thr Lys Gly Pro Thr Leu Glu Leu Ala Lys Val Ile Asp
                485                 490                 495

Gly Asp Glu Ala Asp Val Ala His Ile Asp Ile His Gln Val Glu Lys
            500                 505                 510

Glu Val Glu Ile His Glu His Glu Gly Lys Ser Val Ala
                515                 520                 525

<210> SEQ ID NO 2
<211> LENGTH: 318
<212> TYPE: PRT
<213> ORGANISM: Scheffersomyces stipitis

<400> SEQUENCE: 2

Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
                20                  25                  30

Arg Ala Ile Lys Thr Gly Tyr Arg Leu Phe Asp Gly Ala Glu Asp Tyr
            35                  40                  45

Ala Asn Glu Lys Leu Val Gly Ala Gly Val Lys Lys Ala Ile Asp Glu
        50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175
```

```
Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 3
<211> LENGTH: 322
<212> TYPE: PRT
<213> ORGANISM: N. crassa

<400> SEQUENCE: 3

```
Met Val Pro Ala Ile Lys Leu Asn Ser Gly Phe Asp Met Pro Gln Val
1               5                   10                  15

Gly Phe Gly Leu Trp Lys Val Asp Gly Ser Ile Ala Ser Asp Val Val
            20                  25                  30

Tyr Asn Ala Ile Lys Ala Gly Tyr Arg Leu Phe Asp Gly Ala Cys Asp
        35                  40                  45

Tyr Gly Asn Glu Val Glu Cys Gly Gln Gly Val Ala Arg Ala Ile Lys
    50                  55                  60

Glu Gly Ile Val Lys Arg Glu Glu Leu Phe Ile Val Ser Lys Leu Trp
65                  70                  75                  80

Asn Thr Phe His Asp Gly Asp Arg Val Glu Pro Ile Val Arg Lys Gln
                85                  90                  95

Leu Ala Asp Trp Gly Leu Glu Tyr Phe Asp Leu Tyr Leu Ile His Phe
            100                 105                 110

Pro Val Ala Leu Glu Tyr Val Asp Pro Ser Val Arg Tyr Pro Pro Gly
        115                 120                 125

Trp His Phe Asp Gly Lys Ser Glu Ile Arg Pro Ser Lys Ala Thr Ile
    130                 135                 140

Gln Glu Thr Trp Thr Ala Met Glu Ser Leu Val Glu Lys Gly Leu Ser
145                 150                 155                 160

Lys Ser Ile Gly Val Ser Asn Phe Gln Ala Gln Leu Leu Tyr Asp Leu
                165                 170                 175

Leu Arg Tyr Ala Lys Val Arg Pro Ala Thr Leu Gln Ile Glu His His
            180                 185                 190

Pro Tyr Leu Val Gln Gln Asn Leu Leu Asn Leu Ala Lys Ala Glu Gly
        195                 200                 205

Ile Ala Val Thr Ala Tyr Ser Ser Phe Gly Pro Ala Ser Phe Arg Glu
    210                 215                 220

Phe Asn Met Glu His Ala Gln Lys Leu Gln Pro Leu Leu Glu Asp Pro
225                 230                 235                 240
```

```
Thr Ile Lys Ala Ile Gly Asp Lys Tyr Asn Lys Asp Pro Ala Gln Val
                245                 250                 255

Leu Leu Arg Trp Ala Thr Gln Arg Gly Leu Ala Ile Ile Pro Lys Ser
                260                 265                 270

Ser Arg Glu Ala Thr Met Lys Ser Asn Leu Asn Ser Leu Asp Phe Asp
            275                 280                 285

Leu Ser Glu Glu Asp Ile Lys Thr Ile Ser Gly Phe Asp Arg Gly Ile
        290                 295                 300

Arg Phe Asn Gln Pro Thr Asn Tyr Phe Ser Ala Glu Asn Leu Trp Ile
305                 310                 315                 320

Phe Gly

<210> SEQ ID NO 4
<211> LENGTH: 543
<212> TYPE: PRT
<213> ORGANISM: N. crassa

<400> SEQUENCE: 4

Met Pro Leu Val Lys Asn Pro Ile Leu Pro Gly Phe Asn Pro Asp Pro
1               5                   10                  15

Ser Val Leu Arg Val Gly Gln Asp Tyr Tyr Ile Ala Thr Ser Thr Phe
                20                  25                  30

Glu Trp Tyr Pro Gly Val Gln Ile His His Ser Thr Asp Leu Ala Asn
            35                  40                  45

Trp Thr Leu Leu Thr Arg Pro Leu Asn Arg Lys Ser Gln Leu Asp Met
        50                  55                  60

Arg Gly Asp Pro Asp Ser Cys Gly Val Trp Ala Pro Cys Leu Ser His
65              70                  75                  80

Asp Gly Asp Lys Phe Trp Leu Val Tyr Thr Asp Val Lys Arg Lys Asp
                85                  90                  95

Gly Ser Phe Lys Asp Ala His Asn Phe Ile Val Trp Ala Asp Lys Ile
                100                 105                 110

Asp Gly Glu Trp Ser Asp Pro Val Tyr Val Asn Ser Ser Gly Phe Asp
            115                 120                 125

Pro Ser Leu Phe His Asp Pro Asp Ser Gly Lys Lys Tyr Phe Val Asn
        130                 135                 140

Met Leu Trp Asp His Arg Arg Pro Leu Leu Phe Ala Gly Ile Ala
145                 150                 155                 160

Val Gln Glu Trp Asp Ala Lys Thr Lys Lys Leu Val Gly Glu Arg Lys
                165                 170                 175

Asn Val Tyr Gln Gly Thr Glu Leu Ala Leu Ala Glu Ala Pro His Val
                180                 185                 190

Tyr Lys Arg Asn Gly Trp Tyr Tyr Leu Leu Ile Ala Glu Gly Gly Thr
            195                 200                 205

Gly Tyr Glu His Ala Cys Thr Leu Ala Arg Ser Lys Asp Ile Trp Gly
        210                 215                 220

Pro Tyr Lys Thr His Pro Glu Lys His Val Leu Thr Ser Lys Asp His
225                 230                 235                 240

Pro Arg Ala Ala Leu Gln Arg Ala Gly His Gly Asp Ile Val Glu Ile
                245                 250                 255

Glu Asp Gly Arg Thr Tyr Leu Val His Leu Thr Gly Arg Pro Thr Thr
                260                 265                 270

Gln Leu Arg Arg Cys Val Leu Gly Arg Glu Thr Ala Ile Gln Glu Cys
            275                 280                 285
```

-continued

```
Tyr Trp Lys Asp Asp Trp Leu Tyr Val Lys Asn Gly Pro Val Pro Ser
        290                 295                 300

Leu Trp Val Asp Leu Leu Gly Glu Arg Asp Glu Ser Lys Tyr Trp Glu
305                 310                 315                 320

Glu Lys Arg Tyr Thr Phe Lys Asp Gly Leu His Lys Asp Phe Gln Trp
                325                 330                 335

Leu Arg Thr Pro Glu Thr Glu Arg Ile Phe Asn Val Lys Asp Gly Lys
            340                 345                 350

Leu Thr Leu Ile Gly Arg Glu Ala Ile Gly Ser Trp Phe Glu Gln Ala
        355                 360                 365

Leu Val Ala Arg Arg Gln Glu His Phe Ser Tyr Asp Ala Glu Thr Val
    370                 375                 380

Ile Asp Phe Ser Pro Thr Asp Glu Arg Gln Phe Ala Gly Leu Thr Ala
385                 390                 395                 400

Tyr Tyr Cys Arg Tyr Asn Phe Phe Tyr Leu Thr Val Thr Ala His Ser
                405                 410                 415

Asp Gly Gln Arg Glu Leu Leu Ile Met Ser Ser Glu Ala Ser Trp Pro
            420                 425                 430

Ile Gly Asn Leu Asn Thr Pro Tyr Val Pro Tyr Val Gln Ile Pro Asn
        435                 440                 445

Glu Gly Lys Val Lys Leu Ala Leu Thr Ile Arg Gly Asn Gln Leu Gln
    450                 455                 460

Phe Tyr Tyr Ala Val Leu Asp Ser Gly Asp Glu Glu Leu Lys Lys Ile
465                 470                 475                 480

Gly Pro Val Phe Asp Ala Ser Ile Val Ser Asp Glu Cys Gly Gly His
                485                 490                 495

Gln Gln His Gly Ser Phe Thr Gly Ala Phe Val Gly Val Ala Ala Ser
            500                 505                 510

Asp Leu Asn Gly Leu Ala Ala Glu Ala Lys Phe Asp Tyr Leu Leu Tyr
        515                 520                 525

Lys Pro Val Lys Asn Gln Gln Asp Ala Tyr Val Arg Asp Asn Glu
    530                 535                 540

<210> SEQ ID NO 5
<211> LENGTH: 533
<212> TYPE: PRT
<213> ORGANISM: Bacillus subtilis

<400> SEQUENCE: 5

Met Lys Ile Thr Asn Pro Val Leu Lys Gly Phe Asn Pro Asp Pro Ser
1               5                   10                  15

Ile Cys Arg Ala Gly Glu Asp Tyr Tyr Ile Ala Val Ser Thr Phe Glu
            20                  25                  30

Trp Phe Pro Gly Val Gln Ile His His Ser Lys Asp Leu Val Asn Trp
        35                  40                  45

His Leu Val Ala His Pro Leu Gln Arg Val Ser Gln Leu Asp Met Lys
    50                  55                  60

Gly Asn Pro Asn Ser Gly Gly Val Trp Ala Pro Cys Leu Ser Tyr Ser
65                  70                  75                  80

Asp Gly Lys Phe Trp Leu Ile Tyr Thr Asp Val Lys Val Val Asp Gly
                85                  90                  95

Ala Trp Lys Asp Cys His Asn Tyr Leu Val Thr Cys Glu Thr Ile Asn
            100                 105                 110

Gly Asp Trp Ser Glu Pro Ile Lys Leu Asn Ser Ser Gly Phe Asp Ala
```

```
              115                 120                 125
Ser Leu Phe His Asp Thr Asp Gly Lys Lys Tyr Leu Leu Asn Met Leu
130                 135                 140

Trp Asp His Arg Ile Asp Arg His Ser Phe Gly Ile Val Ile Gln
145                 150                 155                 160

Glu Tyr Ser Asp Lys Glu Gln Lys Leu Ile Gly Lys Pro Lys Val Ile
                165                 170                 175

Phe Glu Gly Thr Asp Arg Lys Leu Thr Glu Ala Pro His Leu Tyr His
                180                 185                 190

Ile Gly Asn Tyr Tyr Leu Leu Thr Ala Glu Gly Thr Arg Tyr
                195                 200                 205

Glu His Ala Ala Thr Ile Ala Arg Ser Ala Asn Ile Glu Gly Pro Tyr
210                 215                 220

Glu Val His Pro Asp Asn Pro Ile Leu Thr Ser Trp His Asp Pro Gly
225                 230                 235                 240

Asn Pro Leu Gln Lys Cys Gly His Ala Ser Ile Val Gln Thr His Thr
                245                 250                 255

Asp Glu Trp Tyr Leu Ala His Leu Thr Gly Arg Pro Ile His Pro Asp
                260                 265                 270

Asp Ser Ile Phe Gln Gln Arg Gly Tyr Cys Pro Leu Gly Arg Glu
                275                 280                 285

Thr Ala Ile Gln Lys Leu Tyr Trp Lys Asp Glu Trp Pro Tyr Val Val
290                 295                 300

Gly Gly Lys Glu Gly Ser Leu Glu Val Asp Ala Pro Ser Ile Pro Glu
305                 310                 315                 320

Thr Ile Phe Glu Ala Thr Tyr Pro Glu Val Asp Glu Phe Glu Asp Ser
                325                 330                 335

Thr Leu Asn Ile Asn Phe Gln Thr Leu Arg Ile Pro Phe Thr Asn Glu
                340                 345                 350

Leu Gly Ser Leu Thr Gln Ala Pro Asn His Leu Arg Leu Phe Gly His
                355                 360                 365

Glu Ser Leu Thr Ser Thr Phe Thr Gln Ala Phe Val Ala Arg Arg Trp
370                 375                 380

Gln Ser Leu His Phe Glu Ala Glu Thr Ala Val Glu Phe Tyr Pro Glu
385                 390                 395                 400

Asn Phe Gln Gln Ala Ala Gly Leu Val Asn Tyr Tyr Asn Thr Glu Asn
                405                 410                 415

Trp Thr Ala Leu Gln Val Thr His Asp Glu Glu Leu Gly Arg Ile Leu
                420                 425                 430

Glu Leu Thr Ile Cys Asp Asn Phe Ser Phe Ser Gln Pro Leu Asn Asn
                435                 440                 445

Lys Ile Val Ile Pro Arg Glu Val Lys Tyr Val Tyr Leu Arg Val Asn
                450                 455                 460

Ile Glu Lys Asp Lys Tyr Tyr Tyr Phe Tyr Ser Phe Asn Lys Glu Asp
465                 470                 475                 480

Trp His Lys Ile Asp Ile Ala Leu Glu Ser Lys Lys Leu Ser Asp Asp
                485                 490                 495

Tyr Ile Arg Gly Gly Phe Thr Gly Ala Phe Val Gly Met Gln
                500                 505                 510

Cys Gln Asp Thr Gly Gly Asn His Ile Pro Ala Asp Phe Arg Tyr Phe
                515                 520                 525

Arg Tyr Lys Glu Lys
                530
```

<210> SEQ ID NO 6
<211> LENGTH: 536
<212> TYPE: PRT
<213> ORGANISM: Escherichia coli

<400> SEQUENCE: 6

```
Met Glu Ile Thr Asn Pro Ile Leu Thr Gly Phe Asn Pro Asp Pro Ser
1               5                   10                  15

Leu Cys Arg Gln Gly Glu Asp Tyr Tyr Ile Ala Thr Ser Thr Phe Glu
            20                  25                  30

Trp Phe Pro Gly Val Arg Ile Tyr His Ser Arg Asp Leu Lys Asn Trp
        35                  40                  45

Ser Leu Val Ser Thr Pro Leu Asp Arg Val Ser Met Leu Asp Met Lys
    50                  55                  60

Gly Asn Pro Asp Ser Gly Gly Ile Trp Ala Pro Cys Leu Ser Tyr Ala
65                  70                  75                  80

Asp Gly Lys Phe Trp Leu Leu Tyr Thr Asp Val Lys Ile Val Asp Ser
                85                  90                  95

Pro Trp Lys Asn Gly Arg Asn Phe Leu Val Thr Ala Pro Ser Ile Glu
            100                 105                 110

Gly Pro Trp Ser Glu Pro Ile Pro Met Gly Asn Gly Gly Phe Asp Pro
        115                 120                 125

Ser Leu Phe His Asp Asp Asp Gly Arg Lys Tyr Tyr Ile Tyr Arg Pro
130                 135                 140

Trp Gly Pro Arg His His Ser Asn Pro His Asn Thr Ile Val Leu Gln
145                 150                 155                 160

Ala Phe Asp Pro Gln Thr Gly Thr Leu Ser Pro Glu Arg Lys Thr Leu
                165                 170                 175

Phe Thr Gly Thr Pro Leu Cys Tyr Thr Glu Gly Ala His Leu Tyr Arg
            180                 185                 190

His Ala Gly Trp Tyr Tyr Leu Met Val Ala Glu Gly Gly Thr Ser Tyr
        195                 200                 205

Glu His Ala Val Val Val Leu Arg Ser Lys Asn Ile Asp Gly Pro Tyr
    210                 215                 220

Glu Leu His Pro Asp Val Thr Met Met Thr Ser Trp His Leu Pro Glu
225                 230                 235                 240

Asn Pro Leu Gln Lys Ser Gly His Gly Ser Leu Leu Gln Thr His Thr
                245                 250                 255

Gly Glu Trp Tyr Met Ala Tyr Leu Thr Ser Arg Pro Leu Arg Leu Pro
            260                 265                 270

Gly Val Pro Leu Leu Ala Ser Gly Arg Gly Tyr Cys Pro Leu Gly
        275                 280                 285

Arg Glu Thr Gly Ile Ala Arg Ile Glu Trp Arg Asp Gly Trp Pro Tyr
    290                 295                 300

Val Glu Gly Gly Lys His Ala Gln Leu Thr Val Lys Gly Pro Gln Val
305                 310                 315                 320

Ala Glu Gln Pro Ala Ala Val Pro Gly Asn Trp Arg Asp Asp Phe Asp
                325                 330                 335

Ala Ser Ser Leu Asp Pro Glu Leu Gln Thr Leu Arg Ile Pro Phe Asp
            340                 345                 350

Asp Thr Leu Gly Ser Leu Thr Ala Arg Pro Gly Phe Leu Arg Leu Tyr
        355                 360                 365

Gly Asn Asp Ser Leu Asn Ser Thr Phe Thr Gln Ser Thr Val Ala Arg
```

```
                    370                 375                 380
Arg Trp Gln His Phe Ala Phe Arg Ala Glu Thr Arg Met Glu Phe Ser
385                 390                 395                 400

Pro Val His Phe Gln Gln Ser Ala Gly Leu Thr Cys Tyr Tyr Asn Ser
                    405                 410                 415

Lys Asn Trp Ser Tyr Cys Phe Val Asp Tyr Glu Glu Gly Gln Gly Arg
                420                 425                 430

Thr Ile Lys Val Ile Gln Leu Asp His Asn Val Pro Ser Trp Pro Leu
            435                 440                 445

His Glu Gln Pro Ile Pro Val Pro Glu His Ala Glu Ser Val Trp Leu
    450                 455                 460

Arg Val Asp Val Asp Thr Leu Val Tyr Arg Tyr Ser Tyr Ser Phe Asp
465                 470                 475                 480

Gly Glu Thr Trp His Thr Val Pro Val Thr Tyr Glu Ala Trp Lys Leu
                    485                 490                 495

Ser Asp Asp Tyr Ile Gly Gly Arg Gly Phe Phe Thr Gly Ala Phe Val
                500                 505                 510

Gly Leu His Cys Glu Asp Ile Ser Gly Asp Gly Cys Tyr Ala Asp Phe
            515                 520                 525

Asp Tyr Phe Thr Tyr Glu Pro Val
    530                 535

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Any Amino Acid

<400> SEQUENCE: 7

Arg Xaa Leu Tyr Thr Gly Tyr Asp Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7
<223> OTHER INFORMATION: Xaa = Any Amino Acid

<400> SEQUENCE: 8

Gly Phe Gly Asn Ser Xaa Xaa Gln
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Any Amino Acid

<400> SEQUENCE: 9
```

```
Leu Leu Xaa His Pro Gln His Arg
  1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Phe or Tyr
<220> FEATURE:
<221> NAME/KEY: VARIANT
<222> LOCATION: 3
<223> OTHER INFORMATION: Xaa = Any Amino Acid
<220> FEATURE:
<221> NAME/KEY: VARIANT
<222> LOCATION: 6
<223> OTHER INFORMATION: Xaa = Arg or Lys
<220> FEATURE:
<221> NAME/KEY: VARIANT
<222> LOCATION: 7
<223> OTHER INFORMATION: Xaa = Asp or Glu

<400> SEQUENCE: 10

Glu Xaa Xaa Glu Ile Xaa Xaa Thr
  1               5

<210> SEQ ID NO 11
<211> LENGTH: 4
<212> TYPE: PRT
<213> ORGANISM: Artificial Sequence
<220> FEATURE:
<223> OTHER INFORMATION: Synthetic Construct

<400> SEQUENCE: 11

Trp Ser Gly Leu
  1

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

Gly Pro Thr Leu Glu Glu
  1               5
```

METHODS FOR PRODUCTION OF XYLOSYLXYLITOL OLIGOMERS

CROSS-REFERENCE TO RELATED APPLICATION(S)

This application is a continuation of PCT/US2015/037115, filed Jun. 23, 2015, which claims the benefit of Ser. No. 62/016,555, filed on Jun. 24, 2014, which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 416272008040SEQLIST.TXT, date recorded: Jun. 18, 2015, size: 25 KB).

FIELD

The present disclosure relates generally to the production of xylosyl-xylitol oligomers, and more specifically to biological methods for producing xylosyl-xylitol oligomers in host cells.

BACKGROUND

Lignocellulosic biomass derived from plant cell walls is the most abundant raw material for biofuels and renewable chemicals production. Hemicellulose comprises about 30% of the total weight of lignocellulosic biomass. The predominant form of hemicellulose are heteroxylans, which contain a backbone of 1,4-linked β-D-xylose polymers and various decorations of arabinose, ferulic acid, galactose, glucuronic acid, and acetyl ester. In contrast to cellulose, hemicellulose components are readily depolymerized into short oligomers and released into the liquid phase during pretreatment. It is of great interest to convert the released hemicellulose components into fuels or other value-add chemicals for building an economical biomass conversion process.

It has been estimated that there are ten times more microorganisms than human cells in a healthy adult (Savage et al., 1977). The symbiosis between the microbiome and human organs is increasingly recognized as a major player in health and well-being. Xylooligosaccharides and xylitol, both derived from hemicellulose, can benefit gut flora and oral flora, respectively.

Xylooligosaccharides (XOS, also called xylodextrins) are naturally occurring oligosaccharides, found in bamboo shoots, fruits, vegetables, milk and honey (Vazquez et al., 2000). Industrial scale production of XOS can be carried out with much less expensive lignocellulosic materials by hydrothermal treatment or enzymatic hydrolysis (Aachary et al., 2011). A broad range of applications of XOS have been demonstrated, including as functional food, prevention and treatment of gastrointestinal infections, animal feed for fish and poultry, agricultural yield enhancer and ripening agent, and as active agents against osteoporosis, pruritus cutaneous, otitis, and skin and hair disorders. In the current market, the most important applications of XOS correspond to ingredients for functional foods as a prebiotic, or formulated as synbiotics (Schrezenmeir et al., 2001). A prebiotic is a "nondigestible food ingredient that beneficially affects the host by selectively stimulating the growth and/or activity of one or a limited number of bacteria in the colon and thus improves the host's health" (Gibson et al., 1995). XOS has been shown to promote beneficial bacteria *Bifidobacterium adolescentis* growth in vitro (Okazaki et al., 1990) and in vivo (Hsu et al., 2004). It has been estimated that the prebiotics market will reach $4.8 billion by 2018, and the current largest producer (Shandong Longlive Bio-technology Co., Ltd.) has a 10,000 metric ton annual capacity of XOS.

Xylitol is another hemicellulose-derived compound beneficial to human health. For many bacteria and yeasts, the uptake of non-utilizable xylitol interferes with hexose utilization, which helps the human body to rebuild a healthy microbiome. Xylitol has been used to prevent middle ear infections (Azarpazhooh et al., 2011) and tooth decay (Maguire et al., 2003; Makinen et al., 1992). In addition, xylitol possess 33% fewer calories but similar sweetness compared to sucrose (Hyvonen et al., 1982) and has been widely used as a substitute sweetener. While chemical hydrogenation of xylose remains the major industrial method of xylitol production, microbial fermentation has become more popular in the newly built plants due to lower conversion cost. The annual production of xylitol is between 20,000 and 40,000 tons, based on a 2007 report (Granstrom et al., 2007). There exists a need for improved methods of producing xylooligosaccharides and related compounds, such as xylooligosaccharides with xylitol components.

BRIEF SUMMARY

In one aspect, the present disclosure relates to a method of producing a xylosyl-xylitol oligomer, the method including: a) providing a host cell including a recombinant xylodextrin transporter polypeptide, where the xylodextrin transporter polypeptide transports xylodextrins into the host cell, and a recombinant xylose reductase polypeptide including xylodextrin reductase activity; and b) culturing the host cell in a medium including xylodextrins, where the host cell produces a xylosyl-xylitol oligomer from the xylodextrins. In some embodiments, the host cell is a fungal host cell. In some embodiments, the host cell is *Saccharomyces cerevisiae*. In some embodiments that may be combined with any of the preceding embodiments, the recombinant xylodextrin transporter polypeptide includes an amino acid sequence having at least 80% amino acid identity to CDT-2 from *Neurospora crassa*. In some embodiments that may be combined with any of the preceding embodiments, the recombinant xylose reductase polypeptide includes an amino acid sequence having at least 80% amino acid identity to XYL1 from *Scheffersomyces stipitis*. In some embodiments that may be combined with any of the preceding embodiments, one or more of the xylodextrins is xylobiose or xylotriose. In some embodiments that may be combined with any of the preceding embodiments, at least one xylosyl-xylitol oligomer is xylosyl-xylitol or xylosyl-xylosyl-xylitol. In some embodiments that may be combined with any of the preceding embodiments, the activity of one or more β-xylosidase polypeptides comprising xylosyl-xylitol hydrolase activity in the host cell is decreased as compared to a corresponding control cell. In some embodiments, activity of the one or more β-xylosidase polypeptides is decreased due to decreased abundance of the one or more polypeptides as compared to a corresponding control cell. In some embodiments, abundance of the one or more β-xylosidase polypeptides is decreased due to decreased expression of the one or more polypeptides. In some embodiments, expression of the one or more β-xylosidase polypeptides is decreased due to a mutation. In some embodiments that may be combined with any of the preceding embodiments, the activity of one or more xylitol dehydrogenase polypeptides in the host cell is decreased as compared to a corresponding control cell. In some embodiments, abundance of the one or more xylitol dehydrogenase polypeptides is decreased due to decreased expression of the one or more polypeptides. In some embodiments, expression of the one or more xylitol dehydrogenase polypeptides is decreased due to a mutation. In some embodiments that may be combined with any of the preceding embodiments, the method further includes, after b), a step of substantially purifying a xylosyl-xylitol oligomer from the medium.

In another aspect, the present disclosure relates to a composition including a xylosyl-xylitol oligomer purified according to the methods of the previous aspect. In some embodiments, the composition includes at least one substantially purified xylosyl-xylitol oligomer selected from xylosyl-xylitol and xylosyl-xylosyl-xylitol.

In another aspect, the present disclosure relates to a method of producing a xylosyl-xylitol oligomer, the method including: a) providing a host cell including a xylodextrin transporter polypeptide, where the xylodextrin transporter polypeptide transports xylodextrins into the host cell, and a xylose reductase polypeptide including xylodextrin reductase activity, where the activity of one or more β-xylosidase polypeptides including xylosyl-xylitol hydrolase activity in the host cell is decreased as compared to a corresponding control cell; and b) culturing the host cell in a medium including xylodextrins, where the host cell produces a xylosyl-xylitol oligomer from the xylodextrins. In some embodiments, the host cell is a fungal host cell. In some embodiments, the host cell is Neurospora crassa. In some embodiments that may be combined with any of the preceding embodiments, activity of the one or more β-xylosidase polypeptides is decreased due to decreased abundance of the one or more polypeptides as compared to a corresponding control cell. In some embodiments, abundance of the one or more β-xylosidase polypeptides is decreased due to decreased expression of the one or more polypeptides. In some embodiments, expression of the one or more β-xylosidase polypeptides is decreased due to a mutation. In some embodiments that may be combined with any of the preceding embodiments, the activity of one or more xylitol dehydrogenase polypeptides in the host cell is decreased as compared to a corresponding control cell. In some embodiments, abundance of the one or more xylitol dehydrogenase polypeptides is decreased due to decreased expression of the one or more polypeptides. In some embodiments, expression of the one or more xylitol dehydrogenase polypeptides is decreased due to a mutation. In some embodiments that may be combined with any of the preceding embodiments, one or more of the xylodextrins is xylobiose or xylotriose. In some embodiments that may be combined with any of the preceding embodiments, at least one xylosyl-xylitol oligomer is xylosyl-xylitol or xylosyl-xylosyl-xylitol. In some embodiments that may be combined with any of the preceding embodiments, the method further includes, after b), a step of substantially purifying a xylosyl-xylitol oligomer from the medium.

In another aspect, the present disclosure relates to a composition including a xylosyl-xylitol oligomer purified according to the methods of the previous aspect. In some embodiments, the composition includes at least one substantially purified xylosyl-xylitol oligomer selected from xylosyl-xylitol and xylosyl-xylosyl-xylitol.

DESCRIPTION OF THE FIGURES

The patent or application file contains at least one drawing executed in color. Copies of this patent or patent application publication with color drawings will be provided by the office upon request and payment of the necessary fee.

FIG. 2A-FIG. 2B illustrate consumption of xylodextrins by engineered S. cerevisiae. FIG. 2A illustrates a culture of S. cerevisiae expressing an XR/XDH xylose consumption pathway, CDT-2, and GH43-2 grown at a starting cell density of $OD_{600}=1$ under aerobic conditions, with xylose and xylodextrins as the carbon source. FIG. 2B illustrates a culture as in FIG. 2A, but with a starting cell density of $OD_{600}=20$. The concentrations of the remaining xylose (X1) and xylodextrins with higher DPs (X2-X5) in the culture broth after different periods of time are shown in both panels.

FIG. 3A illustrates the concentrations of the remaining sugars in the culture broth of WT D452-2 strain with starting cell density at $OD_{600}=1$ after different periods of time. FIG. 3B illustrates the concentrations of the remaining sugars in the culture broth of D452-2 with a S. stipitis xylose utilization pathway (plasmid pLNL78) with a starting cell density at $OD_{600}=1$ after different periods of time. FIG. 3C illustrates the concentrations of the remaining sugars in the culture broth of WT D452-2 strain with a starting cell density at $OD_{600}=20$ after different periods of time. FIG. 3D illustrates the concentrations of the remaining sugars in the culture broth of D452-2 with a S. stipitis xylose utilization pathway (plasmid pLNL78) with a starting cell density at $OD_{600}=20$ after different periods of time. In all panels, xylose (X1), and xylodextrins of higher DPs (X2-X5) are shown.

FIG. 4A-FIG. 4B illustrate LC-MS and LC-MS/MS spectra for xylosyl-xylitol oligomers. FIG. 4A illustrates LC-MS and LC-MS/MS spectra for xylosyl-xylitol (structure shown). High resolution MS spectra show m/z ratios for the negative ion mode. The deprotonated and formate adduct ions were determined with an accuracy of 0.32 and 0.33 ppm, respectively. The MS/MS spectrum in the lower panel shows the product ion matching the predicted fragment. The parental ion, [xylosyl-xylitol—H]⁻, is denoted with the black diamond mark. FIG. 4B illustrates LC-MS and LC-MS/MS spectra for xylosyl-xylosyl-xylitol (structure shown). The deprotonated and formate adduct ions were determined with an accuracy of 0.51 and 0.37 ppm, respectively. The MS/MS spectrum in the lower panel shows the product ions matching the predicted fragments. The parental ion, [xylosyl-xylosyl-xylitol—H]⁻, is denoted with the black diamond mark.

FIG. 6A illustrates the xylodextrin content of the reaction, X1-X4, before the addition of XYR-1. FIG. 6B illustrates the xylodextrin and xylosyl-xylitol oligomer contents post-reaction. Xylose, xylodextrins with DP of 2 to 4, and their reduced xylosyl-xylitol oligomer products are labeled X1-X4 (xylodextrins) and xlt1-xlt4 (xylosyl-xylitol oligomers), respectively.

FIG. 8A illustrates hydrolysis of xylosyl-xylitol by GH43-7. Purified GH43-2 or GH43-7 were incubated with xylosyl-xylitol and xylobiose, and concentrations (mM) of the resulting products were measured by ion-exclusion HPLC. FIG. 8B illustrates a chromatogram of the xylosyl-xylitol hydrolysis products by β-xylosidases as shown in FIG. 8A. Reaction products from the enzymatic assays were resolved by ion-exclusion HPLC. Peak areas were used to quantify the concentration of substrates and products at the end of the reaction.

FIG. 9A illustrates yeast growth curves with xylodextrin as the sole carbon source under aerobic conditions with a cell density at $OD_{600}=1$. Cultures of yeast strain SR8 without plasmids, or transformed with plasmid expressing CDT-2 and GH43-2 (pXD8.4), CDT-2 and GH43-7 (pXD8.6) or CDT-2, GH43-2, and GH43-7 (pXD8.7) are shown. FIG. 9B illustrates xylobiose consumption with xylodextrin as the sole carbon source under microaerobic conditions for yeast with pXD8.4 at a starting cell density of $OD_{600}=20$. FIG. 9C illustrates xylobiose consumption with xylodextrin as the sole carbon source under microaerobic conditions for yeast with pXD8.6 at a starting cell density of $OD_{600}=20$. FIG. 9D illustrates xylobiose consumption with xylodextrin as the sole carbon source under microaerobic conditions for yeast with pXD8.7 at a starting cell density of $OD_{600}=20$. FIG. 9E illustrates xylobiose consumption with xylodextrin as the sole carbon source under microaerobic conditions for yeast with pXD8.4 at a starting cell density of $OD_{600}=80$. FIG. 9F illustrates xylobiose consumption with xylodextrin as the sole carbon source under microaerobic conditions for yeast with pXD8.6 at a starting cell density of $OD_{600}=80$. FIG. 9G illustrates xylobiose consumption with xylodextrin as the sole carbon source under microaerobic conditions for yeast with pXD8.7 at a starting cell density of $OD_{600}=80$. FIG. 9H illustrates ethanol production with xylodextrin as the sole carbon source under microaerobic conditions for yeast with pXD8.4, pXD8.6, or pXD8.7 at a starting cell density of $OD_{600}=80$. All growth experiments were performed in biological triplicate and error bars indicate the standard deviation between experiments.

FIG. 13A illustrates a schematic of the engineered (xylosyl)$_n$-xylitol production pathway. Xylodextrins enter a cell through a xylodextrin transporter, and a xylose reductase converts the xylodextrin to a xylosyl-xylitol oligomer. FIG. 13B illustrates the fermentation profile of (xylosyl)$_n$-xylitol production by engineered *S. cerevisiae*.

FIG. 20A-FIG. 20B illustrates xylobiase activity of the predicted β-xylosidase GH43-2. FIG. 20A illustrates GH43-2 hydrolysis of xylodextrins with degrees of polymerization from at least 2-8 (X2-X8). The 30 min chromatogram is offset for clarity. FIG. 20B illustrates the pH optimum of GH43-2, determined by measuring the extent of hydrolysis of xylobiose to xylose. The HPAEC chromatogram peak area change for xylose is shown.

FIG. 24A illustrates xylodextrin-derived carbohydrate levels seen in chromatograms of intracellular metabolites for N. crassa, Trichoderma reesei, Aspergillus nidulans and B. subtilis grown on xylodextrins. Compounds are abbreviated as follows: X1, xylose; X2, xylobiose; X3, xylotriose; X4, xylotetraose; xlt, xylitol; xlt2, xylosyl-xylitol; xlt3, xylosyl-xylosyl-xylitol. FIG. 24B illustrates a phylogenetic tree of the organisms shown to produce xylosyl-xylitols during growth on xylodextrins in the experiments described herein. Ages taken from (Wellman, Osterloff, and Mohiuddin 2003; Galagan et al. 2005; Hedges, Dudley, and Kumar 2006).

FIG. 27A illustrates anaerobic fermentation of xylodextrins and xylose, in a fed-batch reactor. Strain SR8U expressing CDT-2, GH43-2, and GH43-7 (plasmid pXD8.7) was used at an initial OD600 of 20. Solid lines represent concentrations of compounds in the media. Blue dotted line shows the total amount of xylose added to the culture over time. Error bars represent standard deviations of biological duplicates. FIG. 27B illustrates anaerobic fermentation of xylodextrins and glucose, in a fed-batch reactor. Glucose was not detected in the fermentation broth. Error bars represent standard deviations of biological duplicates.

FIG. 29A illustrates fermentation profile of the strain in oMM medium containing 4% xylodextrin in the reactor without feeding xylose. FIG. 29B illustrates fermentation profile of the strain in oMM medium without xylodextrin in the reactor but with continuous xylose feeding.

FIG. 33A illustrates sucrose fermentation. Vertical axis, g/L; horizontal axis, time in hours. FIG. 33B illustrates xylodextrin and sucrose batch co-fermentation using strain SR8U expressing CDT-2, GH43-2, and GH43-7 (plasmid pXD8.7). Vertical axis, g/L; horizontal axis, time in hours. The xylodextrins were supplied at 10 g/L which containing xylobiose (4.2 g/L) and xylotriose (2.3 g/L). Not fermented in the timeframe of this experiment, the xylodextrin sample also included xylotetraose and xylopentaose, in addition to hemicellulose modifiers such as acetate.

DETAILED DESCRIPTION

Figure 1:
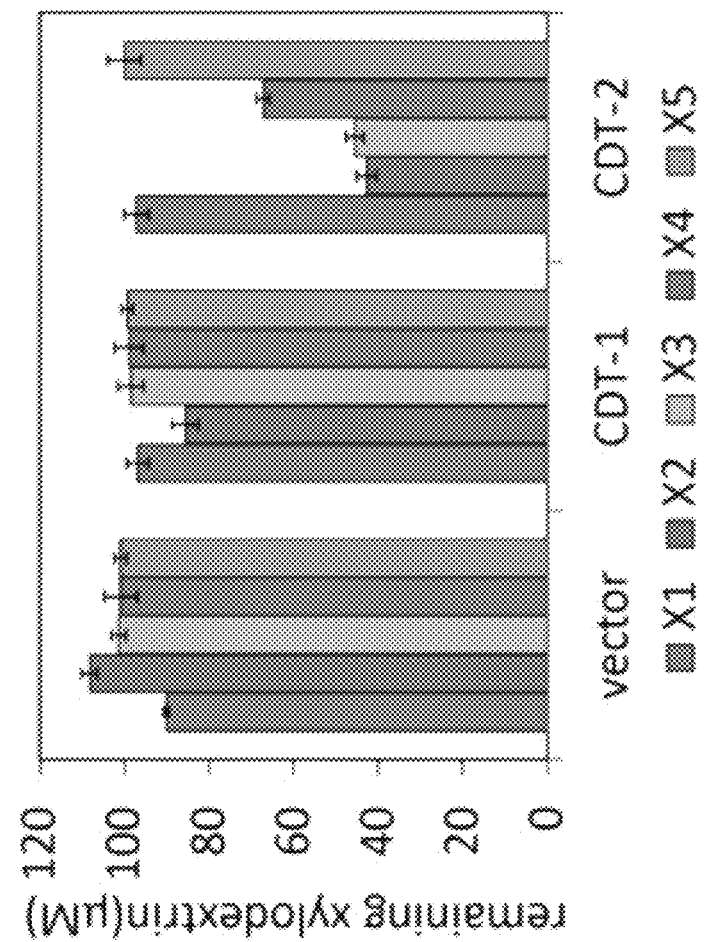
FIG. 1 illustrates transport of xylodextrins into the cytoplasm of S. cerevisiae strains expressing N. crassa transporters. The starting xylodextrin concentration for each purified component was 100 μM. The remaining xylose (X1) and xylodextrins in the culture media are shown for experiments with S. cerevisiae harboring an empty expression plasmid (vector), or with S. cerevisiae individually expressing transporters CDT-1 or CDT-2. Xylodextrins used include xylobiose (X2), xylotriose (X3), xylotetraose (X4), and xylopentaose (X5).

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

The present disclosure relates to the production of xylosyl-xylitol oligomers, and more specifically to biological methods for producing xylosyl-xylitol oligomers in host cells.

The present disclosure is based, at least in part, on Applicants' discovery that a recombinant S. cerevisiae strain containing a xylodextrin transporter and a xylose reductase was able to produce and accumulate xylosyl-xylitol oligomers. Applicants' discovery was particularly surprising given that it was initially thought that this recombinant strain would utilize xylodextrins as an energy source by catabolism of these xylooligosaccharides into corresponding monomers, such as xylose and xylitol. Instead, Applicants' found that the recombinant xylose reductase in these yeast cells was converting xylodextrins into xylosyl-xylitol oligomers without any further metabolism of these compounds into corresponding monomers. As xylosyl-xylitol oligomers have a number of potential beneficial uses, such as use as sweetener agents, Applicants have demonstrated the establishment of a biological platform for the bioproduction of xylosyl-xylitol oligomers using living cells.

Accordingly, Applicants provide herein methods for producing xylosyl-xylitol oligomers in a host cell, as well as providing host cells suitable for the production of the xylosyl-xylitol oligomers. Culturing the host cells of the present disclosure in a growth medium that contains xylodextrins or a source of xylodextrins allows for the production of xylosyl-xylitol oligomers by the host cells.

Polypeptides of the Disclosure

The present disclosure relates to the production of xylosyl-xylitol oligomers using host cells. Host cells of the disclosure contain features that allow the host cell to produce and/or accumulate xylosyl-xylitol oligomers. In some embodiments, host cells of the present disclosure contain polypeptides that facilitate the production of xylosyl-xylitol oligomers. In some embodiments, host cells of the present disclosure have reduced activity of proteins that would otherwise act to prevent the production and/or accumulation of xylosyl-xylitol oligomers.

As used herein, a "polypeptide" is an amino acid sequence including a plurality of consecutive polymerized amino acid residues (e.g., at least about 15 consecutive polymerized amino acid residues). As used herein, "polypeptide" refers to an amino acid sequence, oligopeptide, peptide, protein, or portions thereof, and the terms "polypeptide" and "protein" are used interchangeably.

Xylodextrin Transporter Polypeptides

Host cells of the present disclosure contain a xylodextrin transporter polypeptide. Xylodextrin transporters generally refer to any sugar transport protein capable of transporting xylodextrins across the cell membrane of a cell. As used herein, "xylodextrin(s)" refers to xylose polymers of varying length and includes, for example, xylobiose (2 xylose monomers), xylotriose (3 xylose monomers), xylotetraose (4 xylose monomers), xylopentaose (5 xylose monomers), xylohexaose (6 xylose monomers), etc. In some embodiments, a xylodextrin transporter polypeptide of the present disclosure may have one or more of xylobiose transporter activity, xylotriose transporter activity, xylotetraose transporter activity, xylopentaose transporter activity, xylohexaose transporter activity, etc. "Xylodextrin" and "xylooligosaccharide" are used interchangeably herein.

Various xylodextrin transporters are known in the art and may be used in the methods of the present disclosure. Further, putative xylodextrin transporter polypeptides can be screened for xylodextrin transporter activity by any suitable method known in the art such as, for example, those disclosed herein.

Examples of suitable xylodextrin transporter polypeptides may include, for example, members of the Major Facilitator Superfamily sugar transporter family, such as NCU08114. Members of the Major Facilitator Superfamily (MFS) (Transporter Classification #2.A.1) of transporters almost always contain 12 transmembrane $\alpha$-helices, with an intracellular N- and C-terminus (S. S. Pao, I. T. Paulsen, M. H. Saier, Jr., *Microbiol Mol Biol Rev* 62, 1. Mar. 1998). While the primary sequence of MFS transporters varies widely, all are thought to share the tertiary structure of the *E. coli* lactose permease (LacY) (J. Abramson et al., *Science* 301, 610, August 2003), and the *E. coli* Pi/glycerol-3-phosphate (GlpT) (Y. Huang, M. J. Lemieux, J. Song, M. Auer, D. N. Wang, *Science* 301, 616, August 2003). In these examples, the six N- and C-terminal helices form two distinct domains connected by a long cytoplasmic loop between helices 6 and 7. This symmetry corresponds to a duplication event thought to have given rise to the MFS. Substrate binds within a hydrophilic cavity formed by helices 1, 2, 4, and 5 of the N-terminal domain, and helices 7, 8, 10, and 11 of the C-terminal domain. This cavity is stabilized by helices 3, 6, 9, and 12. In certain embodiments, xylodextrin transporters of the present disclosure may contain 12 transmembrane $\alpha$-helices, a loop sequence between $\alpha$-helix 6 and $\alpha$-helix 7, and have N- and C-termini that are intracellular.

MFS sugar transporters having xylodextrin transporter activity can be identified by one or more, two or more, three or more, four or more, five or more, or six of the following PROSITE motifs: R-x-L-Y-T-G-Y-D-G (SEQ ID NO: 7); G-F-G-N-S-x(2)-Q (SEQ ID NO: 8); L-L-x(1,30)-H-P-Q-H-R (SEQ ID NO: 9); E-[FY]-x-E-I-[RK]-[DE]-T (SEQ ID NO: 10); W-S-G-L (SEQ ID NO: 11); and G-P-T-L-E-E (SEQ ID NO: 12). Accordingly, in certain embodiments, xylodextrin transporters of the present disclosure may contain the motif R-x-L-Y-T-G-Y-D-G (SEQ ID NO: 7), the motif G-F-G-N-S-x(2)-Q (SEQ ID NO: 8), the motif L-L-x(1,30)-H-P-Q-H-R (SEQ ID NO: 9), the motif E-[FY]-x-

E-I-[RK]-[DE]-T (SEQ ID NO: 10), the motif W-S-G-L (SEQ ID NO: 11), and/or the motif G-P-T-L-E-E (SEQ ID NO: 12).

In certain embodiments, the loop connecting transmembrane helix 1 and transmembrane helix 2 of MFS sugar transporters having xylodextrin transporter activity may contain the motif, R-x-L-Y-T-G-Y-D-G (SEQ ID NO: 7). In other embodiments, transmembrane helix 4 of MFS sugar transporters having xylodextrin transporter activity may contain the motif, G-F-G-N-S-x(2)-Q (SEQ ID NO: 8). In further embodiments, the loop connecting transmembrane helix 4 and transmembrane helix 5 of MFS sugar transporters having xylodextrin transporter activity may contain the motif, L-L-x(1,30)-H-P-Q-H-R (SEQ ID NO: 9). In some embodiments, the sequence between transmembrane helix 6 and transmembrane helix 7 of MFS sugar transporters having xylodextrin transporter activity may contain the motif, E-[FY]-x-E-I-[RK]-[DE]-T (SEQ ID NO: 10). In other embodiments, transmembrane helix 10 of MFS sugar transporters having xylodextrin transporter activity may contain the motif, W-S-G-L (SEQ ID NO: 11). In further embodiments, the intracellular region of MFS sugar transporters having xylodextrin transporter activity may contain the motif, G-P-T-L-E-E (SEQ ID NO: 12).

Accordingly, in certain embodiments, xylodextrin transporters of the present disclosure may be MFS sugar transporters having xylodextrin transporter activity that contain 12 transmembrane α-helices (i.e., α-helix 1, α-helix 2, α-helix 3, α-helix 4, α-helix 5, α-helix 6, α-helix 7, α-helix 8, α-helix 9, α-helix 10, α-helix 11, α-helix 12), and at least one, at least two, at least three, at least four, at least five, or six sequence motifs selected from the motif R-x-L-Y-T-G-Y-D-G (SEQ ID NO: 7), the motif G-F-G-N-S-x(2)-Q (SEQ ID NO: 8), the motif L-L-x(1,30)-H-P-Q-H-R (SEQ ID NO: 9), the motif E-[FY]-x-E-I-[RK]-[DE]-T (SEQ ID NO: 10), the motif W-S-G-L (SEQ ID NO: 11), and the motif G-P-T-L-E-E (SEQ ID NO: 12). Additionally, the at least one, at least two, at least three, at least four, at least five, or six of these sequence motifs may be combined in any number of combinations. For example, in certain embodiments, recombinant xylodextrin transporters of the present disclosure may contain α-helix 1, α-helix 2, α-helix 3, α-helix 4, α-helix 5, α-helix 6, α-helix 7, α-helix 8, α-helix 9, α-helix 10, α-helix 11, α-helix 12, and one or more of the motif R-x-L-Y-T-G-Y-D-G (SEQ ID NO: 7), the motif G-F-G-N-S-x(2)-Q (SEQ ID NO: 8), the motif L-L-x(1,30)-H-P-Q-H-R (SEQ ID NO: 9), the motif E-[FY]-x-E-I-[RK]-[DE]-T (SEQ ID NO: 10), the motif W-S-G-L (SEQ ID NO: 11), and the motif G-P-T-L-E-E (SEQ ID NO: 12).

Exemplary xylodextrin transporters may include, for example, GI336463171, GI85111305, GI336265400, GI317144741, GI115492463, GI367019682, GI169613751, GI116180882, GI396476342, GI238485660, GI330924560, GI83768202, GI189198948, GI389624607, GI340924204, GI378727300, GI310790351, GI310800345, GI156057085, GI171687197, GI380474010, GI169851388, GI429858279, GI472245111, GI317451470, GI477537114, GI159123739, GI347840412, GI70983456, GI380480795, GI451851885, GI345565206, GI451995308, GI409045374, GI389739875, GI255954533, GI393212245, GI392561917, GI389747805, GI449542817, GI317431879, GI392589230, GI393212288, GI392594130, GI402080963, GI392589229, GI477517948, GI477532537, GI471566562, GI392570497, GI336375423, GI342887383, GI302675837, GI403412898, GI346979623, GI393243817, GI50980922, GI429856489, GI302885243, GI50980920, GI402220822, GI119484188, GI336384853, GI50980814, GI395327133, GI407921652, GI403417250, GI395333241, GI50980916, GI157674373, GI336372105, GI389743154, GI390598972, GI170099628, GI46126507, GI50980918, GI409076933, GI475675010, GI429850133, GI426195279, GI408391526, GI380481283, GI50980914, GI449544581, GI346970758, GI451847000, GI361124441, GI409048565, GI395329450, GI452002698, GI477527980, GI115386538, GI449542872, GI390598040, GI302403881, GI398395223, GI449295152, GI361129867, GI389628216, GI46121949, GI408391130, GI409045849, GI342872438, GI406859506, GI402079797, GI452980716, GI393212779, GI403420153, GI310795966, GI299748721, GI367039407, GI390598898, GI189192086, GI408392461, GI46139961, GI353237496, GI406867787, GI121700448, GI330920776, GI396501117, GI393212304, GI471897438, GI159130218, GI70992963, GI477517573, GI330944461, GI119473893, GI477593444, GI451856188, GI471572208, GI169600747, GI119473383, GI342877339, GI302887372, GI389643896, GI302890289, GI471879149, GI429848762, GI169784774, GI406701640, GI115397337, GI121712210, GI367023388, GI401881295, GI238508000, GI171682982, GI367040823, GI402079610, GI336372104, GI67515463, GI402219043, GI378733150, GI477532665, GI353237498, GI302881468, GI477521642, GI408398452, GI380482112, GI380491182, GI393241491, GI46114604, GI83768524, GI340946132, GI392594043, GI46139085, GI391864453, GI398388786, GI408398213, GI238490288, GI353234628, GI475673276, GI46126477, GI408391512, GI477523847, GI342889863, GI302679092, GI429848658, GI475666583, GI477531560, GI449540330, GI358386965, GI342876695, GI255954603, GI302880307, GI342879157, GI477511570, GI402221884, GI477509075, GI452003196, GI310797035, GI393244761, GI477517292, GI170098821, GI392594044, GI154297060, GI70985968, GI242772225, GI426199525, GI409078516, GI429856851, GI402224495, GI440471626, GI477528319, GI391865969, GI336370919, GI310794698, GI302410075, GI212529706, GI409048830, GI408398456, GI302684805, GI393213085, GI346980084, GI346974165, GI358398653, GI392568136, GI302416575, GI367039713, GI242820800, GI336383675, GI402224782, GI320589783, GI302900235, GI317431855, GI353237497, GI395332594, GI408393532, GI443921814, GI189209525, GI46126625, GI212541650, GI342873777, GI477520190, GI342882753, GI395329777, GI302886316, GI46115532, GI475674542, GI353234629, GI169615919, GI477513409, GI408395147, GI449549369, GI475673984, GI409050432, GI336373956, GI255941274, GI342873441, GI402222263, GI443917241, GI302418580, GI393241388, GI242787981, GI353242496, GI320584092, GI409079438, GI169865238, GI426192620, GI389749836, GI475675183, GI86196491, GI392586908, GI46139335, GI50426457, GI440472215, GI449302102, GI212534032, GI440639149, GI393233992, GI380477434, GI392594946, GI452987659, GI402222514, GI146422137, GI238494754, GI302917301, GI336262574, GI475675239, GI429853891, GI169777579, GI347829750, GI429855681, GI407919583, GI302888323, GI477511581, GI398411145, GI344233577, GI402221284, GI429859607, GI389646653, GI302887434, GI440482625, GI190348766, GI146412796, GI353239284, GI389647635, GI86196013, GI67902250, GI169859598, GI380489737, GI429849376, GI477532141, GI134119066, GI408392325, GI380492851, GI380485843, GI302881155, GI336465735, GI350287441, GI429858924, GI115491233, GI164424491, GI471564797, GI378725745, GI346978042, GI345566254, GI429856885, GI302415056, GI402219282, GI145248423, GI350639100, GI452002162, GI342882290, GI344304410, GI358370507, GI317034943, GI169594826, GI302901784, GI350632927, GI452001921, GI67524313, GI407916978, GI477533791, GI294659451, GI477523640, GI429847594, GI389624925, GI350630030, GI46103327, GI425767943, GI429863729, GI405123292, GI358374365, GI429852368, GI459366747, GI340519452, GI350639301, GI407923780, GI317451460, GI380488960, GI260951447, GI477535671, GI358393072, GI389637768, GI58260536, GI134117103, GI358385446, GI255730163, GI145235529, GI402220490, GI342890350, GI440470256, GI477511506, GI308198145, GI310791878, GI126273966, GI391873356, GI46114596, GI171691520, GI380486599, GI260951445, GI402076217, GI429862052, GI310795192, GI146421205, GI169785253, GI190346119, GI302883799, GI475674623, GI477533270, GI302882471, GI402080455, GI317031224, GI406861400, GI322697407, GI85094247, GI336467806, GI406607550, GI238506229, GI126132458, GI367033975, GI126273939, GI302884874, GI396464906, GI475674549, GI322711180, GI134077570, GI477512227, GI477515015, GI429851103, GI336471923, GI358383783, GI342878508, GI342876702, GI119494457, GI321265766, GI380095555, GI477511576, GI396475175, GI408396504, GI302898747, GI475670215, GI402076475, GI150865436, GI344229190, GI342883283, GI58262550, GI346976696, GI255940738, GI475675360, GI477513860, GI119473356, GI477523296, GI302883821, GI336270802, GI396493052, GI310800862, GI317451430, GI477516994, GI380493642, GI85085012, GI367039241, GI116200915, GI336266077, GI46138341, GI302913423, GI471562806, GI477526206, GI358376032, GI212538607, GI403418185, GI119473409, GI46125945, GI367026193, GI406701892, GI402216469, GI342873809, GI475672478, GI134081460, GI169774135, GI475677330, GI121700434, GI452979822, GI347828193, GI406859968, GI340939620, GI342889050, GI477509642, GI255931303, GI451854957, GI238497377, GI452001121, GI477514839, GI126138322, GI121700751, GI83771606, GI171677314, GI406607553, GI475674291, GI402219269, GI70996500, GI408388106, GI477527586, GI159130224, GI342883062, GI70992951, GI115391487, GI46102882, GI46114928, GI408389965, GI342875112, GI459367863, GI385301207, GI302415575, GI119494209, GI119482834, GI344229911, GI346977093, GI429860850, GI406607552, GI342876303, GI358394391, GI242792392, GI342872176, GI242799333, GI330907139, GI302886675, GI429857088, GI346321540, GI449299447, homologs thereof, and orthologs thereof.

In some embodiments, the xylodextrin transporter polypeptide contains an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of the CDT-2 polypeptide from *Neurospora crassa* (NCU08114)(SEQ ID NO: 1).

Xylodextrin transporter polypeptides of the present disclosure may be endogenously present in a cell, or they may be recombinantly expressed in a cell of the present disclosure. In certain embodiments, recombinant xylodextrin transporter polypeptides of the present disclosure include, for example, mutant xylodextrin transporter polypeptides containing one or more mutations that increase the specificity, function, and/or activity of the xylodextrin transporter. In some embodiments, recombinant xylodextrin transporter polypeptides of the present disclosure may have one or more additional transporter activities, such as glucose, cellulose, or cellodextrin transporter activity. Accordingly, in certain embodiments, mutant xylodextrin transporter polypeptides of the present disclosure preferentially transport xylodextrins. That is, mutant xylodextrin transporter polypeptides of the present disclosure may have a higher specificity for xylodextrins as compared to corresponding xylodextrin transporters that lack the one or more mutations. Recombinant xylodextrin transporters containing one or more mutations can be produced by mutating a polynucleotide encoding a xylodextrin transporter of the present disclosure. In some embodiments, a mutant xylodextrin transporter of the present disclosure may contain one or more mutations that include, for example, point mutations, missense mutations, substitution mutations, frameshift mutations, insertion mutations, duplication mutations, amplification mutations, translocation mutations, or inversion mutations that results in a xylodextrin transporter with increased specificity for xylodextrins and/or increased xylodextrin transport activity, as compared to a corresponding xylodextrin transporter that does not contain the one or more mutations.

In some embodiments, the xylodextrin transporter is a functional fragment that maintains the ability to transport one or more xylodextrin molecules from outside of the cell to the inside of the cell and/or from inside of the cell to outside of the cell. Functional fragments of a xylodextrin transporter polypeptide may include, for example, polypeptides having at least 10, at least 12, at least 14, at least 16, at least 18, or at least 20 consecutive amino acids of a xylodextrin transporter polypeptide.

Xylose Reductase Polypeptides

Host cells of the present disclosure contain a xylose reductase polypeptide. Xylose reductase polypeptides are generally understood to be enzymes that catalyze the following reaction: xylose+NAD(P)H+H+=xylitol+NAD(P)+ (E.C. 1.1.1.21). However, Applicants have shown that xylose reductase polypeptides may also act on xylodextrins as substrates to catalyze the following general reaction: xylooligosaccharide+NAD(P)H+H+=xylosyl-xylitol oligomer+NAD(P)+. For example, when the substrate is xylobiose, a xylose reductase polypeptide of the present disclosure may catalyze the following reaction: xylobiose+NAD(P)H+H+=xylosyl-xylitol+NAD(P)+. Xylose reductase polypeptides that are able to act on xylodextrin substrates to catalyze the production of xylosyl-xylitol oligomers have xylodextrin reductase activity. Accordingly, xylose reductase polypeptides for use in the methods of the present disclosure have xylodextrin reductase activity.

Xylose reductase activity and xylodextrin reductase activity of xylose reductase polypeptides of the present disclosure are not necessarily mutually exclusive. For example, xylose reductase polypeptides of the present disclosure may have both xylose reductase activity and xylodextrin reductase activity.

Various xylose reductase polypeptides are known in the art and may be used in the methods of the present disclosure. Further, putative xylose reductase polypeptides can be screened for xylose reductase activity and/or xylodextrin reductase activity by any suitable method known in the art such as, for example, those disclosed herein.

Suitable xylose reductases may be obtained from any microorganism capable of metabolizing xylose and/or xylodextrins. Examples of such microorganisms include, for example, *Pichia* sp., *Candida* sp., *Aspergillus* sp., and *Neurospora crassa*. Examples of suitable xylose reductase polypeptides may include, for example, the xylose reductase from *S. stipitis*, XYL1 (GenBank: ADQ89193.1), and the xylose reductase from *Neurospora crassa*, XYR-1 (NCU08384). Other xylose reductases may include, for example, AAF86345.1, AAO91803.1, AEY80024.1, AAC25601.1, and AAW34373.1. Each sequence associated with the foregoing accession numbers is incorporated herein by reference. Other xylose reductases are well-known to those skilled in the art and may be used in the host cells of the present disclosure.

In some embodiments, the xylose reductase polypeptide contains an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of the XYL1 polypeptide from *S. stipitis* (GenBank: ADQ89193.1)(SEQ ID NO: 2). In some embodiments, the xylose reductase polypeptide contains an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of the XYR-1 polypeptide from *N. crassa* (NCU08384)(SEQ ID NO: 3).

Xylose reductase polypeptides of the present disclosure may be endogenously present in a cell, or they may be recombinantly expressed in a cell of the present disclosure. In certain embodiments, recombinant xylose reductase polypeptides of the present disclosure include, for example, mutant xylose reductase polypeptides containing one or more mutations that increase the specificity, function, and/or activity of the xylose reductase. For example, in certain embodiments, mutant or endogenous xylose reductase polypeptides of the present disclosure preferentially act on xylooligosaccharide substrates. That is, mutant xylose reductase polypeptides of the present disclosure may have a higher specificity for xylodextrins as compared to corresponding xylose reductase polypeptides that lack the one or more mutations. Recombinant xylose reductase polypeptides containing one or more mutations can be produced by mutating a polynucleotide encoding a xylose reductase of the present disclosure. In some embodiments, a mutant xylose reductase polypeptide of the present disclosure may contain one or more mutations that include, for example, point mutations, missense mutations, substitution mutations, frameshift mutations, insertion mutations, duplication mutations, amplification mutations, translocation mutations, or inversion mutations that results in a xylose reductase polypeptide with increased specificity for xylodextrins (as opposed to xylose) as compared to a corresponding xylose reductase polypeptide that does not contain the one or more mutations.

In some embodiments, the xylose reductase polypeptide is a functional fragment that maintains catalytic activity (e.g. the ability to convert a xylodextrin substrate into a xylosyl-xylitol oligomer). Functional fragments of a xylose reductase polypeptide may include, for example, polypeptides having at least 10, at least 12, at least 14, at least 16, at least 18, or at least 20 consecutive amino acids of a xylose reductase polypeptide.

β-Xylosidase Polypeptides

In some aspects, host cells of the present disclosure have reduced activity of one or more β-xylosidase polypeptides as compared to a corresponding wild-type cell. β-xylosidase polypeptides are generally understood to be 1,4-β-D-xylan xylohydrolase (E.C. 3.2.1.37) enzymes that catalyze the hydrolysis of terminal non-reducing D-xylose residues from xylodextrins with the release of D-xylose. However, Applicants have also shown that β-xylosidases may possess activity to act on xylosyl-xylitol oligomer substrates. β-xylosidase polypeptides that are able to catalyze the hydrolysis of xylosyl-xylitol oligomers have xylosyl-xylitol hydrolase activity. Accordingly, β-xylosidase polypeptides for use in the methods of the present disclosure have xylosyl-xylitol hydrolase activity.

β-xylosidase activity and xylosyl-xylitol hydrolase activity of β-xylosidase polypeptides of the present disclosure are not necessarily mutually exclusive. For example, β-xylosidase polypeptides of the present disclosure may have both β-xylosidase activity and xylosyl-xylitol hydrolase activity.

Various β-xylosidase polypeptides are known in the art and may be targeted for a reduction in activity according to the methods of the present disclosure. β-xylosidases of the present disclosure having reduced activity may include, for example, members of the GH3 family of glycoside hydrolases, members of the GH39 family of glycoside hydrolases, members of the GH43 family of glycoside hydrolases, members of the GH52 family of glycoside hydrolases, and members of the GH54 family of glycoside hydrolases.

Proteins, such as GH3, GH39 GH43, GH52, or GH54 glycoside hydrolases, can be screened for xylosyl-xylitol hydrolase activity by any suitable method known in the art including, for example, those disclosed herein. In some embodiments, β-xylosidase polypeptides having xylosyl-xylitol hydrolase activity are targeted for a reduction in activity.

In some embodiments, a β-xylosidase having reduced activity contains an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of the GH43-7 polypeptide from *Neurospora crassa* (NCU09652)(SEQ ID NO: 4).

In some embodiments, a β-xylosidase having reduced activity contains an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of the β-xylosidase polypeptide from *Bacillus subtilis* (AAB41091.1)(SEQ ID NO: 5).

In some embodiments, a β-xylosidase having reduced activity contains an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of the β-xylosidase polypeptide from *Escherichia coli* (WP_000406872.1)(SEQ ID NO: 6).

Xylitol Dehydrogenase Polypeptides

In some aspects, host cells of the present disclosure have reduced activity of one or more xylitol dehydrogenase (XDH) polypeptides as compared to a corresponding wild-type cell. Xylitol dehydrogenases generally refer to an enzyme (E.C. 1.1.1.9) that catalyzes the following reaction: xylitol+NAD+=D-xylulose+NADH+H+. Other names for xylitol dehydrogenase include, for example, "D-xylulose reductase," "NAD-dependent xylitol dehydrogenase," "erythritol dehydrogenase," "2,3-cis-polyol(DPN) dehydrogenase (C3-5)," "pentitol-DPN dehydrogenase," "xylitol-2-dehydrogenase," and "xylitol: NAD+2-oxidoreductase (D-xylulose-forming)."

Various xylitol dehydrogenase (XDH) polypeptides are known in the art and may be targeted for a reduction in activity according to the methods of the present disclosure. Xylitol dehydrogenase polypeptides of the present disclosure having reduced activity may include, for example, xylitol dehydrogenases from *Pichia* sp., *Candida* sp., *Aspergillus* sp., and *Neurospora crassa*. In some embodiments, the xylitol dehydrogenase is the *Pichia stipitis* xylitol dehydrogenase XYL2 (Accession Number P22144). In some embodiments, xylitol dehydrogenases include, for example, the polypeptides of NCBI Accession numbers: ACI01079.1, XP_456938.2, and ABA39795.1. Each sequence associated with the foregoing accession numbers is incorporated herein by reference. Other xylitol dehydrogenases are well-known to those skilled in the art.

In some embodiments, xylitol dehydrogenase polypeptides of the present disclosure having reduced activity contain an amino acid sequence having at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to the amino acid sequence of the xylitol dehydrogenase protein P22144.

Polynucleotides Encoding Polypeptides

The present disclosure further relates to polynucleotides that encode polypeptides of the present disclosure. Polynucleotides that encode a polypeptide are also referred to herein as "genes." For example, polynucleotides encoding any known or putative xylodextrin transporter, xylose reductase, β-xylosidase, or xylitol dehydrogenase polypeptide as described herein are provided. Methods for determining the relationship between a polypeptide and a polynucleotide that encodes the polypeptide are well-known to one of skill in the art. Similarly, methods of determining the polypeptide sequence encoded by a polynucleotide sequence are well-known to one of skill in the art.

As used herein, the terms "polynucleotide," nucleic acid sequence," "nucleic acid," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications. As used herein, the symbols for nucleotides and polynucleotides are those recommended by the IUPAC-IUB Commission of Biochemical Nomenclature.

Sequences of the polynucleotides of the present disclosure may be prepared by various suitable methods known in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteucci et al., (1980) Tetrahedron Lett 21:719-722; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired polynucleotide sequence from the gel via techniques known to those of ordinary skill in the art, such as utilization of polymerase chain reactions (PCR; e.g., U.S. Pat. No. 4,683,195).

Methods of Identifying Sequence Similarity

Various methods are known to those of skill in the art for identifying similar (e.g. homologs, orthologs, paralogs, etc.) polypeptide and/or polynucleotide sequences, including phylogenetic methods, sequence similarity analysis, and hybridization methods.

Phylogenetic trees may be created for a gene family by using a program such as CLUSTAL (Thompson et al. Nucleic Acids Res. 22: 4673-4680 (1994); Higgins et al. *Methods Enzymol* 266: 383-402 (1996)) or MEGA (Tamura et al. *Mol. Biol. & Evo.* 24:1596-1599 (2007)). Once an initial tree for genes from one species is created, potential orthologous sequences can be placed in the phylogenetic tree and their relationships to genes from the species of interest can be determined. Evolutionary relationships may also be inferred using the Neighbor-Joining method (Saitou and Nei, *Mol. Biol. & Evo.* 4:406-425 (1987)). Homologous sequences may also be identified by a reciprocal BLAST strategy. Evolutionary distances may be computed using the Poisson correction method (Zuckerkandl and Pauling, pp. 97-166 in *Evolving Genes and Proteins*, edited by V. Bryson and H. J. Vogel. Academic Press, New York (1965)).

In addition, evolutionary information may be used to predict gene function. Functional predictions of genes can be greatly improved by focusing on how genes became similar in sequence (i.e. by evolutionary processes) rather than on the sequence similarity itself (Eisen, *Genome Res*. 8: 163-167 (1998)). Many specific examples exist in which gene function has been shown to correlate well with gene phylogeny (Eisen, *Genome Res.* 8: 163-167 (1998)). By using a phylogenetic analysis, one skilled in the art would recognize that the ability to deduce similar functions conferred by closely-related polypeptides is predictable.

When a group of related sequences are analyzed using a phylogenetic program such as CLUSTAL, closely related sequences typically cluster together or in the same clade (a group of similar genes). Groups of similar genes can also be identified with pair-wise BLAST analysis (Feng and Doolittle, *J. Mol. Evol.* 25: 351-360 (1987)). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount, Bioinformatics: Sequence and Genome Analysis Cold Spring Harbor Laboratory Press, Cold Spring Harbor, N.Y., page 543 (2001)).

To find sequences that are homologous to a reference sequence, BLAST nucleotide searches can be performed with the BLASTN program, score=100, wordlength=12, to obtain nucleotide sequences homologous to a nucleotide sequence encoding a protein of the disclosure. BLAST protein searches can be performed with the BLASTX program, score=50, wordlength=3, to obtain amino acid sequences homologous to a protein or polypeptide of the disclosure. To obtain gapped alignments for comparison purposes, Gapped BLAST (in BLAST 2.0) can be utilized as described in Altschul et al. (1997) *Nucleic Acids Res.*

25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTX for proteins) can be used.

Methods for the alignment of sequences and for the analysis of similarity and identity of polypeptide and polynucleotide sequences are well-known in the art.

As used herein "sequence identity" refers to the percentage of residues that are identical in the same positions in the sequences being analyzed. As used herein "sequence similarity" refers to the percentage of residues that have similar biophysical/biochemical characteristics in the same positions (e.g. charge, size, hydrophobicity) in the sequences being analyzed.

Methods of alignment of sequences for comparison are well-known in the art, including manual alignment and computer assisted sequence alignment and analysis. This latter approach is a preferred approach in the present disclosure, due to the increased throughput afforded by computer assisted methods. As noted below, a variety of computer programs for performing sequence alignment are available, or can be produced by one of skill.

The determination of percent sequence identity and/or similarity between any two sequences can be accomplished using a mathematical algorithm. Examples of such mathematical algorithms are the algorithm of Myers and Miller, CABIOS 4:11-17 (1988); the local homology algorithm of Smith et al., Adv. Appl. Math. 2:482 (1981); the homology alignment algorithm of Needleman and Wunsch, *J. Mol. Biol.* 48:443-453 (1970); the search-for-similarity-method of Pearson and Lipman, *Proc. Natl. Acad. Sci.* 85:2444-2448 (1988); the algorithm of Karlin and Altschul, *Proc. Natl. Acad. Sci. USA* 87:2264-2268 (1990), modified as in Karlin and Altschul, *Proc. Natl. Acad. Sci. USA* 90:5873-5877 (1993).

Computer implementations of these mathematical algorithms can be utilized for comparison of sequences to determine sequence identity and/or similarity. Such implementations include, for example: CLUSTAL in the PC/Gene program (available from Intelligenetics, Mountain View, Calif.); the AlignX program, version10.3.0 (Invitrogen, Carlsbad, Calif.) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. *Gene* 73:237-244 (1988); Higgins et al. *CABIOS* 5:151-153 (1989); Corpet et al., *Nucleic Acids Res.* 16:10881-90 (1988); Huang et al. *CABIOS* 8:155-65 (1992); and Pearson et al., *Meth. Mol. Biol.* 24:307-331 (1994). The BLAST programs of Altschul et al. *J. Mol. Biol.* 215:403-410 (1990) are based on the algorithm of Karlin and Altschul (1990) supra.

Polynucleotides homologous to a reference sequence can be identified by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in references cited below (e.g., Sambrook et al., Molecular Cloning: A Laboratory Manual, 2nd Ed., Vol. 1-3, Cold Spring Harbor Laboratory, Cold Spring Harbor, N.Y. ("Sambrook") (1989); Berger and Kimmel, Guide to Molecular Cloning Techniques, Methods in Enzymology, vol. 152 Academic Press, Inc., San Diego, Calif. ("Berger and Kimmel") (1987); and Anderson and Young, "Quantitative Filter Hybridisation." In: Hames and Higgins, ed., Nucleic Acid Hybridisation, A Practical Approach. Oxford, TRL Press, 73-111 (1985)).

Encompassed by the disclosure are polynucleotide sequences that are capable of hybridizing to the disclosed polynucleotide sequences and fragments thereof under various conditions of stringency (see, for example, Wahl and Berger, *Methods Enzymol.* 152: 399-407 (1987); and Kimmel, *Methods Enzymo.* 152: 507-511, (1987)). Full length cDNA, homologs, orthologs, and paralogs of polynucleotides of the present disclosure may be identified and isolated using well-known polynucleotide hybridization methods.

Further, genes and proteins that may be used in the present disclosure include genes encoding conservatively modified variants and proteins that are conservatively modified variants of those genes and proteins described herein. "Conservatively modified variants" as used herein include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, alleles, and various substitutions of the disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Vectors for Expressing Polynucleotides

Each polynucleotide of the present disclosure may be incorporated into an expression vector. "Expression vector" or "vector" refers to a compound and/or composition that transduces, transforms, or infects a host cell, thereby causing the cell to express polynucleotides and/or proteins other than those native to the cell, or in a manner not native to the cell. An "expression vector" contains a sequence of polynucleotides (ordinarily RNA or DNA) to be expressed by the host cell. Optionally, the expression vector also includes materials to aid in achieving entry of the polynucleotide into the host cell, such as a virus, liposome, protein coating, or the like. The expression vectors contemplated for use in the present disclosure include those into which a polynucleotide sequence can be inserted, along with any preferred or required operational elements. Further, the expression vector must be one that can be transferred into a host cell and replicated therein. Preferred expression vectors are plasmids, particularly those with restriction sites that have been well-documented and that contain the operational elements preferred or required for transcription of the polynucleotide sequence. Such plasmids, as well as other expression vectors, are well-known in the art.

Incorporation of the individual polynucleotides may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a polynucleotide having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired polynucleotide are often cleaved with the same restriction enzyme, thereby assuring that the ends of the expression vector and the ends of the polynucleotide are complementary to each other. In addition, DNA linkers may be used to facilitate linking of polynucleotide sequences into an expression vector.

A series of individual polynucleotides can also be combined by utilizing methods that are known in the art (e.g., U.S. Pat. No. 4,683,195). For example, each of the desired polynucleotides can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other. Extension of this overlap by DNA polymerase produces a molecule in which the original sequences are "spliced" together. In this way, a series of individual polynucleotides may be "spliced" together and subsequently transduced into a host cell simultaneously. Thus, expression of each of the plurality of polynucleotides is affected.

Individual polynucleotides, or "spliced" polynucleotides, are then incorporated into an expression vector. The present disclosure is not limited with respect to the process by which the polynucleotide is incorporated into the expression vector. Those of ordinary skill in the art are familiar with the necessary steps for incorporating a polynucleotide into an expression vector. A typical expression vector contains the desired polynucleotide preceded by one or more regulatory regions, along with a ribosome binding site, e.g., a nucleotide sequence that is 3-9 nucleotides in length and located 3-11 nucleotides upstream of the initiation codon in E. coli. See Shine and Dalgarno (1975) Nature 254(5495):34-38 and Steitz (1979) Biological Regulation and Development (ed. Goldberger, R. F.), 1:349-399 (Plenum, New York).

The term "operably linked" as used herein refers to a configuration in which a control sequence is placed at an appropriate position relative to the coding sequence of the DNA sequence or polynucleotide such that the control sequence directs the expression of a polypeptide.

Regulatory regions include, for example, those regions that contain a promoter and an operator. A promoter is operably linked to the desired polynucleotide, thereby initiating transcription of the polynucleotide via an RNA polymerase enzyme. An operator is a sequence of polynucleotides adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter (see de Boer et al., (1983) Proc Natl Acad Sci USA 80(1):21-25).

Methods of producing host cells of the disclosure may include the introduction or transfer of the expression vectors containing recombinant nucleic acids of the disclosure into the host cell. Such methods for transferring expression vectors into host cells are well-known to those of ordinary skill in the art. For example, one method for transforming cells with an expression vector involves a calcium chloride treatment where the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host cell. Cells also may be transformed through the use of spheroplasts (Schweizer, M, Proc. Natl. Acad. Sci., 78: 5086-5090 (1981). Also, microinjection of the nucleic acid sequences provides the ability to transfect host cells. Other means, such as lipid complexes, liposomes, and dendrimers, may also be employed. Those of ordinary skill in the art can transfect a host cell with a desired sequence using these or other methods.

In some cases, cells are prepared as protoplasts or spheroplasts prior to transformation. Protoplasts or spheroplasts may be prepared, for example, by treating a cell having a cell wall with enzymes to degrade the cell wall. Fungal cells may be treated, for example, with chitinase.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Furthermore, a single vector or plasmid or two or more vectors or plasmids that together contain the total DNA to be introduced into the genome of the host, or a transposon may be used.

The vectors preferably contain one or more selectable markers which permit easy selection of transformed host cells. A selectable marker is a gene the product of which provides, for example, biocide or viral resistance, resistance to heavy metals, prototrophy to auxotrophs, and the like. Selection of bacterial cells may be based upon antimicrobial resistance that has been conferred by genes such as the amp, gpt, neo, and hyg genes.

Selectable markers for use in fungal host cells may include, for example, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof.

The vectors may contain an element(s) that permits integration of the vector into the host's genome or autonomous replication of the vector in the cell independent of the genome.

For integration into the host genome, the vector may rely on the gene's sequence or any other element of the vector for integration of the vector into the genome by homologous or nonhomologous recombination. Alternatively, the vector may contain additional nucleotide sequences for directing integration by homologous recombination into the genome of the host. The additional nucleotide sequences enable the vector to be integrated into the host genome at a precise location(s) in the chromosome(s). To increase the likelihood of integration at a precise location, the integrational elements should contain a sufficient number of nucleic acids, such as 100 to 10,000 base pairs, 400 to 10,000 base pairs, or 800 to 10,000 base pairs, which are highly homologous with the corresponding target sequence to enhance the probability of homologous recombination. The integrational elements may be any sequence that is homologous with the target sequence in the genome of the host. Furthermore, the integrational elements may be non-encoding or encoding nucleotide sequences. On the other hand, the vector may be integrated into the genome of the host by non-homologous recombination.

For autonomous replication, the vector may further contain an origin of replication enabling the vector to replicate autonomously in the host in question. The origin of replication may be any plasmid replicator mediating autonomous replication which functions in a cell. The term "origin of replication" or "plasmid replicator" is defined herein as a sequence that enables a plasmid or vector to replicate in vivo.

Various promoters for regulation of expression of a recombinant nucleic acid of the disclosure in a vector are well-known in the art and include, for example, constitutive promoters and inducible promoters. Promoters are described, for example, in Sambrook, et al. Molecular Cloning: A Laboratory Manual, 3rd edition, Cold Spring Harbor Laboratory Press, (2001). Promoter can be viral, bacterial, fungal, mammalian, or plant promoters. Additionally, promoters can be constitutive promoters, inducible promoters, environmentally regulated promoters, or developmentally regulated promoters. Examples of suitable promoters for regulating recombinant nucleic acid of the disclosure may include, for example, the *N. crassa* ccg-1 constitutive promoter, which is responsive to the *N. crassa* circadian rhythm and nutrient conditions; the *N. crassa* gpd-1 (glyceraldehyde 3-phosphate dehydrogenase-1) strong constitutive promoter; the *N. crassa* vvd (light) inducible promoter; the *N. crassa* qa-2 (quinic acid) inducible promoter; the *Aspergillus nidulans* gpdA promoter; the *Aspergillus nidulans* trpC constitutive promoter; the *N. crassa* tef-1 (transcription elongation factor) highly constitutive promoter; and the *N. crassa* xlr-1 (XlnR homolog) promoter, which is used frequently in *Aspergillus* species. In some embodiments, expression of a recombinant polypeptide of the disclosure is under the control of a heterologous promoter.

More than one copy of a gene may be inserted into the host to increase production of the gene product. An increase in the copy number of the gene can be obtained by integrating at least one additional copy of the gene into the host genome or by including an amplifiable selectable marker gene with the nucleotide sequence where cells containing amplified copies of the selectable marker gene, and thereby additional copies of the gene, can be selected for by cultivating the cells in the presence of the appropriate selectable agent.

The procedures used to ligate the elements described above to construct the recombinant expression vectors of the present disclosure are well-known to one skilled in the art (see, e.g., Sambrook et al., 1989, supra). When only a single expression vector is used (without the addition of an intermediate), the vector will contain all of the nucleic acid sequences necessary.

Host Cells of the Disclosure

Host cells of the present disclosure are capable of producing xylosyl-xylitol oligomers from a xylodextrin substrate. "Host cell" and "host microorganism" are used interchangeably herein and refer to a living biological cell that may be used in the methods of the present disclosure. In some embodiments, host cells may be transformed via insertion of one or more recombinant nucleic acids, such as DNA or RNA. Such recombinant nucleic acids can be in one or more expression vectors. Thus, a host microorganism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

Various prokaryotic or eukaryotic host cells may be used in the present disclosure so long as it remains viable after being transformed with a sequence of nucleic acids. Preferably, the host cell is not adversely affected by the transduction of the necessary nucleic acid sequences, the subsequent expression of the proteins or the resulting intermediates. Suitable eukaryotic cells include, for example, fungal, plant, insect and mammalian cells.

In some embodiments, the host is a fungal strain. "Fungi" as used herein includes, for example, the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In certain embodiments, the fungal cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of the present disclosure, yeast shall be defined as described in Biology and Activities of Yeast (Skinner, F. A., Passmore, S. M., and Davenport, R. R., eds, Soc. App. Bacteriol. Symposium Series No. 9, 1980).

In some embodiments, the yeast host is a *Candida, Hansenula, Issatchenkia, Kluyveromyces, Pichia, Saccharomyces, Schizosaccharomyces*, or *Yarrowia* strain. In other embodiments, the yeast host is a *Saccharomyces carlsbergensis* (Todkar, 2010), *Saccharomyces cerevisiae* (Duarte et al., 2009), *Saccharomyces diastaticus, Saccharomyces douglasii, Saccharomyces kluyveri, Saccharomyces norbensis, Saccharomyces monacensis* (GB-Analysts Reports, 2008), *Saccharomyces bayanus* (Kristen Publicover, 2010), *Saccharomyces pastorianus* (Nakao et al., 2007), *Saccharomyces pombe* (Mousdale, 2008), or *Saccharomyces oviformis* strain. In yet other embodiments, the yeast host is *Kluyveromyces lactis* (O. W. Merten, 2001), *Kluyveromyces fragilis* (Pestal et al., 2006; Siso, 1996), *Kluyveromyces marxiamus* (K. Kourkoutas et al., 2008), *Pichia stipitis* (Almeida et al., 2008), *Candida shehatae* (Ayhan Demirbas, 2003), or *Candida tropicalis* (Jamai et al., 2006). In other embodiments, the yeast host may be *Yarrowia lipolytica* (Biryukova E. N., 2009), Brettanomyces custersii (Spindler D. D. et al., 1992), or *Zygosaccharomyces* roux (Chaabane et al., 2006). In some embodiments, the yeast cell is *S. cerevisiae*.

In other embodiments, the fungal host is a filamentous fungal strain. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In some embodiments, the filamentous fungal host is, for example, an *Acremonium, Aspergillus, Fusarium, Humicola, Mucor, Myceliophthora, Neurospora, Penicillium, Scytalidium, Thielavia, Tolypocladium,* or *Trichoderma* strain. In some embodiments, the host cell is *Neurospora crassa*.

In some embodiments, the filamentous fungal host is an *Aspergillus awamori, Aspergillus foetidus, Aspergillus japonicus, Aspergillus nidulans, Aspergillus niger,* or *Aspergillus oryzae* strain. In still other embodiments, the filamentous fungal host is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* strain. In some embodiments, the filamentous fungal host is a *Humicola insolens, Humicola lanuginosa, Mucor miehei, Myceliophthora thermophila, Penicillium purpurogenum, Scytalidium thermophilum, Sporotrichum* thermophile (Topakas et al., 2003), or *Thielavia terrestris* strain. In some embodiments, the filamentous fungal host is a *Trichoderma harzianum, Trichoderma koningii, Trichoderma longibrachiatum, Trichoderma reesei,* or *Trichoderma viride* strain.

In some embodiments, the host cell is prokaryotic, and in certain embodiments, the prokaryotes are *E. coli* (Dien, B. S. et al., 2003; Yomano, L. P. et al., 1998; Moniruzzaman et al., 1996), *Bacillus subtilis* (Susana Romero et al., 2007), *Zymomonas mobilis* (B. S. Dien et al., 2003; Weuster Botz, 1993; Alterthum and Ingram, 1989), *Thermoanaerobacterium* saccharolyticum (Marietta Smith, 2009), or *Klebsiella oxytoca* (Dien, B. S. et al., 2003; Zhou et al., 2001; Brooks and Ingram, 1995). In other embodiments, the prokaryotic host cells are *Carboxydocella* sp. (Dominik et al., 2007), *Corynebacterium glutamicum* (Masayuki Inui, et al., 2004), Enterobacteriaceae (Ingram et al., 1995), *Erwinia chrysanthemi* (Zhou and Ingram, 2000; Zhou et al., 2001), *Lactobacillus* sp. (McCaskey, T. A., et al., 1994), *Pediococcus acidilactici* (Zhou, S. et al., 2003), *Rhodopseudomonas capsulata* (X. Y. Shi et al., 2004), *Streptococcus lactis* (J. C. Tang et al., 1988), *Vibrio* fumissii (L. P. Wackett, 2010), *Vibrio fumissii* M1 (Park et al., 2001), *Caldicellulosiruptor saccharolyticus* (Z. Kadar et al., 2004), or *Xanthomonas campestris* (S. T. Yang et al., 1987). In other embodiments, the host cells are cyanobacteria. Additional examples of bacterial host cells include, for example, those species assigned to the *Escherichia, Enterobacter, Azotobacter, Erwinia, Bacillus, Pseudomonas, Klebsiella, Proteus, Salmonella, Serratia, Shigella, Rhizobia, Vitreoscilla, Synechococcus, Synechocystis,* and *Paracoccus* taxonomical classes.

The host cells of the present disclosure may be genetically modified in that recombinant nucleic acids have been introduced into the host cells, and as such the genetically modified host cells do not occur in nature. A suitable host cell of the present disclosure is one capable of expressing one or more nucleic acid constructs encoding one or more proteins for different functions.

"Recombinant nucleic acid" or "heterologous nucleic acid" or "recombinant polynucleotide" as used herein refers to a polymer of nucleic acids where at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids contains two or more subsequences that are not found in the same relationship to each other in nature. For example, regarding instance (c), a recombinant nucleic acid sequence will have two or more sequences from unrelated genes arranged to make a new functional nucleic acid. Specifically, the present disclosure describes the introduction of an expression vector into a host cell, where the expression vector contains a nucleic acid sequence coding for a protein that is not normally found in a host cell or contains a nucleic acid coding for a protein that is normally found in a cell but is under the control of different regulatory sequences. With reference to the host cell's genome, then, the nucleic acid sequence that codes for the protein is recombinant. A protein that is referred to as recombinant generally implies that it is encoded by a recombinant nucleic acid sequence in the host cell.

A "recombinant" polypeptide, protein, or enzyme of the present disclosure, is a polypeptide, protein, or enzyme that is encoded by a "recombinant nucleic acid" or "heterologous nucleic acid" or "recombinant polynucleotide."

In some embodiments, the genes encoding the desired proteins in the host cell may be heterologous to the host cell or these genes may be endogenous to the host cell but are operatively linked to heterologous promoters and/or control regions which result in the higher expression of the gene(s) in the host cell. In certain embodiments, the host cell does not naturally produce the desired proteins, and contains heterologous nucleic acid constructs capable of expressing one or more genes necessary for producing those molecules.

"Endogenous" as used herein with reference to a nucleic acid molecule or polypeptide and a particular cell or microorganism refers to a nucleic acid sequence or polypeptide that is in the cell and was not introduced into the cell using recombinant engineering techniques; for example, a gene that was present in the cell when the cell was originally isolated from nature. In some embodiments, certain polypeptides of the present disclosure are endogenously present in host cells used in methods of producing xylosyl-xylitol oligomers.

"Genetically engineered" or "genetically modified" refers to any recombinant DNA or RNA method used to create a prokaryotic or eukaryotic host cell that expresses a protein at elevated levels, at lowered levels, or in a non-endogenous (e.g. mutated) form. In other words, the host cell has been transfected, transformed, or transduced with a recombinant polynucleotide molecule, and thereby been altered so as to cause the cell to alter expression of a desired protein. Methods and vectors for genetically engineering host cells are well known in the art; for example various techniques are illustrated in Current Protocols in Molecular Biology, Ausubel et al., eds. (Wiley & Sons, New York, 1988, and quarterly updates). Genetically engineering techniques include, for example, expression vectors, and targeted homologous recombination and gene activation (see, for example, U.S. Pat. No. 5,272,071).

Methods of Modifying Polypeptide Activity

Host cells of the present disclosure may have modified polypeptide activity as compared to a corresponding control cell, such as a corresponding wild-type cell, to facilitate and/or increase the production of xylosyl-xylitol oligomers. Polypeptide activity may be modified such that one or more polypeptides of the present disclosure have increased activity or decreased activity. In some embodiments, a host cell may have one or more polypeptides with increased activity as well as one or more polypeptides with decreased activity. Methods of modifying (e.g. increasing and/or decreasing) the activity of one or more polypeptides of the present disclosure are well-known in the art and are described herein.

Decreased Polypeptide Activity

Host cells of the present disclosure may contain one or more polypeptides with decreased/reduced activity as compared to a corresponding control cell, such as a wild-type cell. For example, one or more β-xylosidase proteins, such as those having xylosyl-xylitol hydrolase activity for example, or one or more xylitol dehydrogenase enzymes, may have decreased activity in a host cell as compared to a corresponding control cell. Methods of decreasing the expression, abundance, and/or activity of a polypeptide are well-known in the art and are described herein.

In some embodiments, decreasing activity of a polypeptide involves overexpressing a polypeptide that is an inhibitor of the polypeptide. Host cells may overexpress an inhibitor that inhibits the expression and/or activity of one or more proteins that acts to prevent the production and/or accumulation of xylosyl-xylitol oligomers, such as, for example, β-xylosidases that have xylosyl-xylitol hydrolase activity.

In some embodiments, decreasing the activity of a polypeptide such as, for example, one or more β-xylosidases and/or one or more xylitol dehydrogenases, involves decreasing the expression of a nucleic acid encoding the polypeptide. Decreasing the expression of a nucleic acid may be accomplished by introducing a genetic mutation into a target nucleic acid. Mutagenesis approaches may be used to disrupt or "knockout" the expression of a target gene by generating mutations. In some embodiments, the mutagenesis results in a partial deletion of the target gene. In other embodiments, the mutagenesis results in a complete deletion of the target gene. Methods of mutagenizing microorganisms are well known in the art and include, for example, random mutagenesis and site-directed mutagenesis to induce mutations. Examples of methods of random mutagenesis include, for example, chemical mutagenesis (e.g., using ethane methyl sulfonate), insertional mutagenesis, and irradiation. In some embodiments, host cells of the present disclosure have a mutation is one or more β-xylosidase polypeptides and/or one or more xylitol dehydrogenase polypeptides.

One method for reducing or inhibiting the expression of a target gene is by genetically modifying the target gene and introducing it into the genome of a host cell to replace the wild-type version of the gene by homologous recombination (for example, as described in U.S. Pat. No. 6,924,146).

Another method for reducing or inhibiting the expression of a target gene is by insertion mutagenesis using the T-DNA of *Agrobacterium tumefaciens*, or transposons (see Winkler et al., Methods Mol. Biol. 82:129-136, 1989, and Martienssen Proc. Natl. Acad. Sci. 95:2021-2026, 1998). After generating the insertion mutants, the mutants can be screened to identify those containing the insertion in a target gene. Methods to disrupt a target gene by insertional mutagenesis are described in for example, U.S. Pat. No. 5,792,633. Methods to disrupt a target gene by transposon mutagenesis are described in for example, U.S. Pat. No. 6,207,384.

A further method to disrupt a target gene is by use of the cre-lox system (for example, as described in U.S. Pat. No. 4,959,317).

Another method to disrupt a target gene is by use of PCR mutagenesis (for example, as described in U.S. Pat. No. 7,501,275).

Endogenous gene expression may also be reduced or inhibited by means of RNA interference (RNAi), which uses a double-stranded RNA having a sequence identical or similar to the sequence of the target gene. RNAi may include the use of micro RNA, such as artificial miRNA, to suppress expression of a gene.

RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA.

Thus, in some embodiments, reduction or inhibition of gene expression is achieved using RNAi techniques. For example, to achieve reduction or inhibition of the expression of a DNA encoding a protein using RNAi, a double-stranded RNA having the sequence of a DNA encoding the protein, or a substantially similar sequence thereof (including those engineered not to translate the protein) or fragment thereof, is introduced into a host cell of interest. As used herein, RNAi and dsRNA both refer to gene-specific silencing that is induced by the introduction of a double-stranded RNA molecule, see e.g., U.S. Pat. Nos. 6,506,559 and 6,573,099, and includes reference to a molecule that has a region that is double-stranded, e.g., a short hairpin RNA molecule. The resulting cells may then be screened for a phenotype associated with the reduced expression of the target gene, e.g., reduced cellulase expression, and/or by monitoring steady-state RNA levels for transcripts of the target gene. Although the sequences used for RNAi need not be completely identical to the target gene, they may be at least 70%, 80%, 90%, 91%, 92%, 93%, 94%, 95%, 96%, 97%, 98%, 99%, or more identical to the target gene sequence. See, e.g., U.S. Patent Application Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Application Publication No. 2003/0221211.

The RNAi nucleic acids may encompass the full-length target RNA or may correspond to a fragment of the target RNA. In some cases, the fragment will have fewer than 100, 200, 300, 400, or 500 nucleotides corresponding to the target sequence. In addition, in some aspects, these fragments are at least, e.g., 50, 100, 150, 200, or more nucleotides in length. Interfering RNAs may be designed based on short duplexes (i.e., short regions of double-stranded sequences). Typically, the short duplex is at least about 15, 20, or 25-50 nucleotides in length (e.g., each complementary sequence of the double stranded RNA is 15-50 nucleotides in length), often about 20-30 nucleotides, e.g., 20, 21, 22, 23, 24, 25, 26, 27, 28, 29, or 30 nucleotides in length. In some cases, fragments for use in RNAi will correspond to regions of a target protein that do not occur in other proteins in the organism or that have little similarity to other transcripts in the organism, e.g., selected by comparison to sequences in analyzing publicly-available sequence databases. Similarly, RNAi fragments may be selected for similarity or identity with a conserved sequence of a gene family of interest, such as those described herein, so that the RNAi targets multiple different gene transcripts containing the conserved sequence.

RNAi may be introduced into a host cell as part of a larger DNA construct. Often, such constructs allow stable expression of the RNAi in cells after introduction, e.g., by integration of the construct into the host genome. Thus, expression vectors that continually express RNAi in cells transfected with the vectors may be employed for this disclosure. For example, vectors that express small hairpin or stem-loop structure RNAs, or precursors to microRNA, which get processed in vivo into small RNAi molecules capable of carrying out gene-specific silencing (Brummelkamp et al, Science 296:550-553, (2002); and Paddison, et al., Genes & Dev. 16:948-958, (2002)) can be used. Post-transcriptional gene silencing by double-stranded RNA is discussed in further detail by Hammond et al., Nature Rev Gen 2: 110-119, (2001); Fire et al., Nature 391: 806-811, (1998); and Timmons and Fire, Nature 395: 854, (1998).

Methods for selection and design of sequences that generate RNAi are well-known in the art (e.g. U.S. Pat. Nos. 6,506,559; 6,511,824; and 6,489,127).

A reduction or inhibition of gene expression in a host cell of a target gene may also be obtained by introducing into host cells antisense constructs based on a target gene nucleic acid sequence. For antisense suppression, a target sequence is arranged in reverse orientation relative to the promoter sequence in the expression vector. The introduced sequence need not be a full length cDNA or gene, and need not be identical to the target cDNA or a gene found in the cell to be transformed. Generally, however, where the introduced sequence is of shorter length, a higher degree of homology to the native target sequence is used to achieve effective antisense suppression. In some aspects, the introduced antisense sequence in the vector will be at least 30 nucleotides in length, and improved antisense suppression will typically be observed as the length of the antisense sequence increases. In some aspects, the length of the antisense sequence in the vector will be greater than 100 nucleotides. Transcription of an antisense construct as described results in the production of RNA molecules that are the reverse complement of mRNA molecules transcribed from an endogenous target gene. Suppression of a target gene expression can also be achieved using a ribozyme. The production and use of ribozymes are disclosed in U.S. Pat. Nos. 4,987,071 and 5,543,508.

Expression cassettes containing nucleic acids that encode target gene expression inhibitors, e.g., an antisense or siRNA, can be constructed using methods well known in the art. Constructs include regulatory elements, including promoters and other sequences for expression and selection of cells that express the construct. Typically, fungal and/or bacterial transformation vectors include one or more cloned coding sequences (genomic or cDNA) under the transcriptional control of 5' and 3' regulatory sequences and a dominant selectable marker. Such transformation vectors typically also contain a promoter (e.g., a regulatory region controlling inducible or constitutive, environmentally- or developmentally-regulated expression), a transcription initiation start site, an RNA processing signal (such as intron splice sites), a transcription termination site, and/or a polyadenylation signal.

In certain embodiments, a portion of the target nucleic acid may be modified, such as the region encoding the catalytic domain, the coding region, or a control sequence required for expression of the coding region. Such a control sequence of the gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification may include, for example, a leader sequence, a propeptide sequence, a signal sequence, a transcription terminator, and a transcriptional activator.

Increased Polypeptide Activity

Host cells of the present disclosure may contain one or more polypeptides with increased expression and/or activity as compared to a corresponding control cell, such as a corresponding wild type cell. In some embodiments, host cells of the disclosure contain a recombinant nucleic acid encoding a recombinant polypeptide. In certain embodiments, the recombinant nucleic acid is mis-expressed in the host cell (e.g., constitutively expressed, inducibly expressed, etc.) such that mis-expression results in increased polypeptide activity as compared to a corresponding control cell. In some embodiments, a host cell that contains a recombinant nucleic acid encoding a recombinant polypeptide contains a greater amount of the polypeptide than a corresponding control cell that does not contain the corresponding recombinant nucleic acid. When a protein or nucleic acid is produced or maintained in a host cell at an amount greater than normal, the protein or nucleic acid is "overexpressed." In some embodiments, host cells of the disclosure overexpress a polypeptide such as, for example, a xylodextrin transporter or a xylose reductase polypeptide. Host cells may overexpress one or more polypeptides such that the activity of one or more of these proteins is increased in the host cell as compared to a corresponding control cell. The corresponding control cell may be, for example, a cell that does not overexpress one or more of the polypeptides overexpressed in the host cell, such as a wild-type cell. Various control cells will be readily apparent to one of skill in the art.

Various methods of increasing the expression of a polypeptide are known in the art. For example, other genetic regions involved in controlling expression of the nucleic acid encoding the polypeptide, such as an enhancer sequence, may be modified such that expression of the nucleic acid is increased. The level of expression of a nucleic acid may be assessed by measuring the level of mRNA encoded by the gene, and/or by measuring the level or activity of the polypeptide encoded by the nucleic acid.

In some embodiments, host cells overexpress a polypeptide that is an activator of one or more polypeptides, such as xylodextrin transporters and/or xylose reductases. Overexpression of an activator polypeptide may lead to increased abundance and activity of the polypeptide activated by the activator. The activator may increase expression of the target polypeptide. The activator may increase activity of the target polypeptide.

Increasing the abundance of a polypeptide of the disclosure such as, for example, a xylodextrin transporter and/or a xylose reductase, to increase polypeptide activity may be achieved by overexpressing the polypeptide. Other methods of increasing abundance of a polypeptide are known in the art. For example, decreasing degradation of the polypeptide by cellular degradation machinery, such as the proteasome, may increase the stability and the abundance of the polypeptide. The polypeptides may be genetically modified such that they have increased resistance to cellular proteolysis, but exhibit no change in molecular activity. Polypeptides that are inhibitors of cellular factors involved in the degradation of one or more polypeptides that are targeted for increased activity may be introduced into host cells to increase abundance of the one or more polypeptides. Further, host cells may be treated with chemical inhibitors of the proteasome, such as cycloheximide, to increase the abundance of one or more polypeptides of the disclosure.

Methods of Producing Xylosyl-Xylitol Oligomers

The present disclosure relates to methods of producing xylosyl-xylitol oligomers. Host cells of the present disclosure that are used to produce xylosyl-xylitol oligomers possess a xylodextrin transporter and a xylose reductase. Various xylodextrin transporters may be used insofar as they are able to transport one or more xylodextrins into the host cell. Various xylose reductase polypeptides may be used insofar as they are able act on a xylodextrin substrate to convert a xylodextrin into a xylosyl-xylitol oligomer. Additionally, the activity of one or more β-xylosidase proteins may be reduced in the cell insofar as a particular β-xylosidase possesses xylosyl-xylitol hydrolase activity. Proteins having xylosyl-xylitol hydrolase activity will hydrolyze xylosyl-xylitol oligomers and prevent their accumulation in host cells, and thus xylosyl-xylitol hydrolase activity should be reduced or removed from the cell. Further, the activity of one or more xylitol dehydrogenases may be reduced in the cell.

In order to produce xylosyl-xylitol oligomers, host cells of the present disclosure should be cultured in a growth medium that contains xylodextrins or a source of xylodextrins. Various xylodextrins may be used including, for example, xylobiose (2 xylose monomers), xylotriose (3 xylose monomers), xylotetraose (4 xylose monomers), xylopentaose (5 xylose monomers), and xylohexaose (6 xylose monomers). Selection of xylodextrins may be tailored to the specific xylodextrin transporter(s) present in the host cell, as different xylodextrin transporters may have different affinities for and/or capability of transporting different types and lengths of xylodextrins, as will be appreciated by one of skill in the art. Xylodextrins may be purchased commercially or they may be derived from a source of xylodextrins.

Sources of xylodextrins are well-known in the art and are described herein. For example, the source of xylodextrins may be a material that contains xylodextrins or whose breakdown releases xylodextrins. As used herein, a "xylodextrin-containing material" is any material that contains or is capable of generating xylodextrins, including biomass, such as biomass containing plant material. Biomass suitable for use with the currently disclosed methods include various xylodextrin-containing materials such as, for example, *Miscanthus*, switchgrass, cord grass, rye grass, reed canary grass, elephant grass, common reed, wheat straw, barley straw, canola straw, oat straw, corn stover, soybean stover, oat hulls, sorghum, rice hulls, rye hulls, wheat hulls, sugarcane bagasse, copra meal, copra pellets, palm kernel meal, corn fiber, Distillers Dried Grains with Solubles (DDGS), Blue Stem, corncobs, pine wood, birch wood, willow wood, aspen wood, poplar wood, energy cane, waste paper, sawdust, forestry wastes, municipal solid waste, waste paper, crop residues, other grasses, and other woods. The source of xylodextrins may require a pre-treatment to generate and/or liberate xylodextrins such as, for example, treatment with high temperature or pressure. Such treatments are well-known to those skilled in the art. In embodiments where host cells are grown on certain sources of xylodextrins, such as lignocellulosic biomass, host cells that are capable of liberating xylodextrins from the biomass should be used. Exemplary cells will be readily apparent to one of skill in the art.

Host cells of the present disclosure should be cultured under suitable conditions such that the host cells produce xylosyl-xylitol oligomers from xylodextrin substrates. Growth media used in the methods of the present disclosure to culture host cells should contain a suitable carbon source. "Carbon source" generally refers to a substrate or compound suitable to be used as a source of carbon for cell growth. Carbon sources may be in various forms such as, for example, polymers, carbohydrates, acids, alcohols, aldehydes, ketones, amino acids, peptides, etc. These include, for example, various monosaccharides, oligosaccharides, polysaccharides, a biomass polymer such as cellulose or hemicellulose, xylose, arabinose, disaccharides, such as sucrose, saturated or unsaturated fatty acids, succinate, lactate, acetate, ethanol, etc., or mixtures thereof. In addition to an appropriate carbon source, culture media may contain suitable minerals, salts, cofactors, buffers and other components, known to those skilled in the art, suitable for the growth of the cultures and promotion of the pathways involved in the production of xylosyl-xylitol oligomers. Standard culture environments for host cells, such as microorganisms, are well-known in the art and are described herein. In some embodiments, host cells of the present disclosure are cultured aerobically or microaerobically.

The methods of the present disclosure may result in the production and accumulation of xylosyl-xylitol oligomers (xylosyl$_n$-xylitol) in host cells. Various xylosyl-xylitol oligomers may be produced by host cells including, for example, xylosyl-xylitol, xylosyl-xylosyl-xylitol (xylosyl$_2$-xylitol), xylosyl-xylosyl-xylosyl-xylitol (xylosyl$_3$-xylitol), xylosyl-xylosyl-xylosyl-xylosyl-xylitol (xylosyl$_4$-xylitol), xylosyl-xylosyl-xylosyl-xylosyl-xylosyl-xylitol (xylosyl$_5$-xylitol), and xylosyl-xylosyl-xylosyl-xylosyl-xylosyl-xylosyl-xylitol (xylosyl$_6$-xylitol). The particular xylosyl-xylitol oligomer produced may depend on a variety of factors, such as the particular xylodextrin substrate and the particular activity of a given xylose reductase when acting on a xylodextrin substrate, as will be readily appreciated by one of skill in the art.

In some embodiments, the methods of the present disclosure involve host cells having an increased xylosyl-xylitol oligomer production rate as compared to a corresponding control cell. Host cells having an increased xylosyl-xylitol oligomer production rate may be those having decreased activity of one or more β-xylosidases and/or one or more xylitol dehydrogenases, and/or increased expression or activity of one or more xylodextrin transporters and/or xylose reductases. The rate of xylosyl-xylitol oligomer production in host cells of the present disclosure may be at least 0.1-fold, at least 0.2-fold, at least 0.3-fold, at least 0.4-fold, at least 0.5-fold, at least 0.6-fold, at least 0.7-fold, at least 0.8-fold, at least 0.9-fold, at least 1-fold, at least 1.25 fold, at least 1.5-fold, at least 1.75-fold, at least 2-fold, at least 2.25-fold, at least 2.5-fold, at least 2.75-fold, at least 3-fold, at least 3.25-fold, at least 3.5-fold, at least 3.75-fold, at least 4-fold, at least 4.25-fold, at least 4.5-fold, at least 4.75-fold, at least 5-fold, at least 5.25-fold, at least 5.5-fold, at least 5.75-fold, at least 6-fold, at least 7-fold, at least 8-fold, at least 9-fold, at least 10-fold, at least 20-fold, or at least 30-fold or more higher than the xylosyl-xylitol oligomer production rate of a corresponding control cell such as, for example, a wild type cell or a cell not having modified polypeptide activity. In some embodiments, the corresponding control cell does not accumulate any xylosyl-xylitol oligomers. Control cells may be unable to produce xylosylxylitol oligomers because, for example, the control cells do not contain the molecular machinery required to produce xylosyl-xylitol oligomers. Exemplary cells that cannot produce xylosyl-xylitol oligomers may include, for example, cells which do not possess a xylodextrin transporter and/or a xylose reductase polypeptide. Control cells may be unable to accumulate xylosyl-xylitol oligomers because, for example, the control cells possess molecular machinery which hydrolyzes xylosyl-xylitol oligomers, such as β-xylosidases having xylosyl-xylitol hydrolase activity.

In some embodiments, the methods of the present disclosure involve host cells having a decreased rate of xylosyl-xylitol oligomer consumption as compared to a corresponding control cell. Host cells having a decreased rate of xylosyl-xylitol oligomer consumption may be those having decreased activity of one or more β-xylosidases which exhibit xylosyl-xylitol hydrolase activity, and/or one or more xylitol dehydrogenases. The hydrolysis of a xylosyl-xylitol oligomer by a host cell of the present disclosure may be reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or by about 100% as compared to a corresponding control cell such as, for example, a wild type cell or a cell not having modified polypeptide activity. In some embodiments, the consumption of a xylosyl-xylitol oligomer by a host cell of the present disclosure is reduced by about 100% as compared to a corresponding control cell.

Methods of measuring the accumulation, production, and/or consumption/degradation/hydrolysis rate of a xylosyl-xylitol oligomer by a host cell or a population of cells are well-known in the art and are described herein. For example, determining the xylosyl-xylitol oligomer consumption/degradation rate of a cell or cell population in culture may involve allowing cells to grow in medium containing xylodextrins and measuring the depletion of the xylodextrins from the growth medium over time at specified time points and determining the slope of the resulting plotted line to determine xylodextrin consumption/degradation rate (e.g. xylobiose/L/h). Similarly, determining xylosyl-xylitol oligomer accumulation or production may involve culturing a cell or population of cells in a medium containing xylodextrins and measuring the production of a xylosyl-xylitol oligomer from the xylodextrin over time at specified time points.

In some embodiments, after a host cell of the present disclosure has produced a xylosyl-xylitol oligomer, the xylosyl-xylitol oligomer may be precipitated, removed, or substantially purified from the culture media. Methods of substantially purifying xylosyl-xylitol oligomers from culture media will be apparent to one of skill in the art and are described herein. For example, various column chromatography techniques may be used to purify a xylosyl-xylitol oligomer from culture media.

Compositions Containing Xylosyl-Xylitol Oligomers

The present disclosure further provides compositions containing a xylosyl-xylitol oligomer. Various compositions including a xylosyl-xylitol oligomer produced according to the methods of the present disclosure are described herein and will be apparent to one of skill in the art. For example, in some embodiments where a xylosyl-xylitol oligomer is purified from a medium, the xylosyl-xylitol oligomer may be included in a composition to create a xylosyl-xylitol-containing composition. In other embodiments, the composition containing a xylosyl-xylitol oligomer may contain such oligomers that have not been substantially purified from growth media. For example, compositions containing media containing xylosyl-xylitol oligomers produced by host cells of the present disclosure may be produced. Host cells may be removed from the media such that the composition contains cell-free growth media and xylosyl-xylitol oligomers produced by the host cells.

EXAMPLES

The following Examples are offered for illustrative purposes and to aid one of skill in better understanding the various embodiments of the disclosure. The following Examples are not intended to limit the scope of the present disclosure in any way.

Example 1: Xylosyl-Xylitol Oligomers and their Microbial and Enzymatic Production This Example demonstrates that xylosyl-xylitol oligomers are produced by a *Saccharomyces cerevisiae* strain engineered to contain a xylodextrin transport and utilization pathway. Xylodextrins transported into the engineered strain expressing a heterologous xylodextrin transporter were converted to the major products xylosyl-xylitol and xylosyl-xylosyl-xylitol by a heterologous xylose reductase. This work thus demonstrates the establishment of a biological platform for the bioproduction of xylosyl-xylitol oligomers. A summary of the biological pathway leading to the production of xylosyl-xylitol oligomers from a xylodextrin substrate is presented in FIG. 13A.

Materials and Methods

*Neurospora crassa* Strains

*N. crassa* strains obtained from the Fungal Genetics Stock Center (FGSC) (McCluskey et al., 2003) include the WT (FGSC 2489), and deletion strains for the two oligosaccharide transporters: NCU00801 (FGSC 16575) and NCU08114 (FGSC 17868).

Heterologous Expression Plasmids and Yeast Strains

Template gDNA from the *N. crassa* WT strain (FGSC 2489) and from the *S. cerevisiae* S288C strain was extracted (the world wide web dot fgsc.net/fgn35/lee35.pdf) and Harju et al. Open reading frames (ORFs) of the β-xylosidase genes NCU01900 and NCU09652 (GH43-2 and GH43-7, respectively) were amplified from the *N. crassa* gDNA template. The accession number for *N. crassa* CDT-2 at NCBI is XP_963873.1. The accession number for *S. stipitis* xylose reductase at GenBank is ADQ89193.1. For biochemical assays, each ORF was fused with a C-terminal His$_6$-tag and flanked with the *S. cerevisiae* P$_{TEF1}$ promoter and CYC1 transcriptional terminator in the 2μ yeast plasmid pRS423 backbone. Plasmid pRS426_NCU08114 was described previously (Galazka et al., 2010). Plasmid pLNL78 containing the xylose utilization pathway (xylose reductase, xylitol dehydrogenase, and xylulose kinase) from *Scheffersomyces stipitis* was obtained from the lab of John Dueber (Latimer et al., submitted). Plasmid pXD2, a single-plasmid form of the xylodextrin pathway, was constructed by integrating NCU08114 and NCU01900 expression cassettes into pLNL78, using the In-Fusion cloning kit (Clontech). Plasmid pXD8.4, derived from plasmid pRS316 (Sikorski et al., 1989) was used to express CDT-2 and GH43-2, each from the P$_{CCW12}$ promoter. Plasmid pXD8.6 was derived from pXD8.4 by replacing the GH43-2 ORF with the ORF for GH43-7. pXD8.7 contained all three expression cassettes (CDT-2, GH43-2 and GH43-7) using the P$_{CCW12}$ promoter for each. *S. cerevisiae* strain D452-2 (MATa leu2 his3 ura3 can1) (Kurtzman et al., 1994) and SR8U (the uracil autotrophic version of the evolved xylose fast utilization strain SR8) (Kim et al., 2013) were used as recipient strains for the yeast experiments. The ORF for *N. crassa* xylose reductase (XYR-1, NcXR) was amplified from *N. crassa* gDNA and the introns were removed by overlapping PCR. The ORF for *S. stipitis* xylose reductase (SsXR) was amplified from pLNL78. Each xylose reductase ORF was fused to a C-terminal $His_6$-tag and flanked with the *S. cerevisiae* $P_{CCW12}$ promoter and CYC1 transcriptional terminator, and inserted into plasmid pRS316.

Yeast Cell-Based Xylodextrin Uptake Assay

*S. cerevisiae* was grown in an optimized minimum medium (oMM) lacking uracil into late log phase. The oMM contained 1.7 g/L YNB (Sigma, Y1251), 2-fold appropriate CSM dropout mixture, 10 g/L $(NH_4)_2SO_4$, 1 g/L $MgSO_4.7H_2O$, 6 g/L $KH_2PO_4$, 100 mg/L adenine hemisulfate, 10 mg/L inositol, 100 mg/L glutamic acid, 20 mg/L lysine, 375 mg/L serine and 100 mM 4-morpholineethanesulfonic acid (MES), pH 6.0 (Lin et al., submitted). Cells were then harvested and washed three times with assay buffer (5 mM MES, 100 mM NaCl, pH 6.0) and resuspended to a final $OD_{600}$ of 40. Substrate stocks were prepared in the same assay buffer at a concentration of 200 µM. Transport assays were initiated by mixing equal volumes of the cell suspension and the substrate stock. Reactions were incubated at 30° C. with continuous shaking for 30 minutes. Samples were centrifuged at 14,000 rpm at 4° C. for 5 minutes to remove yeast cells. 400 µL of each sample supernatant was transferred to an HPLC vial containing 100 µL of 0.5 M NaOH, and the concentration of the remaining substrate was measured by HPAEC as described below.

Enzyme Purification

*S. cerevisiae* strains transformed with enzyme-expression plasmids were grown in oMM lacking histidine until late log phase before harvesting by centrifugation. Yeast cell pellets were resuspended in a buffer containing 50 mM Tris-HCl, 100 mM NaCl, 0.5 mM DTT, pH 7.4 and protease inhibitor cocktail (Pierce). Cells were lysed with an Avestin homogenizer, and the clarified supernatant was loaded onto a HisTrap column (GE Healthcare). His-tagged enzymes were purified with an imidazole gradient, buffer-exchanged into 20 mM Tris-HCl, 100 mM NaCl, pH 7.4, and concentrated to 5 mg/mL.

Enzyme Assays

For the β-xylosidase assay of GH43-2 with xylodextrins, 0.5 µM of purified enzyme was incubated with 0.1% in-house prepared xylodextrin or 1 mM xylobiose (Megazyme) in 1×PBS at 30° C. Reactions were sampled at 30 min and quenched by adding 5 volumes of 0.1 mM NaOH. The products were analyzed by HPAEC as described below. For pH profiling, acetate buffer at pH 4.0, 4.5, 5.0, 5.5, 6.0, and phosphate buffer at 6.5, 7.0, 7.5, 8 were added at a concentration of 0.1 M. For the β-xylosidase assay of GH43-2 and GH43-7 with xylosyl-xylitol, 10 µM of purified enzyme was incubated with 4.5 mM xylosyl-xylitol and 0.5 mM xylobiose in 20 mM MES buffer, pH=7.0, and 1 mM $CaCl_2$ at 30° C. Reactions were sampled at 3 hours and quenched by heating at 99° C. for 10 min. The products were analyzed by ion-exclusion HPLC as described below.

For the xylose reductase assays of *S. stipitis* XR and *N. crassa* XR, 1 µM of purified enzyme was incubated with 0.06% xylodextrin and 2 mM NADPH in 1×PBS at 30° C. Reactions were sampled at 30 min and quenched by heating at 99° C. for 10 min. The products were analyzed by LC-QToF as described below.

Oligosaccharide Preparation

Xylodextrin was purchased from Cascade Analytical Reagents and Biochemicals or prepared according to published procedures (Akpinar et al., 2009) with slight modifications. In brief, 20 g beechwood xylan (Sigma-Aldrich) was fully suspended in 1000 mL water, to which 13.6 mL 18.4 M $H_2SO_4$ was added. The mixture was incubated in a 150° C. oil bath with continuous stirring. After 30 min, the reaction was poured into a 2 L plastic container on ice, with stirring to allow it to cool. Following this, 0.25 mol $CaCO_3$ was slowly added to neutralize the pH and precipitate sulfate. The supernatant was filtered and concentrated on a rotary evaporator at 50° C. to dryness. The in-house prepared xylodextrin contained about 30% xylose monomers and 70% oligomers. To obtain a larger fraction of short chain xylodextrin, the commercial xylodextrin was dissolved to 20% w/v and incubated with 2 mg/mL xylanase at 37° C. for 48 hours. Heat deactivation and filtration were performed before use.

$(Xylosyl)_n$-Xylitol Purification

Xylosyl-xylitol and oligomers were purified from the culture broth of strain SR8 containing plasmids pXD8.4 in xylodextrin medium. 50 mL of culture supernatant was concentrated on a rotary evaporator at 50° C. to about 5 mL. The filtered sample was loaded on an XK 16/70 column (GE Healthcare) packed with Supelclean™ ENVI-Carb™ (Sigma-Aldrich), a solid phase extraction cartridge, mounted on an AKTA Purifier (GE Healthcare). The column was eluted with a gradient of acetonitrile at a flow rate of 3.0 mL/min at room temperature. Purified fractions, verified by LC-MS, were pooled and concentrated. The final product, containing 90% of xylosyl-xylitol and 10% xylobiose, was used as the substrate for enzyme assays and as an HPLC calibration standard.

Yeast Cultures with Xylodextrins

Yeast strains were pre-grown aerobically overnight in oMM medium containing 2% glucose, washed 3 times with water, and resuspended in oMM medium. For aerobic growth, strains were inoculated at a starting $OD_{600}$ of 1.0 or 20 in 50 mL oMM medium with 4% w/v xylodextrins and cultivated in 250 mL Erlenmeyer flasks covered with 4 layers of miracle cloth, shaking at 220 rpm. For microaerobic growth, strains were inoculated at a starting $OD_{600}$ of 80 in 50 mL oMM medium with 4% w/v xylodextrins and cultivated in 125 mL Erlenmeyer flasks covered with 4 layers of miracle cloth, shaking at 100 rpm. At the indicated time points, 0.8 mL samples were removed and pelleted. 20 µL supernatants were analyzed by ion-exclusion HPLC to determine xylose, xylitol, glycerol, and ethanol concentrations. 25 µL of 1:200 diluted or 2 µL of 1:100 diluted supernatant was analyzed by HPAEC or LC-QToF, respectively, to determine xylodextrin concentrations.

Figure 13B:
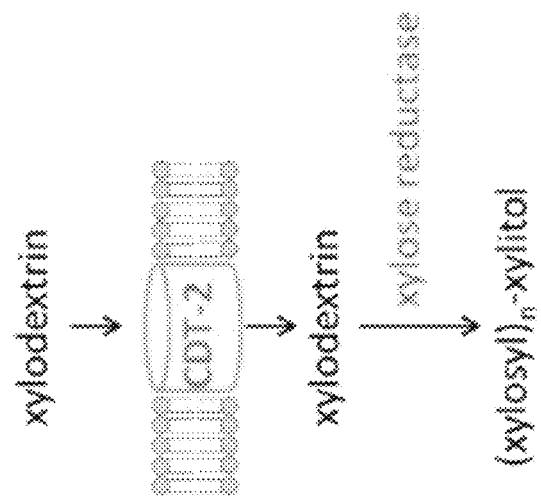
FIG. 13A-FIG. 13B illustrates yeast conversion of xylodextrin to xylosyl-xylitol (xlt2) and xylosyl-xylosyl-xylitol (xlt3).

For FIG. 13B specifically, the engineered yeast strain was pre-grown aerobically overnight in oMM medium containing 2% glucose, washed 3 times with water, and resuspended in oMM medium. The oMM media without a carbon source contained, per liter, 1.7 g YNB (lacking ammonium sulfate, Sigma, Y1251), 2-fold appropriate CSM dropout mixture (MP Biomedicals), 10 g (NH4)2SO4, 1 g MgSO4.7H2O, 6 g KH2PO4, 100 mg adenine hemisulfate, 10 mg inositol, as well as an additional 100 mg glutamic acid, 20 mg lysine and 375 mg serine. Then the cells were inoculated at a starting $OD_{600}$ of 80 in 50 mL oMM medium with 4% w/v xylodextrins and cultivated in a 125 mL Erlenmeyer flask covered with 4 layers of miracle cloth, shaking at 100 rpm. At the indicated time points, 0.8 mL samples were removed and pelleted. The XOS consumption and $(xylosyl)_n$-xylitol production were identified and measured by LC-QToF mass spectrometry. At the end of day 5, 93% of xylobiose and 71% of xylotriose were consumed. The yield of xylosyl-xylitol and xylosyl-xylosyl-xylitol were 90% and 54%, respectively.

Ion-Exclusion HPLC Analysis

Ion-exclusion HPLC was performed on a Shimadzu Prominence HPLC equipped with a refractive index detector. Samples were resolved on an ion exclusion column (Aminex HPX-87H Column, 300×7.8 mm, Bio-Rad) using a mobile phase of 0.01 N $H_2SO_4$ at a flow rate of 0.6 mL/min at 50° C.

HPACE Analysis

HPAEC analysis was performed on a ICS-3000 HPLC (Thermo Fisher) using a CarboPac PA200 analytical column (150×3 mm) and a CarboPac PA200 guard column (3×30 mm) at 30° C. Following injection of 25 µL of diluted samples, elution was performed at 0.4 mL/min using 0.1 M NaOH in the mobile phase with sodium acetate gradients. For xylodextrin and xylosyl-xylitol separation, the acetate gradients were 0 mM for 1 min, increasing to 80 mM in 8 min, increasing to 300 mM in 1 min, keeping at 30 mM for 2 min, followed by re-equilibration at 0 mM for 3 min Carbohydrates were detected using pulsed amperometric detection (PAD) and peaks were analyzed and quantified using the Chromeleon software package.

Mass Spectrometric Analyses

All mass spectrometric analyses were performed on an Agilent 6520 Accurate-Mass Q-TOF coupled with an Agilent 1200 LC. Samples were resolved on a 100×7.8 mm Rezex RFQ-Fast Fruit H+8% column (Phenomenex) using a mobile phase of 0.5% formic acid at a flow rate of 0.3 mL/min at 55° C.

To determine the accurate masses of the unknown metabolites, 2 µL of 1:100 diluted yeast culture supernatant was analyzed by LC-QTOF. Nitrogen was used as the instrument gas. The source voltage (Vcap) was 3,000 V in negative ion mode, and the fragmentor was set to 100 V. The drying gas temperature was 300° C.; drying gas flow was 7 L/min; and nebulizer pressure was 45 psi. The ESI source used a separate nebulizer for the continuous, low-level introduction of reference mass compounds (112.985587, 1033.988109) to maintain mass axis calibration. Data was collected at an acquisition rate of 1 Hz from m/z 50 to 1100, and stored in centroid mode.

LC-MS/MS was performed to confirm the identity of xylosyl-xylitol and xylosyl-xylosyl-xylitol. The compound with a retention time (RT) of 5.8 min and m/z ratio of 283.103 and the compound with an RT of 4.7 min and m/z ratio of 415.15 were fragmented with collision energies of 10, 20 and 40 eV. MS/MS spectra were acquired, and the product ions were compared and matched to the calculated fragment ions generated by the Fragmentation Tools in ChemBioDraw Ultra v13.

To quantify the carbohydrates and carbohydrate derivatives in the culture, culture supernatants were diluted 100-fold in water and 2 µL was analyzed by LC-QToF. Spectra were imported to Qualitative Analysis module of Agilent MassHunter Workstation software using m/z and retention time values obtained from the calibration samples to search for the targeted ions in the data. These searches generated extracted ion chromatograms (EICs) based on the list of target compounds. Peaks were integrated and compared to the calibration curves to calculate the concentration. Calibration curves were calculated from the calibration samples, prepared in the same oMM medium as all the samples, and curve fitting for each compound resulted in fits with $R^2$ values of 0.999. 4-morpholineethanesulfonic acid (MES), the buffer compound in the oMM medium with constant concentration and not utilized by yeast, was used as an internal standard (IS) for concentration normalization.

Phylogenetic Analyses

Homologs of GH43-2 and GH43-7 were found with BLAST (Altschul et al., 1997) queries of the respective sequences against NCBI protein database. Representative sequences from diversified taxonomy were chosen and aligned with the MUSCLE algorithm (Edgar et al., 2004). A maximum likelihood phylogenetic tree was calculated based on the joined alignment with the Jones-Taylor-Thornton model by using software MEGA v6.05 (Tamura et al., 2013). The homology models of GH43-2 and GH43-7 were built with the Phyre2 server (Kelley et al., 2009).

Results

Applicants were interested in exploring biological methods of metabolizing xylodextrins. The biological production of biofuels and renewable chemicals from plant biomass requires an economic way to convert complex carbohydrate polymers from the plant cell wall into simple sugars that can be fermented by microbes (Carroll et al., 2009; Chundawat et al., 2011). In current industrial methods, the two major polysaccharides found in the plant cell wall, cellulose and hemicellulose (Somerville et al., 2004), are generally processed into monomers of glucose and xylose, respectively (Chundawat et al., 2011). However, in addition to harsh pretreatment of biomass, large quantities of cellulase and hemicellulase enzyme cocktails are required to release monosaccharides from plant cell walls, posing unsolved economic and logistical challenges (Chundawat et al., 2011; Himmel et al., 2007; Jarboe et al., 2010; Lynd et al., 2002). The bioethanol industry currently uses the yeast *Saccharomyces cerevisiae* to ferment sugars derived from cornstarch or sugarcane into ethanol (Hong et al., 2012), but *S. cerevisiae* requires substantial engineering to be able to ferment sugars derived from plant cell walls, such as cellobiose and xylose (Hong et al., 2012; Ha et al., 2011; Kuyper et al., 2005; Young et al., 2014; Jeffries et al., 2006).

Figure 12:
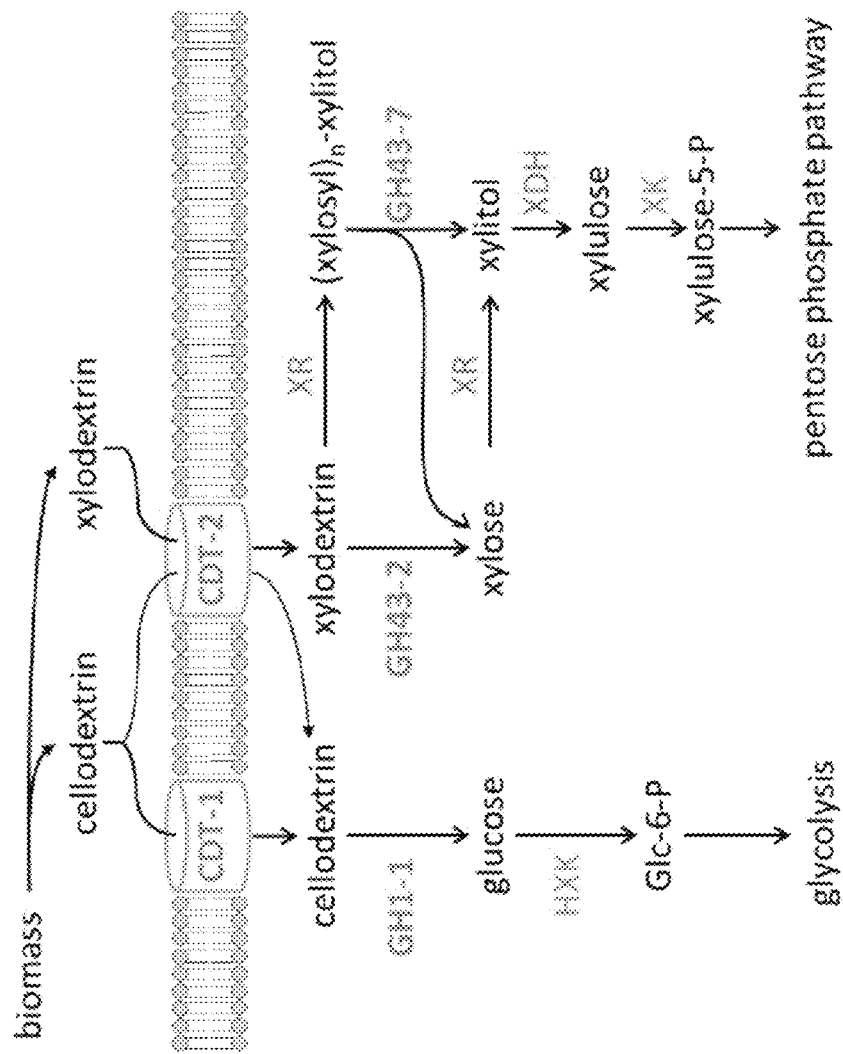
FIG. 12 illustrates two pathways of oligosaccharide consumption in *N. crassa* reconstituted in *S. cerevisiae*. Intracellular cellobiose utilization requires CDT-1 or CDT-2 along with β-glucosidase GH1-1 (Galazka et al., 2010), and enters glycolysis after phosphorylation by hexokinases (HXK) to form glucose-6-phosphate (Glc-6-P). Intracellular xylodextrin utilization also uses CDT-2, and requires the intracellular β-xylosidases GH43-2 and GH43-7. The resulting xylose can be assimilated through the pentose phosphate pathway which includes xylose/xylodextrin reductase (XR), xylitol dehydrogenase (XDH), and xylulokinase (XK).

In contrast to *S. cerevisiae*, many cellulolytic fungi including *Neurospora crassa* (Tian et al., 2009) grow well on both the cellulose and hemicellulose components of the plant cell wall. As can be seen in FIG. 12, a variety of molecular components are involved in the transport and utilization of cellulose and hemicellulose as carbon sources, including transporter proteins to transport cellodextrin and/or xylodextrin into the cell, intracellular β-glucosidases and β-xylosidases to hydrolyze the cellodextrins and xylodextrins, respectively, and various components that facilitate the utilization of these hydrolysis products as carbon sources. For xylose, which is a product of the hydrolysis of xylodextrins, xylose reductase (XR), xylitol dehydrogenase (XDH), and xylulokinase (XK) allow for the utilization of xylose.

As stated above, cellodextrins and xylodextrins derived from plant cell walls are not catabolized by wild-type *S. cerevisiae* (Galazka et al., 2010; Young et al., 2010; Matsushika et al., 2009). It was previously found that reconstitution of a cellodextrin transport and consumption pathway from *N. crassa* in *S. cerevisiae* enabled this yeast to ferment cellobiose (Galazka et al., 2010). Further, *S. cerevisiae* was previously engineered to consume xylose by introducing xylose isomerase (XI), or by introducing xylose reductase (XR) and xylitol dehydrogenase (XDH) (Jeffries et al., 2006; Matsushika et al., 2009). Applicants reasoned that expression of a functional xylodextrin transport and consumption system from *N. crassa* might further expand the capabilities of *S. cerevisiae* to utilize plant-derived xylodextrins as a source of carbon.

Construction of Xylodextrin Transport and Utilization Strain

Applicants were interested in constructing a functional xylodextrin transport and consumption system in *S. cerevisiae*, and began with investigating possible mechanisms of xylodextrin transport in *N. crassa*. Analysis of transcription profiling data (Tian et al., 2009) and growth phenotypes of *N. crassa* knockout strains led Applicants to identify separate pathways used by *N. crassa* to consume cellodextrins and xylodextrins released by its secreted enzymes (Galazka et al., 2010). A strain carrying a deletion of a previously-identified cellodextrin transporter (CDT-2, NCU08114) (Galazka et al., 2010) was unable to grow on xylan, and xylodextrins remained in the culture supernatant, suggesting that CDT-2 may be a xylodextrin transporter. As a direct test of transport function of CDT-2, *S. cerevisiae* strains expressing cdt-2 were able to import xylobiose, xylotriose and xylotetraose (FIG. 1). As with CDT-1, orthologues of CDT-2 are widely distributed in the fungal kingdom (Galazka et al., 2010), suggesting that many fungi consume xylodextrins derived from plant cell walls.

Following transport into a cell, the hydrolysis of xylodextrins would allow their further use as a carbon source. Notably, *N. crassa* expresses a putative intracellular β-xylosidase, GH43-2 (NCU01900), when grown on xylan (Sun et al., 2012). Applicants found that purified GH43-2 displayed robust hydrolase activity towards xylodextrins with a degree of polymerization (DP) spanning from 2 to 8, and with a pH optimum near 7. Furthermore, as with intracellular β-glucosidases (Galazka et al., 2010), intracellular β-xylosidases are also widespread in fungi (Sun et al., 2012).

Figure 3A:
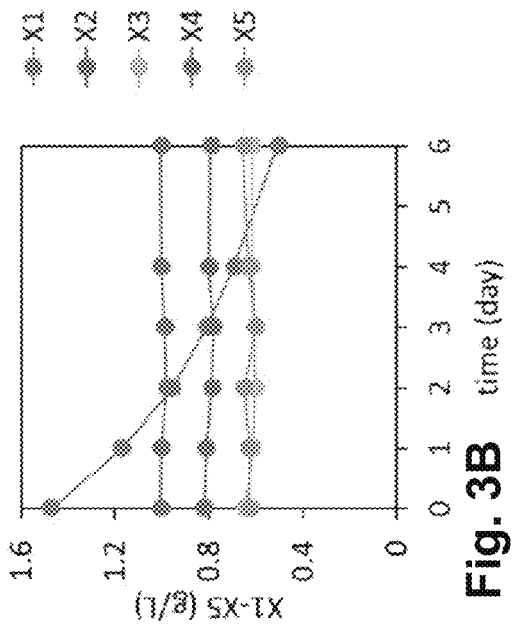
FIG. 3A-FIG. 3D illustrate components of a xylodextrin consumption pathway in S. cerevisiae. S. cerevisiae was grown with xylodextrins and xylose as the carbon source.
Figure 3B:
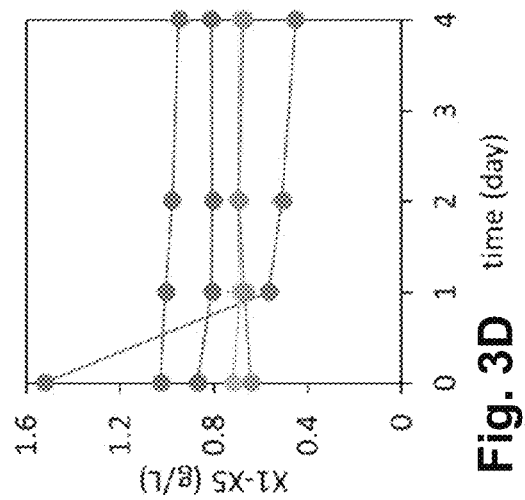
Figure 3C:
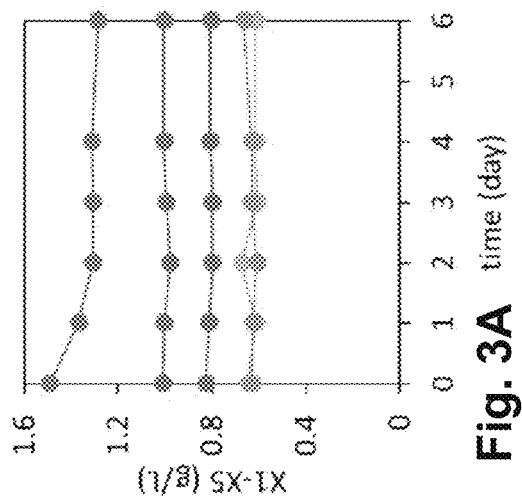
Figure 3D:
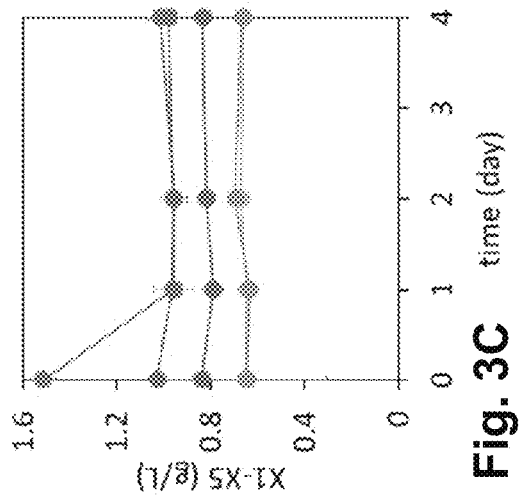

Applicants had thus identified a protein that could transport xylodextrins into cells (CDT-2) and a protein that could hydrolyze xylodextrins (GH43-2). To test whether *S. cerevisiae* could utilize xylodextrins, an *S. cerevisiae* strain was engineered with the XR/XDH pathway derived from *Scheffersomyces stipitis*, similar to the one utilized by *N. crassa* (Sun et al., 2012), as well as engineered with a xylodextrin transport and consumption pathway from *N. crassa*. The xylose-utilizing yeast expressing CDT-2 from *N. crassa*, the intracellular β-xylosidase GH43-2 from *N. crassa*, and the XR and XDH from *S. stipitis* was able to directly utilize xylodextrins with DPs (degrees of polymerization) of 2 or 3 (FIG. 2A). A control wild-type *S. cerevisiae* strain was not able to directly utilize xylodextrins (FIG. 3A and FIG. 3C). Similarly, an *S. cerevisiae* strain that was engineered with a xylose utilization pathway, but not a xylodextrin transport pathway, was not able to metabolize xylodextrins (FIG. 3B and FIG. 3D).

Engineered Strains Produce Xylosyl-Xylitol Oligomers

A similar experiment was performed as for FIG. 2A, except that a higher cell density culture ($OD_{600}$=20) was used (See FIG. 2B). Notably, high cell density cultures of the engineered yeast were capable of consuming xylodextrins with DPs up to 5, but xylose levels remained high (FIG. 2B), suggesting the existence of unknown bottlenecks in the engineered yeast. These results are similar to those of a previous attempt to engineer *S. cerevisiae* for xylodextrin consumption, in which xylose was reported to accumulate in the culture medium (Fujii et al., 2011). Applicants were intrigued as to why xylodextrin concentrations in this culture were decreasing, but xylose concentrations remained relatively stable over time (were not decreasing). Without wishing to be bound by theory, it was thought that the xylose reductase from *S. stipitis* would convert the xylose (generated by hydrolysis of xylodextrins by the β-xylosidase GH43-2 from *N. crassa*) into xylitol, which would then be further metabolized. In this regard, it was thought that xylose would be consumed, not accumulated in this culture as was observed. Applicants sought to explore this unknown bottleneck and analyzed the contents of the culture supernatants. Analysis of the supernatants from cultures with xylodextrins unexpectedly revealed that the xylodextrins were being converted into xylosyl-xylitol oligomers, a set of previously unknown metabolic intermediates, by the engineered yeast, rather than hydrolyzed to xylose and consumed (FIG. 4A and FIG. 4B). The resulting xylosyl-xylitol oligomers were effectively dead-end products that could not be metabolized further by this engineered yeast strain.

Applicants discovery that the XR/XDH/CDT-2/GH43-2 *S. cerevisiae* yeast strain was producing xylosyl-xylitol oligomers was surprising, as it was thought that this strain would effectively metabolize xylodextrins into xylose for consumption. Further, this surprising discovery may be quite beneficial. Without wishing to be bound by theory, it is thought that the xylosyl-xylitol oligomers may be useful for various purposes such as, for example, use as sweeteners, as prebiotics, or as anti-infection medications. Applicants were thus interested in better understanding the production of the xylosyl-xylitol oligomers in engineered yeast strains.

Investigating Mechanism of Xylosyl-Xylitol Oligomer Production

Figure 5:
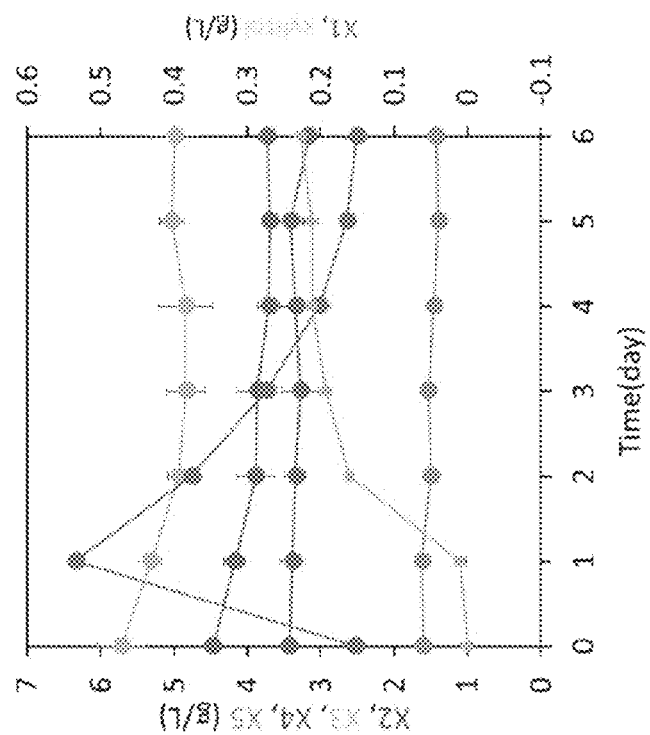
FIG. 5 illustrates xylodextrin metabolism by a co-culture of yeast strains to identify the enzymatic source of xylosyl-xylitol production. A mixture of a xylose utilization strain (SR8) with a cell density at $OD_{600}=1.0$ and a xylodextrin hydrolyzing strain (D452-2 with plasmid pXD8.4 that expresses CDT-2 and GH43-2) with a cell density at $OD_{600}=20$ were co-cultured in a medium containing 2% xylodextrin.

To test whether the xylosyl-xylitol oligomer production resulted from side reactions of xylodextrins with endogenous *S. cerevisiae* enzymes, two separate yeast strains were incubated in a combined culture: one strain containing the xylodextrin hydrolysis pathway composed of CDT-2 and GH43-2, and the second strain engineered with the XR/XDH xylose consumption pathway. The strain expressing CDT-2 and GH43-2 would be able to cleave xylodextrins to xylose, which could then be secreted and serve as a carbon source for the strain expressing the xylose consumption pathway (XR and XDH). By contrast, the engineered yeast expressing XR and XDH, but not the xylodextrin transport and hydrolysis pathway (CD-2 and GH43-2) would only be capable of consuming xylose. When these strains were co-cultured, it was found that xylodextrins were being consumed without producing the xylosyl-xylitol byproduct (FIG. 5). X2 and X3 decreased and the xylitol monomer was produced, but notably, xylosyl-xylitol oligomers were not detected. These results suggest that endogenous yeast enzymes and GH43-2 transglycolysis activity are not responsible for generating the xylosyl-xylitol byproducts, suggesting that they must be generated by the xylose reductase (XR), which in this case was from *S. stipitis*.

Figures 6A, 6B:
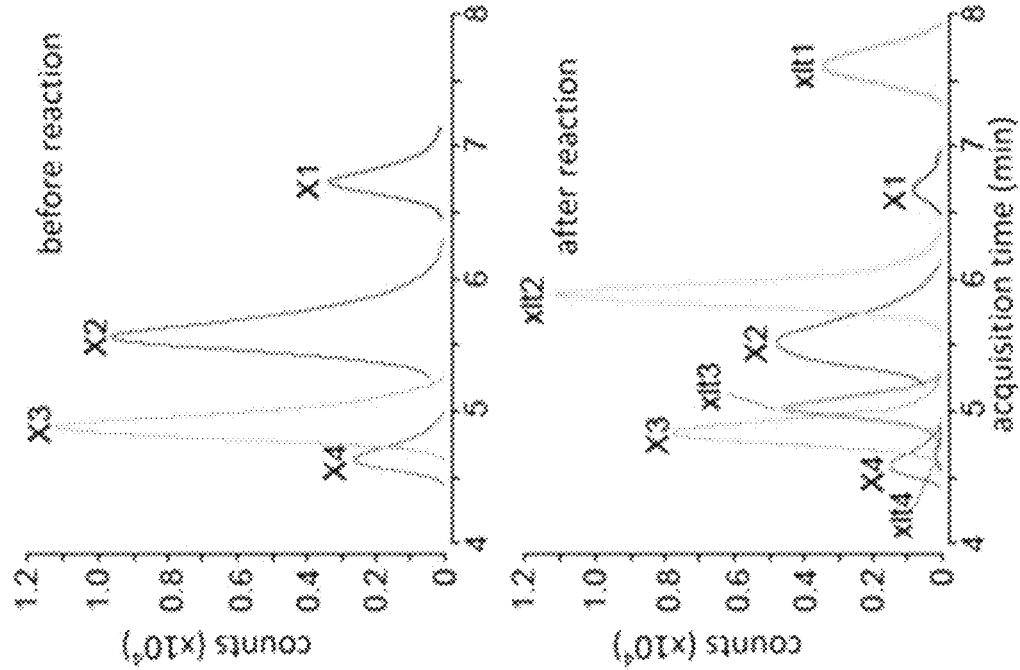
FIG. 6A-6B illustrate the in vitro production of xylosyl-xylitol oligomers by the xylose reductase (XR) enzyme from *N. crassa*, XYR-1.

Purified Xylose Reductase Catalyzes Production of Xylosyl-Xylitol Oligomers from Xylodextrin Substrates Without wishing to be bound by theory, it was thought that if the xylosyl-xylitol byproducts were generated by XR from *S. stipitis*, similar side products might be generated by the XR in *N. crassa*. To directly test the ability of a xylose reductase enzyme to generate a xylosyl-xylitol oligomer from a xylodextrin substrate, an in vitro assay was performed with the xylose reductase, XYR-1, from *Neurospora crassa*. As can be seen in FIG. 6A and FIG. 6B, when incubated with xylodextrin substrates having degrees of polymerization of from 2 to 4, XYR-1 was able to directly produce xylosyl-xylitol oligomers with a degree of polymerization of up to 3 (xlt3).

β-Xylosidase GH43-7 Hydrolyzes Xylosyl-Xylitol Oligomers

Figure 7:
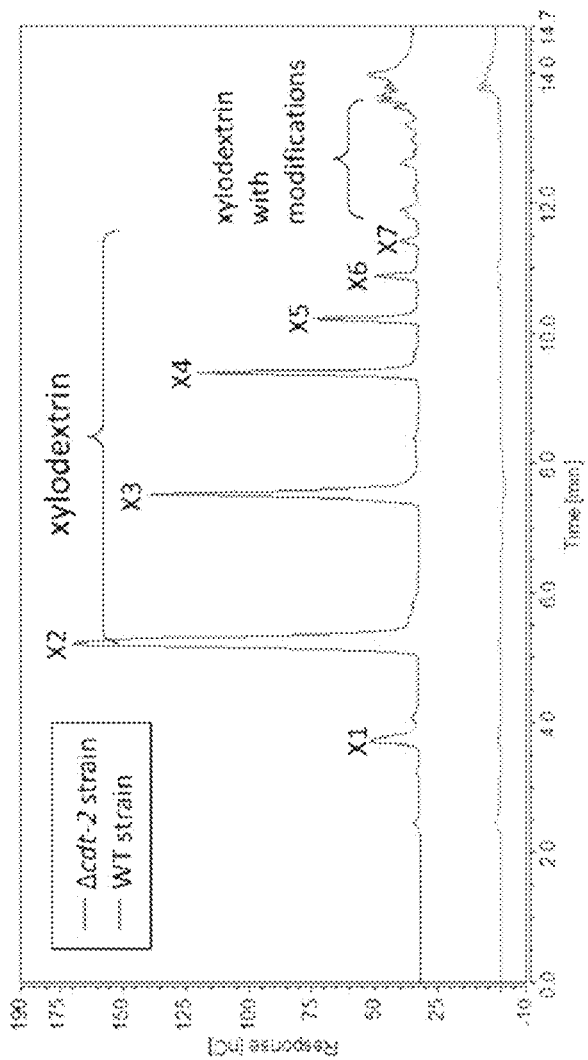
FIG. 7 illustrates xylodextrins in the xylan culture supernatant of the *N. crassa* Δcdt-2 strain. 25 µL of 1:200 diluted *N. crassa* xylan culture supernatant was analyzed by HPAEC on a CarboPac PA200 column. While no detectable soluble sugars were found in the culture supernatant of the wild-type strain (magenta line), the Δcdt-2 strain (blue line) left a high concentration of unmodified and modified xylodextrins in the culture supernatant. Little xylose was found, indicating xylose was transported by means of different transporters.
Figure 8A:
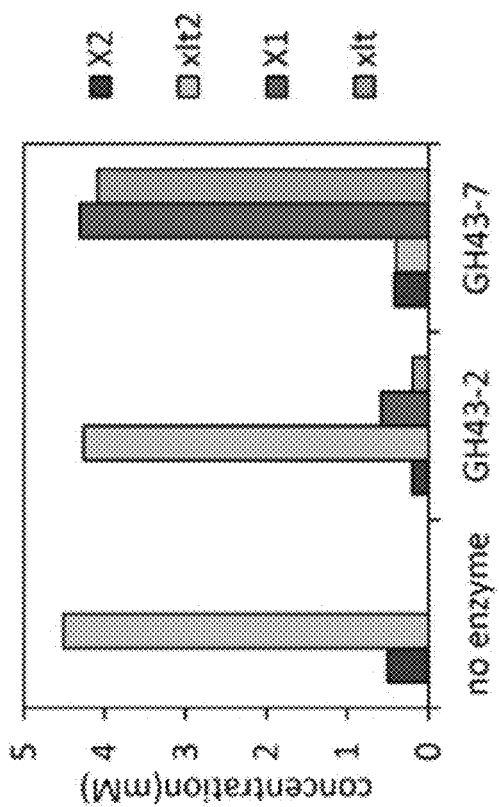
FIG. 8A-FIG. 8B illustrate activity of GH43-2 and GH43-7 β-xylosidases on various xylodextrin or xylosyl-xylitol oligomer substrates.
Figure 8B:
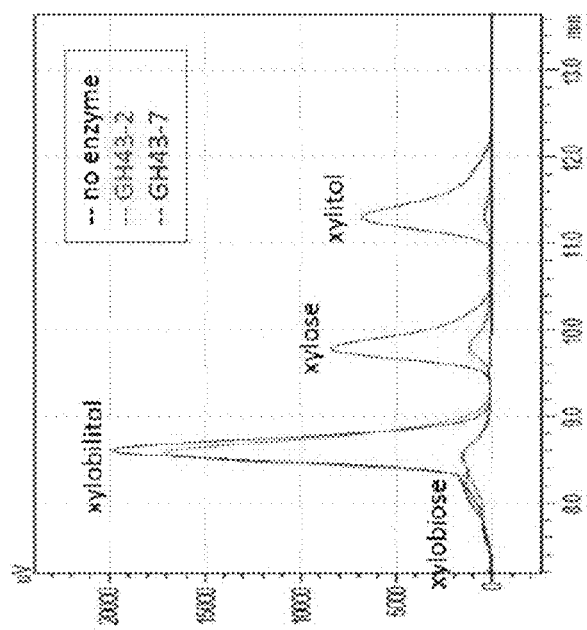

From the experiment described above in FIG. 6, it was found that the xylose reductase XYR-1 (NCU08384) from *N. crassa* could generate xylosyl-xylitol products from xylodextrins in vitro. However, when grown in culture, no xylosyl-xylitol byproducts accumulated in the *N. crassa* culture medium (FIG. 7), suggesting the existence of an endogenous pathway in *N. crassa* that is capable of metabolizing xylosyl-xylitol oligomers. It was found that a second putative intracellular β-xylosidase upregulated in *N. crassa* grown on xylan, GH43-7 (NCU09625) (Sun et al., 2012), had weak β-xylosidase activity, but also rapidly hydrolyzed the xylosyl-xylitol into xylose and xylitol (FIG. 8A and FIG. 8B). Although activity of this enzyme is beneficial from a xylose consumption point of view, the activity of this protein does not allow for the accumulation of xylosyl-xylitol oligomers. However, without wishing to be bound by theory, as this protein (GH43-7) has been shown to have direct xylosyl-xylitol hydrolase activity, Applicants believe that reduction of activity or deletion of this protein or other proteins with similar function would lead to the renewed accumulation of xylosyl-xylitol oligomers.

Further Experiments

Figure 9A:
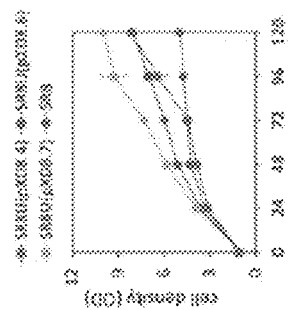
FIG. 9A-FIG. 9H illustrates growth and metabolic aspects of various engineered yeast strains.
Figure 9B:
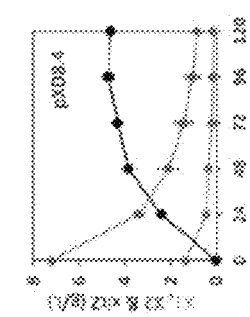
Figure 9C:
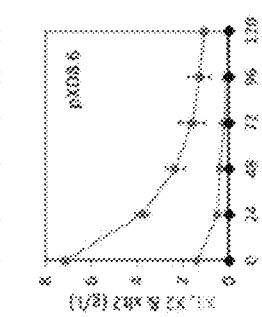
Figure 9D:
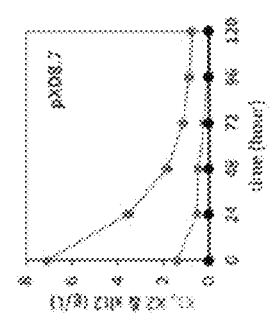
Figure 9E:
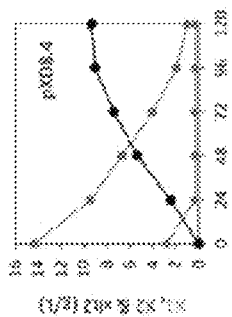
Figure 9F:
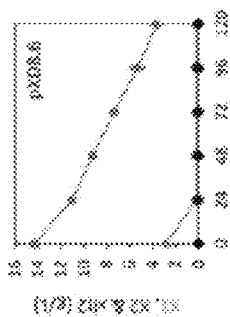
Figure 9G:
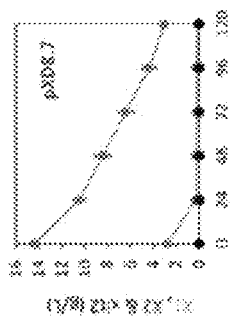
Figure 9H:
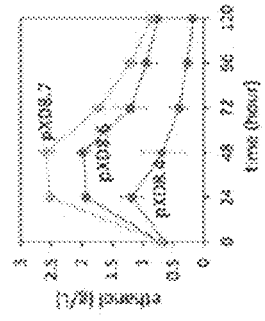
Figure 10:
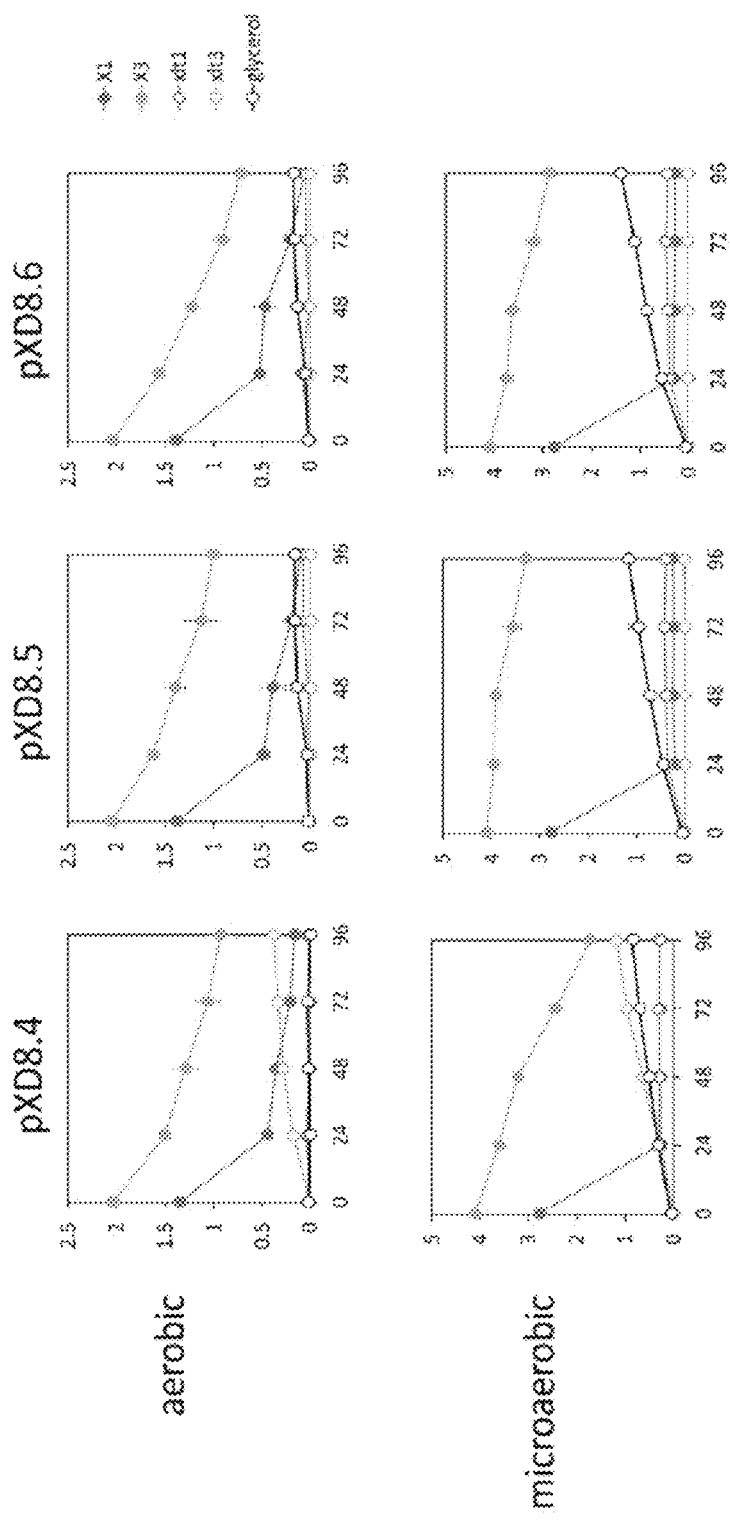
FIG. 10 illustrates carbohydrate and their derivatives profiling during yeast growth on xylodextrin. Yeast growth with xylodextrin as the sole carbon source under aerobic conditions with a cell density of $OD_{600}=20$ or under microaerobic conditions with a cell density of $OD_{600}=80$. Cultures with yeast strain SR8 transformed with plasmid expressing CDT-2 and GH43-2 (pXD8.4), CDT-2 and GH43-7 (pXD8.6), or CDT-2, GH43-2, and GH43-7 (pXD8.7) are shown. All growth experiments were performed in biological triplicate and error bars indicate the standard deviation between experiments.

To further explore the various products produced by various engineered yeast strains, a series of fermentation experiments were conducted. FIG. 9A shows growth rates of wild-type *S. cerevisiae* SR8 yeast as compared to SR8 yeast transformed with CDT-2 and GH43-2 (pXD8.4), transformed with CDT-2 and GH43-7 (pXD8.6), or transformed with CDT-2, GH43-2, and GH43-7 (pXD8.7) when grown on xylodextrins as the sole carbon source. It was found that the engineered yeast strains had some improved growth as compared to wild type. The strain with pXD8.4 was most similar to wild-type, presumably because this strain accumulates the xylosyl-xylitol oligomers instead of utilizing xylose from hydrolyzed xylodextrins. FIG. 9B, FIG. 9C, and FIG. 9D show xylodextrin and xylosyl-xylitol oligomer levels in a starting culture of $OD_{600}$=20 for the indicated yeast strain under microaerobic conditions when grown on xylodextrins. Xylosyl-xylitol accumulation was only observed in the SR8 strain bearing the plasmid pXD8.4. FIG. 9E, FIG. 9F, and FIG. 9G show xylodextrin and xylosyl-xylitol oligomer levels in a starting culture of $OD_{600}$=80 for the indicated yeast strain under microaerobic conditions when grown on xylodextrins. Again, only the strain with pXD8.4 could accumulate xylosyl-xylitol oligomers. Similar results are presented in FIG. 10, but with different xylodextrins and their derivatives being analyzed. As can be seen in FIG. 9H, while the strain with pXD8.7 was the most productive ethanol producer, this strain is incapable of accumulating xylosyl-xylitol oligomers. The results further corroborate that xylose reductase is capable of producing xylosyl-xylitol oligomers from a xylodextrin substrate, and that the *N. crassa* enzyme GH43-7 possesses xylosyl-xylitol hydrolase activity and is capable of metabolizing the xylosyl-xylitol oligomers.

Figure 13A:
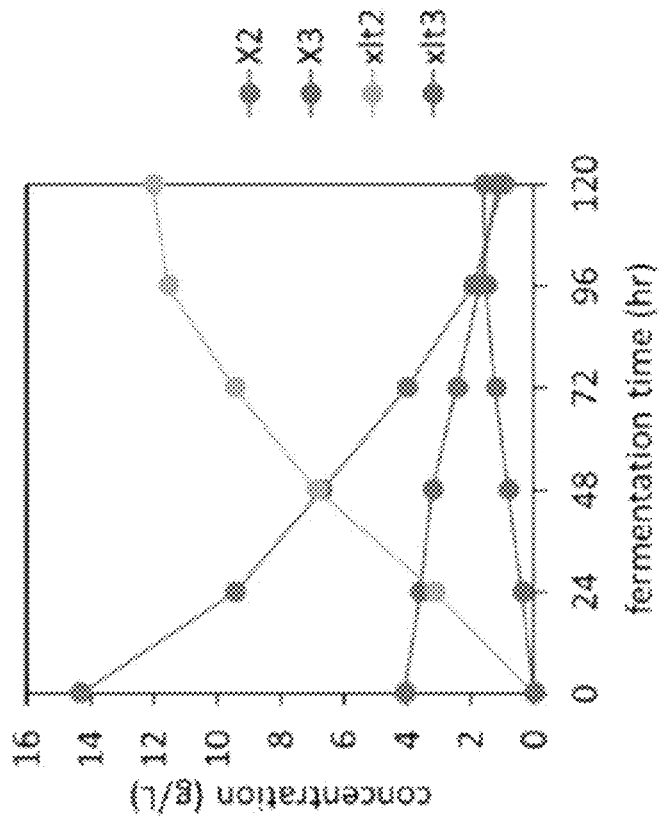

To further explore the capacity of engineered yeast to produce xylosyl-xylitol oligomers, additional experiments were performed. In one of these experiments, a starting culture having an $OD_{600}$ of 80 for the *S. cerevisiae* strain having XR/CDT-2/GH43-2 was used similar to the experiments in FIG. 9 and FIG. 10 with some differences, such as longer incubation times and analysis of different xylosyl-xylitol products. As can be seen in FIG. 13B, at the end of day 5, 93% of xylobiose and 71% of xylotriose were consumed. The yield of xylosyl-xylitol and xylosyl-xylosyl-xylitol were 90% and 54%, respectively. FIG. 13A illustrates the proposed mechanism of production of xylosyl-xylitol oligomers from xylodextrin substrates.

Figure 14:
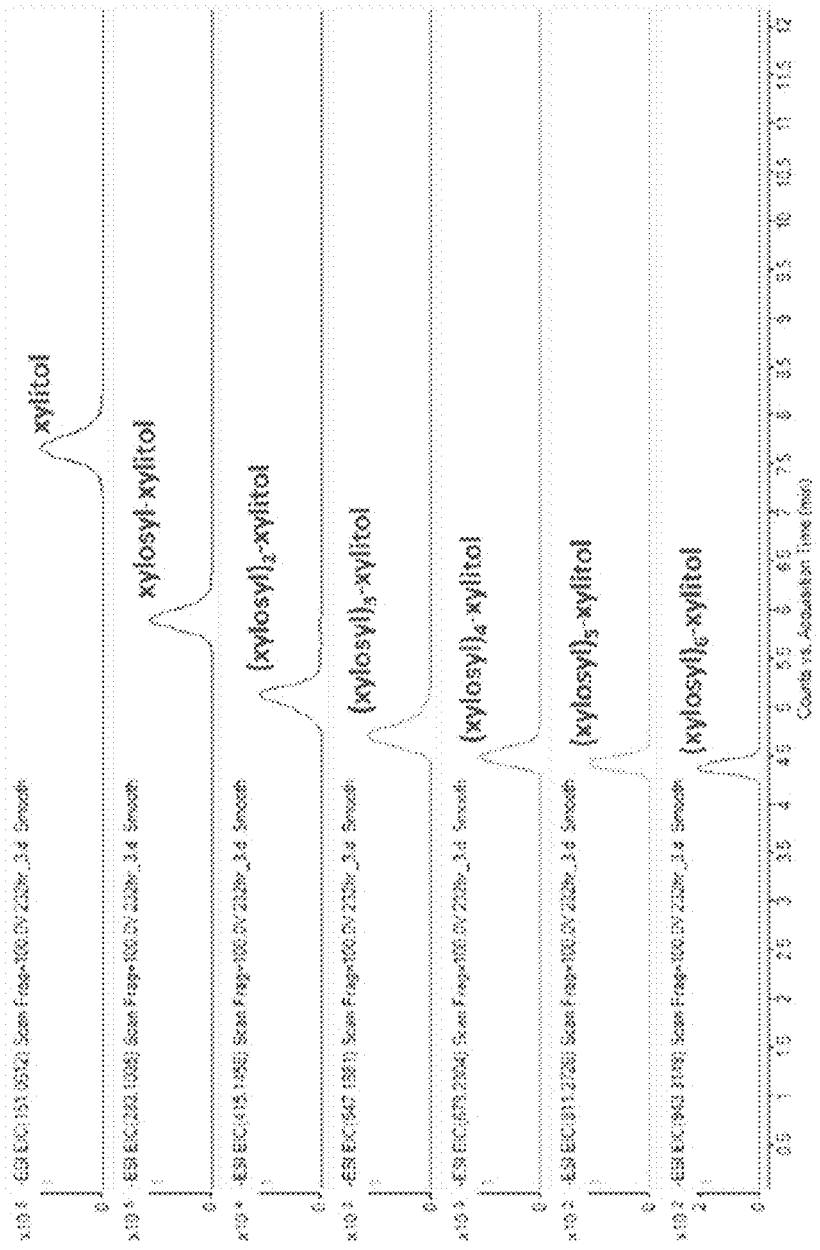
FIG. 14 illustrates the production of higher-order xylosyl-xylitol oligomers by engineered *S. cerevisiae* in fermentation cultures.

Experiments were also conducted in which the fermentations for the *S. cerevisiae* strain having XR/CDT-2/GH43-2 were allowed to continue until day 10. This is in contrast to the previous fermentations, which were terminated at day 6 or earlier. As can be seen in FIG. 14, after growth in culture for 10 days, the engineered yeast having a xylodextrin transporter and a xylose reductase were able to produce xylosyl-xylitol oligomers with a degree of polymerization of up to 6, albeit at a lower rate and ultimate lower yield than observed for shorter oligomers, such as xylosyl-xylitol.

Figure 15:
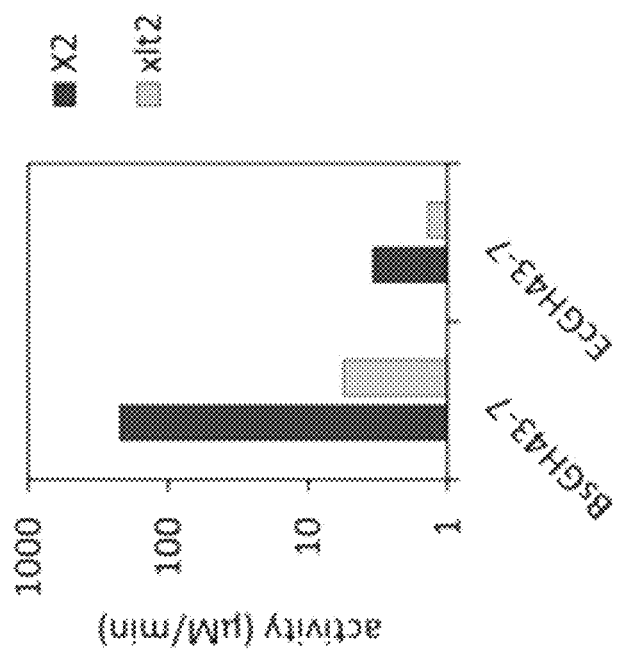
FIG. 15 illustrates the activity (µM/min) of two bacterial GH43-7 enzymes from *B. subtilis* (BsGH43-7) and *E. coli* (EcGH43-7) on a xylobiose substrate (X2) or on a xylosyl-xylitol substrate (xlt2).

Experiments were also conducted to further explore potential xylosyl-xylitol hydrolase activity of other β-xylosidases. From FIG. 11, it was found that both *B. subtilis* and *E. coli* have homologous proteins to GH43-7. To see if these proteins actually have xylosyl-xylitol hydrolase activity, purified *B. subtilis* GH43-7 and purified *E. coli* GH43-7 were incubated with xylobiose (X2) or xylosyl-xylitol (xlt2) and their activity on these substrates was analyzed. As can be seen in FIG. 15, both *B. subtilis* GH43-7 and *E. coli* GH43-7 exhibited xylosyl-xylitol hydrolase activity on xylosyl-xylitol substrates. These two proteins also exhibited β-xylosidase activity on xylobiose substrates. These proteins are thus examples of β-xylosidases that exhibit both β-xylosidase activity (on a xylodextrin substrate) and xylosyl-xylitol hydrolase activity (on a xylosyl-xylitol oligomer substrate). This is in contrast to the *N. crassa* GH43-7 β-xylosidase, which exhibited weak β-xylosidase activity (on xylodextrin substrate), but had strong xylosyl-xylitol activity (on xylosyl-xylitol oligomer substrate). In summary, two GH43 enzymes from bacteria *Bacillus subtilis* (AAB41091.1) and *Escherichia coli* (WP_000406872.1) were tested and confirmed to both cleave xylosyl-xylitol.

Discussion

Figure 16:
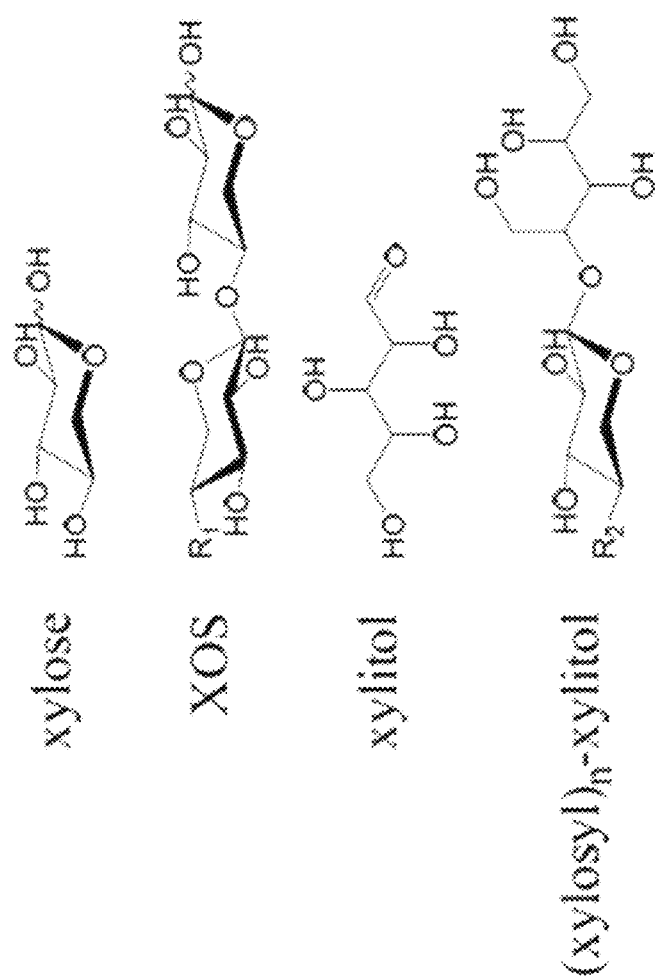
FIG. 16 illustrates the structures of xylose, XOS (xylooligosaccharides), xylitol, and (xylosyl)$_n$-xylitol. R1 and R2 represent a hydroxyl group or β-1,4-linked xylose monomers.

Applicants found that the fungal xylose reductases, widely used in industrial microbial xylitol production, also reduce xylooligosaccharides (XOS). The products are xylosyl-xylitol oligomers ((xylosyl)$_n$-xylitol), a set of compounds not previously known to be intermediates in the metabolism of xylodextrins. The structures of xylose, XOS, xylitol, and (xylosyl)$_n$-xylitol are depicted in FIG. 16. The results suggest that xylose reductases capable of acting on xylooligosaccharides (XOS) may be used for the production of xylosyl-xylitol oligomers.

Figure 11:
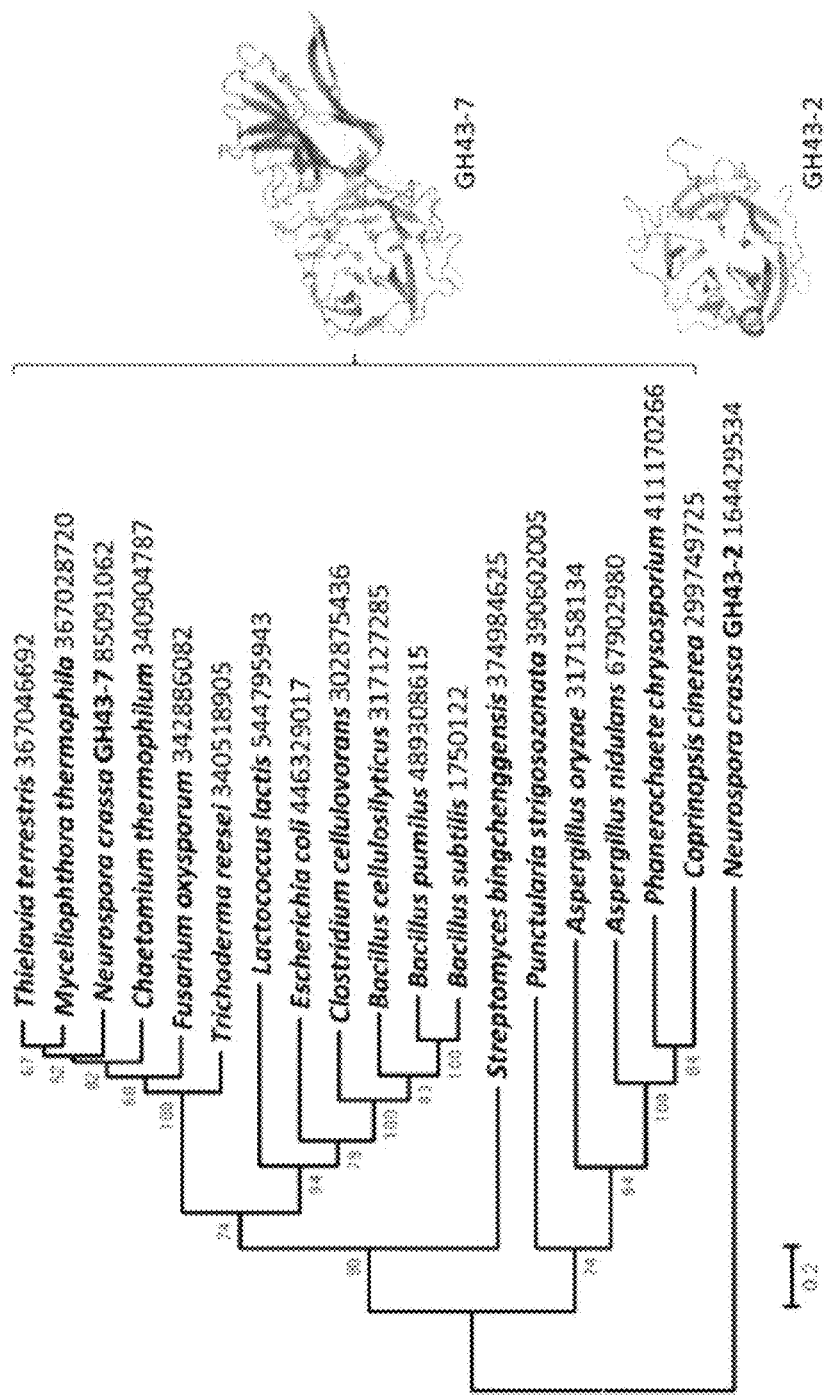
FIG. 11 illustrates a phylogenetic distribution of the β-xylosidases in the GH43-2 (NCU01900) and GH43-7 (NCU09652) families. The NCBI GI numbers of the sequences used to build the phylogenetic tree are indicated beside the species names. 1000 bootstrap replicates were performed to calculate the supporting values shown on the branches. The scale bar indicates 0.2 substitutions per amino acid residue. The homology models of GH43-2 and GH43-7, shown to the right, were built with the Phyre2 server. Despite possessing a very similar catalytic domain (green) with GH43-2, GH43-7 has an additional C-terminal accessory domain (magenta) which may lead to its substrate selectivity for xylosyl-xylitol oligomers.

Further, the newly-identified xylosyl-xylitol-specific β-xylosidase GH43-7 is widely distributed in fungi and bacteria (FIG. 11). These results reveal that the widely-used XR/XDH pathway naturally has broad substrate specificity for xylodextrins, and that fungi and bacteria may use parallel intracellular β-xylosidases to hydrolyze xylodextrins and xylosyl-xylitols to generate the monomers xylose and xylitol. A summary of the xylodextrin transport and metabolism pathways described in this Example is provided in FIG. 12. To improve xylosyl-xylitol oligomer production from a xylodextrin substrate in a cell having xylose reductase activity, proteins having xylosyl-xylitol hydrolase activity should have their activity reduced or removed entirely from a cell to allow for accumulation of the xylosyl-xylitol oligomers.

Example 2: Modeling of Xylose Reductases Having Xylodextrin Reductase Activity

This Example describes modeling experiments which model a xylose reductase enzyme acting on a xylodextrin substrate.

Results

From Example 1, Applicants discovered and provided examples of xylose reductase enzymes that exhibited xylodextrin reductase activity. Xylose reductases traditionally are known to catalyze the conversion of xylose to xylitol, but Applicants have shown that these enzymes may also have xylodextrin reductase activity, where they catalyze the conversion of a xylooligosaccharide (xylodextrin) to a xylosyl-xylitol oligomer.

To further explore the xylodextrin reductase catalytic activity of xylose reductases, Applicants performed modeling experiments. In this investigation, the structure of *Candida tenuis* xylose reductase (CtXR, AAC25601.1)(Kavanagh et al., 2002), a close homologue of *Scheffersomyces stipitis* protein XYL1 (SsXR), was analyzed. Recall from Example 1 that SsXR was a xylose reductase found to have xylodextrin reductase activity.

Figure 17:
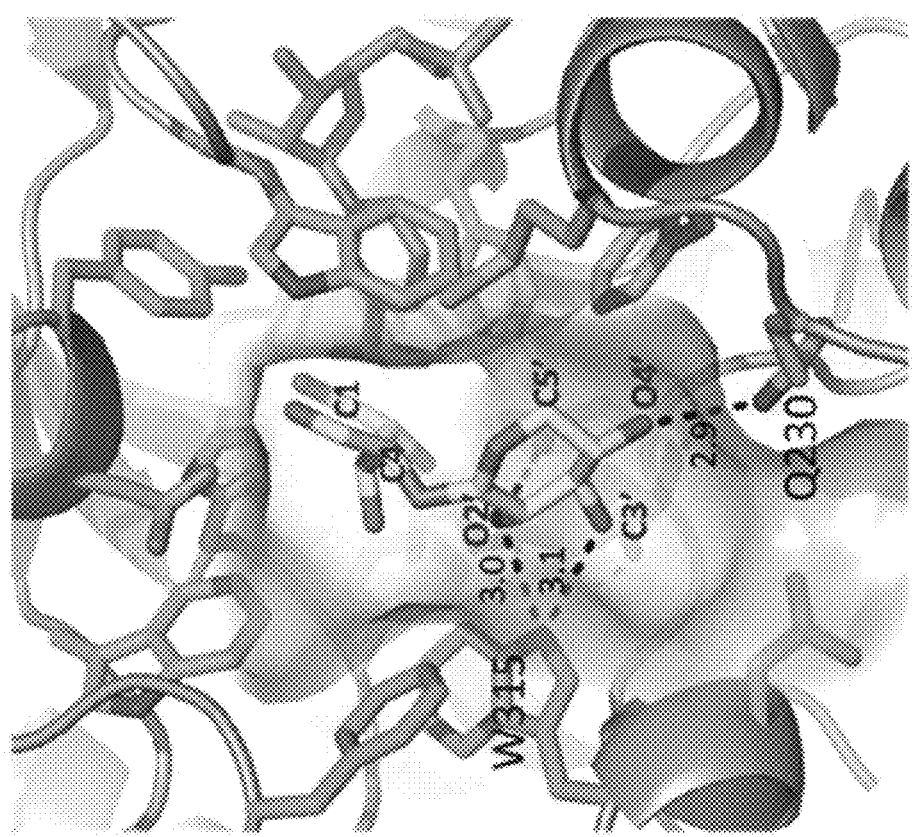
FIG. 17 illustrates a computational docking model of xylobiose to *Candida tenuis* xylose reductase (CtXR), with xylobiose in yellow, NADH cofactor in magenta, protein secondary structure in dark green, active site residues in bright green and showing side-chains. Part of the CtXR surface is shown to depict the shape of the active site pocket. Black dotted lines show predicted hydrogen bonds between CtXR and the non-reducing end residue of xylobiose.

CtXR contains an open active site cavity where xylose could bind, located near the binding site for the NADH co-factor (Kavanagh et al., 2002; Kratzer et al., 2006). Applicants found that, notably, the open shape of the active site can readily accommodate the binding of longer xylodextrin substrates (FIG. 17). Using computational docking algorithms (Trott et al., 2010), xylobiose was found to fit well in the pocket. Furthermore, there do not appear to be any obstructions in the protein that would prevent longer xylodextrin oligomers from binding.

In summary, Applicants have used computational docking analyses to show that xylose reductases (XR) generally have open active sites that can readily accommodate xylodextrins as substrates. Without wishing to be bound by theory, it is thought that xylose reductases having active sites that can accommodate xylodextrins as substrates will exhibit xylodextrin reductase activity. Further, and without wishing to be bound by theory, it is thought that this helps explain the surprising finding of the accumulation of xylosyl-xylitol oligomers in Example 1, as the xylose reductases analyzed were likely able to accommodate xylodextrins as substrates to produce xylosyl-xylitol oligomers via xylodextrin reductase activity.

Example 3: Expanding Xylose Metabolism in Yeast for Plant Cell Wall Conversion to Biofuels This Example elaborates on the experiments, data, and information provided in Examples 1 and 2. Sustainable biofuel production from renewable biomass will require the efficient and complete use of all abundant sugars in the plant cell wall. Using the cellulolytic fungus *Neurospora crassa* as a model, Applicants have identified a xylodextrin transport and consumption pathway required for its growth on hemicellulose. Reconstitution of this xylodextrin utilization pathway in *Saccharomyces cerevisiae* revealed that fungal xylose reductases act as xylodextrin reductases, producing xylosyl-xylitol oligomers as metabolic intermediates. Xylodextrins and xylosyl-xylitol oligomers are then hydrolyzed by two hydrolases to generate intracellular xylose and xylitol. Xylodextrin consumption using a xylodextrin transporter, xylodextrin reductases and tandem intracellular hydrolases in cofermentations with sucrose and glucose greatly expands the capacity of yeast to use plant cell wall-derived sugars and has the potential to increase the efficiency of both first-generation and next-generation biofuel production.

Materials and Methods

*Neurospora crassa* Strains

*N. crassa* strains obtained from the Fungal Genetics Stock Center (FGSC) (McCluskey, Wiest, and Plamann 2010) include the WT (FGSC 2489) and deletion strains for the two oligosaccharide transporters: NCU00801 (FGSC 16575) and NCU08114 (FGSC 17868) (Colot et al. 2006).

*Neurospora crassa* Growth Assay

Conidia were inoculated at a concentration equal to $10^6$ conidia per mL in 3 mL Vogel's media (Vogel 1956) with 2% wt/vol powdered *Miscanthus giganteus* (Energy Bioscience Institute, UC-Berkeley), Avicel PH 101 (Sigma), beechwood xylan (Sigma), or pectin (Sigma) in a 24-well deep-well plate. The plate was sealed with Corning™ breathable sealing tape and incubated at 25° C. in constant light and with shaking (200 rpm). Images were taken at 48 hours. Culture supernatants were diluted 200 times with 0.1 M NaOH before Dionex high-performance anion exchange chromatographic (HPAEC) analysis, as described below.

Plasmids and Yeast Strains

Template gDNA from the *N. crassa* WT strain (FGSC 2489) and from the *S. cerevisiae* S288C strain was extracted (the world wide web dot fgsc.net/fgn35/lee35.pdf) (McCluskey, Wiest, and Plamann 2010). Open reading frames (ORFs) of the β-xylosidase genes NCU01900 and NCU09652 (GH43-2 and GH43-7) were amplified from the *N. crassa* gDNA template. For biochemical assays, each ORF was fused with a C-terminal His$_6$-tag and flanked with the *S. cerevisiae* P$_{TEF1}$ promoter and CYC1 transcriptional terminator in the 2μ yeast plasmid pRS423 backbone. Plasmid pRS426_NCU08114 was described previously (Galazka et al. 2010). Plasmid pLNL78 containing the xylose utilization pathway (xylose reductase, xylitol dehydrogenase, and xylulose kinase) from *Scheffersomyces stipitis* was obtained from the lab of John Dueber (Latimer et al. 2014). Plasmid pXD2, a single-plasmid form of the xylodextrin pathway, was constructed by integrating NCU08114 (CDT-2) and NCU01900 (GH43-2) expression cassettes into pLNL78, using the In-Fusion cloning kit (Clontech). Plasmid pXD8.4 derived from plasmid pRS316 (SIKORSKI and HIETER 1989) was used to express CDT-2 and GH43-2, each from the P$_{CCW12}$ promoter. Plasmid pXD8.6 was derived from pXD8.4 by replacing the GH43-2 ORF with the ORF for GH43-7. Plasmid pXD8.7 contained all three expression cassettes (CDT-2, GH43-2 and GH43-7) using the P$_{CCW12}$ promoter for each. *S. cerevisiae* strain D452-2 (MATa leu2 his3 ura3 can1) (Kurtzman 1994) and SR8U (the uracil autotrophic version of the evolved xylose fast utilization strain SR8) (Kim et al. 2013) were used as recipient strains for the yeast experiments. The ORF for *N. crassa* xylose reductase (xyr-1, NcXR) was amplified from *N. crassa* gDNA and the introns were removed by overlapping PCR. XR ORF was fused to a C-terminal His$_6$-tag and flanked with the *S. cerevisiae* P$_{CCW12}$ promoter and CYC1 transcriptional terminator, and inserted into plasmid pRS313. A list of the plasmids used in this study can be found in Table 1.

TABLE 1

List of Plasmids

| Plasmid | Genotype and Use | Use | Reference |
|---|---|---|---|
| pRS426_NCU08114 | $P_{PGK1}$-CDT-2 | transport assay | (Galazka et al. 2010) |
| pRS423_GH43-2 | $P_{TEF1}$-GH43-2 | enzyme purification | this study |
| pRS423_GH43-7 | $P_{TEF1}$-GH43-7 | enzyme purification | this study |
| pRS313_NcXR | $P_{CCW12}$-NcXR | enzyme purification | this study |
| pET302_EcGH43-7 | EcGH43-7 | enzyme purification | this study |
| pET302_BsGH43-7 | BsGH43-7 | enzyme purification | this study |
| pLNL78 | $P_{RNR2}$-SsXK::$P_{TEF1}$-SsXR:: $P_{TEF1}$-SsXDH | fermentation | (Galazka et al. 2010) |
| pXD2 | $P_{RNR2}$-SsXK::$P_{TEF1}$-SsXR:: $P_{TEF1}$-SsXDH:: $P_{PGK1}$-CDT-2:: $P_{TEF1}$-GH43-2 | fermentation | this study |
| pXD8.4 | $P_{CCW12}$-CDT-2:: $P_{CCW12}$-GH43-2 | fermentation | this study |
| pXD8.6 | $P_{CCW12}$-CDT-2:: $P_{CCW12}$-GH43-7 | fermentation | this study |
| pXD8.7 | $P_{CCW12}$-CDT-2:: $P_{CCW12}$-GH43-7:: $P_{CCW12}$-GH43-7 | fermentation | this study |

Yeast Cell-Based Xylodextrin Uptake Assay

*S. cerevisiae* was grown in an optimized minimum medium (oMM) lacking uracil into late log phase. The oMM contained 1.7 g/L YNB (Sigma, Y1251), 2-fold appropriate CSM dropout mixture, 10 g/L $(NH_4)_2SO_4$, 1 g/L $MgSO_4 \cdot 7H_2O$, 6 g/L $KH_2PO_4$, 100 mg/L adenine hemisulfate, 10 mg/L inositol, 100 mg/L glutamic acid, 20 mg/L lysine, 375 mg/L serine and 100 mM 4-morpholineethanesulfonic acid (MES), pH 6.0 (Lin et al. 2014). Cells were then harvested and washed three times with assay buffer (5 mM MES, 100 mM NaCl, pH 6.0) and resuspended to a final OD600 of 40. Substrate stocks were prepared in the same assay buffer at a concentration of 200 µM. Transport assays were initiated by mixing equal volumes of the cell suspension and the substrate stock. Reactions were incubated at 30° C. with continuous shaking for 30 minutes. Samples were centrifuged at 14,000 rpm at 4° C. for 5 minutes to remove yeast cells. 400 µL of each sample supernatant was transferred to an HPLC vial containing 100 µL 0.5 M NaOH, and the concentration of the remaining substrate was measured by HPAEC as described below.

Enzyme Purification

*S. cerevisiae* strains transformed with pRS423_GH43-2, pRS423_GH43-7, or pRS313_NcXR were grown in oMM lacking histidine with 2% glucose until late log phase before harvesting by centrifugation. *E. coli* strains BL21DE3 transformed with pET302_BsGH43-7 or pET302_EcGH43-7 were grown in TB medium, induced with 0.2 mM IPTG at OD600 of 0.8, and harvested by centrifugation 12 hours after induction. Yeast or *E. coli* cell pellets were resuspended in a buffer containing 50 mM Tris-HCl, 100 mM NaCl, 0.5 mM DTT, pH 7.4 and protease inhibitor cocktail (Pierce). Cells were lysed with an Avestin homogenizer, and the clarified supernatant was loaded onto a HisTrap column (GE Healthcare). His-tagged enzymes were purified with an imidazole gradient, buffer-exchanged into 20 mM Tris-HCl, 100 mM NaCl, pH 7.4, and concentrated to 5 mg/mL.

Enzyme Assays

For the β-xylosidase assay of GH43-2 with xylodextrins, 0.5 µM of purified enzyme was incubated with 0.1% in-house prepared xylodextrin or 1 mM xylobiose (Megazyme) in 1×PBS at 30° C. Reactions were sampled at 30 min and quenched by adding 5 volumes of 0.1 M NaOH. The products were analyzed by HPAEC as described below. For pH profiling, acetate buffer at pH 4.0, 4.5, 5.0, 5.5, 6.0, and phosphate buffer at 6.5, 7.0, 7.5, 8 were added at a concentration of 0.1 M. For the β-xylosidase assay of GH43-2 and GH43-7 with xylosyl-xylitol, 10 µM of purified enzyme was incubated with 4.5 mM xylosyl-xylitol and 0.5 mM xylobiose in 20 mM MES buffer, pH=7.0, and 1 mM $CaCl_2$ at 30° C. Reactions were sampled at 3 hours and quenched by heating at 99° C. for 10 min. The products were analyzed by ion-exclusion HPLC as described below.

For the xylose reductase assays of NcXR, 1 µM of purified enzyme was incubated with 0.06% xylodextrin and 2 mM NADPH in 1×PBS at 30° C. Reactions were sampled at 30 min and quenched by heating at 99° C. for 10 min. The products were analyzed by LC-QToF as described below.

Oligosaccharide Preparation

Xylodextrin was purchased from Cascade Analytical Reagents and Biochemicals, or prepared according to published procedures (Akpinar, Erdogan, and Bostanci 2009) with slight modifications. In brief, 20 g beechwood xylan (Sigma-Aldrich) was fully suspended in 1000 mL water, to which 13.6 mL 18.4 M $H_2SO_4$ was added. The mixture was incubated in a 150° C. oil bath with continuous stirring. After 30 min, the reaction was poured into a 2 L plastic container on ice, with stirring to allow it to cool. Then 0.25 mol $CaCO_3$ was slowly added to neutralize the pH and precipitate sulfate. The supernatant was filtered and concentrated on a rotary evaporator at 50° C. to dryness. The in-house prepared xylodextrin contained about 30% xylose monomers and 70% oligomers. To obtain a larger fraction of short chain xylodextrin, the commercial xylodextrin was dissolved to 20% w/v and incubated with 2 mg/mL xylanase at 37° C. for 48 hours. Heat deactivation and filtration were performed before use.

Xylosyl-xylitol was purified from the culture broth of strain SR8 containing plasmids pXD8.4 in xylodextrin medium. 50 mL of culture supernatant was concentrated on a rotary evaporator at 50° C. to about 5 mL. The filtered sample was loaded on an XK 16/70 column (GE Healthcare) packed with Supelclean™ ENVI-Carb™ (Sigma-Aldrich), a solid phase extraction cartridge, mounted on an AKTA Purifier (GE Healthcare). The column was eluted with a gradient of acetonitrile at a flow rate of 3.0 mL/min at room temperature. Purified fractions, verified by LC-MS, were pooled and concentrated. The final product, containing 90% of xylosyl-xylitol and 10% xylobiose, was used as the substrate for enzyme assays and as an HPLC calibration standard.

Measurement of Xylosyl-Xylitol Production by Fungi and *B. subtilis*

*N. crassa* strain (FGSC 2489) and *A. nidulans* were stored and conidiated on agar slants of Volgel's medium (Vogel 1956) with 2% glucose. *T. reesei* (strain QM6a) was conidiated on potato dextrose agar (PDA) plates. Conidia from each fungi were collected by resuspending in water and used for inoculation at a concentration of $10^6$ cells per mL. *N. crassa* and *A. nidulans* were inoculated into Volgel's medium with 2% xylodextrin. *T. reesei* was inoculated into Trichoderma minimal medium (Penttila et al. 1987) with 2% xylodextrin. *N. crassa*, *A. nidulans*, and *T. reesei* were grown in shaking flasks at 25° C., 37° C., and 30° C., respectively. After 40 hours, mycelia from 2 mL of culture were harvested and washed with water on a glass fiber filter and transferred to a pre-chilled screw-capped 2 mL tube containing 0.5 mL Zirconia beads (0.5 mm) and 1.2 mL acidic acetonitrile extraction solution (80% Acetonitrile, 20% $H_2O$, and 0.1 M formic acid, (Rabinowitz and Kimball 2007). The tubes were then plunged into liquid nitrogen. The harvest process was controlled within 30 seconds. Samples were kept at −80° C. until extraction, as described below.

*B. subtilis* was stored on 0.5×LB (1% tryptone, 0.5% yeast extract, and 0.5% NaCl) agar plates. A single colony was inoculated into 0.5×LB liquid medium with 1% glucose and allowed to grow in a 37° C. shaker overnight. An inoculum from the overnight culture was transferred to fresh 0.5×LB liquid medium with 1% xylodextrin at an initial $OD_{600}$ of 0.2. After 40 hours, 2 mL of the culture was spun down and washed with cold PBS solution. Zirconia beads and acidic acetonitrile extraction solution were added to the cell pellet. The tubes were then flash frozen immediately and kept at −80° C. until extraction.

For extraction, all samples were allowed to thaw at 4° C. for 10 minutes, bead beat for two minutes, and vortexed at 4° C. for 20 minutes. 50 μL of the supernatant from each sample was analyzed by LC-MS/MS (See Mass spectrometric analyses section).

Aerobic Yeast Cultures with Xylodextrins

Yeast strains were pre-grown aerobically overnight in oMM medium containing 2% glucose, washed 3 times with water, and resuspended in oMM medium. For aerobic growth, strains were inoculated at a starting OD600 of 1.0 or 20 in 50 mL oMM medium with 3% w/v xylodextrins and cultivated in 250 mL Erlenmeyer flasks covered with 4 layers of miracle cloth, shaking at 220 rpm. At the indicated time points, 0.8 mL samples were removed and pelleted. 20 μL supernatants were analyzed by ion-exclusion HPLC to determine xylose, xylitol, glycerol, and ethanol concentrations. 25 μL of 1:200 diluted or 2 μL of 1:100 diluted supernatant was analyzed by HPAEC or LC-QToF, respectively, to determine xylodextrin concentrations.

Fed-Batch Anaerobic Fermentations

Anaerobic fermentation experiments were performed in a 1 L stirred tank bioreactor (DASGIP Bioreactor system, Type DGCS4, Eppendorf AG), containing oMM medium with 3% w/v xylodextrins inoculated with an initial cell concentration of OD600=20. The runs were performed at 30° C. for 107 h. The culture was agitated at 200 rpm and purged constantly with 6 L/h of nitrogen. For xylose plus xylodextrin co-fermentations, xylose was fed continuously at 0.8 mL/h from a 25% stock. During the fermentation, 3 mL cell-free samples were taken each 4 h with an autosampler through a ceramic sampling probe (Seg-Flow Sampling System, Flownamics). 20 μL of the supernatant fraction were analyzed by ion-exclusion HPLC to determine xylose, xylitol, glycerol, acetate and ethanol concentrations. 2 μL of 1:100 diluted supernatant was analyzed by LC-QToF to determine xylodextrin concentrations. For glucose plus xylodextrin co-fermentations, glucose was fed continuously at 2 mL/h from a 10% stock. Analytes were detected as described for xylose plus xylodextrin co-fermentations, with the addition of the measurement of glucose concentrations in the culture broth.

Xylose Fermentation Comparisons

For xylose fermentation comparisons between strain SR8 (XR/XDH) and SXA-R2P-E (XI), the grams of dry cell weight per OD600 were established for each strain grown on YPD and were found to be equivalent, 0.433+/−0.01 g per OD for strain SR8 and 0.423+/−0.01 g per OD for strain SXA-R2P-E. Yeast strains SR8 or SXA-R2P-E were pre-grown aerobically to mid-log or late-log phase in oMM or YSC medium containing 2% glucose, washed 3 times with water, and resuspended in either oMM or YSC medium, depending on the batch fermentation. Media containing 4% w/v xylose was inoculated with a range of starting OD values, as indicated in the figure panels, and then purged with $N_2$. Fermentations were carried out in 50 mL of oMM or YSC medium in 125 mL serum bottles shaking at 220 rpm in a 30° C. shaker. At the indicated time points, 1 mL samples were removed with a syringe and pelleted. 5 μL supernatants were analyzed by ion-exclusion HPLC to determine xylose, xylitol, glycerol, and ethanol concentrations.

Co-Fermentation of Sucrose Plus Xylodextrins

Yeast strain SR8U with plasmid pXD8.7 was pre-grown aerobically to late-log phase in oMM medium lacking uracil and containing 2% glucose, washed with water, and resuspended in oMM medium. Media containing 75 g/L sucrose plus or minus 15 g/L xylodextrins was inoculated with 20 OD of the washed yeast seed culture and purged with $N_2$. Fermentations were carried out in 50 mL of oMM medium in 125 mL serum bottles shaking at 220 rpm in a 30° C. shaker. At the indicated time points, 1 mL samples were removed and pelleted. 5 μL supernatants were analyzed by ion-exclusion HPLC to determine sucrose, glucose, fructose, xylose, xylitol, glycerol, and ethanol concentrations. 2 μL of 1:100 diluted supernatant was analyzed by LC-QToF, as described below, to determine xylodextrin concentrations.

Ion-Exclusion HPLC Analysis

Ion-exclusion HPLC was performed on a Shimadzu Prominence HPLC equipped with a refractive index detector. Xylose fermentation samples were resolved on a Rezex RFQ-Fast Fruit H+8% column (100×7.8 mm, Phenomenex) using a flow rate of 1 mL/min at 50° C. Xylodextrin fermentation samples were resolved on Aminex HPX-87H Column (300×7.8 mm, Bio-Rad) at a flow rate of 0.6 mL/min at 40° C. Both columns used a mobile phase of 0.01 N $H_2SO_4$.

HPAEC Analysis

HPAEC analysis was performed on a ICS-3000 HPLC (Thermo Fisher) using a CarboPac PA200 analytical column (150×3 mm) and a CarboPac PA200 guard column (3×30 mm) at 30° C. Following injection of 25 μL of diluted samples, elution was performed at 0.4 mL/min using 0.1 M NaOH in the mobile phase with sodium acetate gradients. For xylodextrin and xylosyl-xylitol separation, the acetate gradients were 0 mM for 1 min, increasing to 80 mM in 8 min, increasing to 300 mM in 1 min, keeping at 30 mM for 2 min, followed by re-equilibration at 0 mM for 3 min. Carbohydrates were detected using pulsed amperometric detection (PAD) and peaks were analyzed and quantified using the Chromeleon software package.

Mass Spectrometric Analyses

All mass spectrometric analyses were performed on an Agilent 6520 Accurate-Mass Q-TOF coupled with an Agilent 1200 LC. Samples were resolved on a 100×7.8 mm Rezex RFQ-Fast Fruit H+8% column (Phenomenex) using a mobile phase of 0.5% formic acid at a flow rate of 0.3 mL/min at 55° C.

To determine the accurate masses of the unknown metabolites, 2 μL of 1:100 diluted yeast culture supernatant was analyzed by LC-QToF. Nitrogen was used as the instrument gas. The source voltage (Vcap) was 3,000 V in negative ion mode, and the fragmentor was set to 100 V. The drying gas temperature was 300° C.; drying gas flow was 7 L/min; and nebulizer pressure was 45 psi. The ESI source used a separate nebulizer for the continuous, low-level introduction of reference mass compounds (112.985587, 1033.988109) to maintain mass axis calibration. Data was collected at an acquisition rate of 1 Hz from m/z 50 to 1100, and stored in centroid mode.

LC-MS/MS was performed to confirm the identity of xylosyl-xylitol and xylosyl-xylosyl-xylitol. The compound with a retention time (RT) of 5.8 min and m/z ratio of 283.103 and the compound with an RT of 4.7 min and m/z ratio of 415.15 were fragmented with collision energies of 10, 20 and 40 eV. MS/MS spectra were acquired, and the product ions were compared and matched to the calculated fragment ions generated by the Fragmentation Tools in ChemBioDraw Ultra v13.

To quantify the carbohydrates and carbohydrate derivatives in the culture, culture supernatants were diluted 100-fold in water and 2 μL was analyzed by LC-QToF. Spectra were imported to Qualitative Analysis module of Agilent MassHunter Workstation software using m/z and retention time values obtained from the calibration samples to search for the targeted ions in the data. These searches generated extracted ion chromatograms (EICs) based on the list of target compounds. Peaks were integrated and compared to the calibration curves to calculate the concentration. Calibration curves were calculated from the calibration samples, prepared in the same oMM medium as all the samples, and curve fitting for each compound resulted in fits with $R^2$ values of 0.999. 4-morpholineethanesulfonic acid (MES), the buffer compound in the oMM medium with constant concentration and not utilized by yeast, was used as an internal standard (IS) for concentration normalization.

Results

The biological production of biofuels and renewable chemicals from plant biomass requires an economic way to convert complex carbohydrate polymers from the plant cell wall into simple sugars that can be fermented by microbes (Carroll and Somerville 2009; Chundawat et al. 2011). In current industrial methods, cellulose and hemicellulose, the two major polysaccharides found in the plant cell wall (Somerville et al. 2004), are generally processed into monomers of glucose and xylose, respectively (Chundawat et al. 2011). In addition to harsh pretreatment of biomass, large quantities of cellulase and hemicellulase enzyme cocktails are required to release monosaccharides from plant cell wall polymers, posing unsolved economic and logistical challenges (Lynd et al. 2002; Himmel et al. 2007; Jarboe et al. 2010; Chundawat et al. 2011). The bioethanol industry currently uses the yeast *Saccharomyces cerevisiae* to ferment sugars derived from cornstarch or sugarcane into ethanol (Hong and Nielsen 2012), but *S. cerevisiae* requires substantial engineering to ferment sugars derived from plant cell walls such as cellobiose and xylose (Kuyper et al. 2005; Jeffries 2006; van Maris et al. 2007; Ha et al. 2011; Hong and Nielsen 2012; Young et al. 2014).

Figures 18A, 18B:
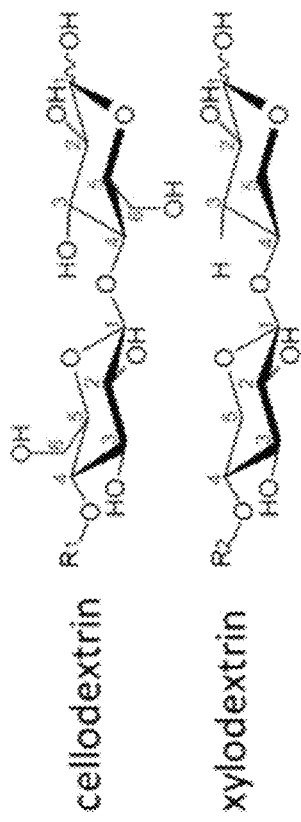
FIG. 18A illustrates two oligosaccharide components derived from the plant cell wall. Cellodextrins, derived from cellulose, are a major source of glucose. Xylodextrins, derived from hemicellulose, are a major source of xylose. The 6-methoxy group (blue) distinguishes glucose derivatives from xylose. $R_1$, $R_2$=H, cellobiose or xylobiose; $R_1$=β-1,4-linked glucose monomers in cellodextrins of larger degrees of polymerization; $R_2$=β-1,4-linked xylose monomers in xylodextrins of larger degrees of polymerization.
FIG. 18B illustrates transcriptional levels of transporters expressed in N. crassa grown on different carbon sources. Transcript levels reported in fragments per kilobase per million reads (FPKM) are derived from experiments published in (Coradetti et al. 2012; Sun et al. 2012). *CBT-1 transports cellobionic acid, the product of lytic polysaccharide monooxygenases (LPMOs, or CaZy family AA9 and AA10) (Xiong et al. 2014).
Figure 19:
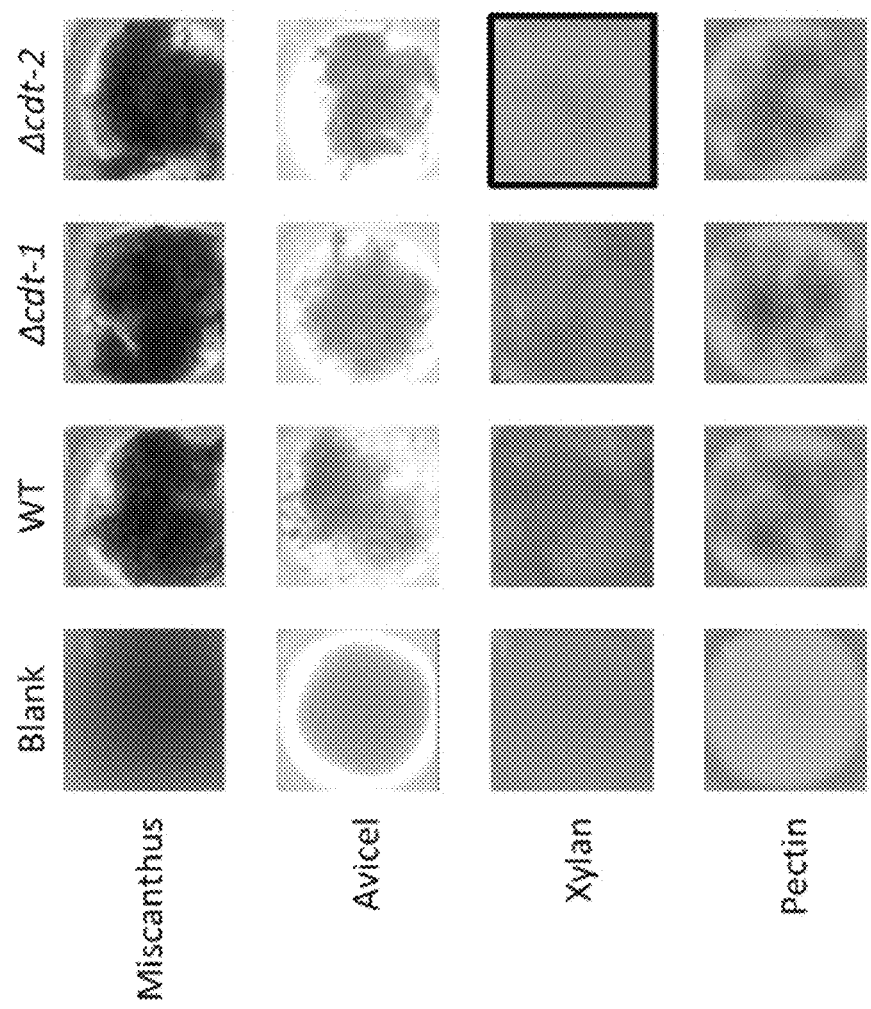
FIG. 19 illustrates growth of N. crassa strains on different carbon sources. Wild type (WT) N. crassa, or N. crassa with deletions of transporters cdt-1 (Δcdt-1) or cdt-2 (Δcdt-2), were grown on Miscanthus giganteus plant cell walls, or purified plant cell wall components. Avicel is a form of cellulose derived from plant cell walls. The black box shows the severe growth phenotype of the Δcdt-2 strain grown on xylan medium.
Figure 21:
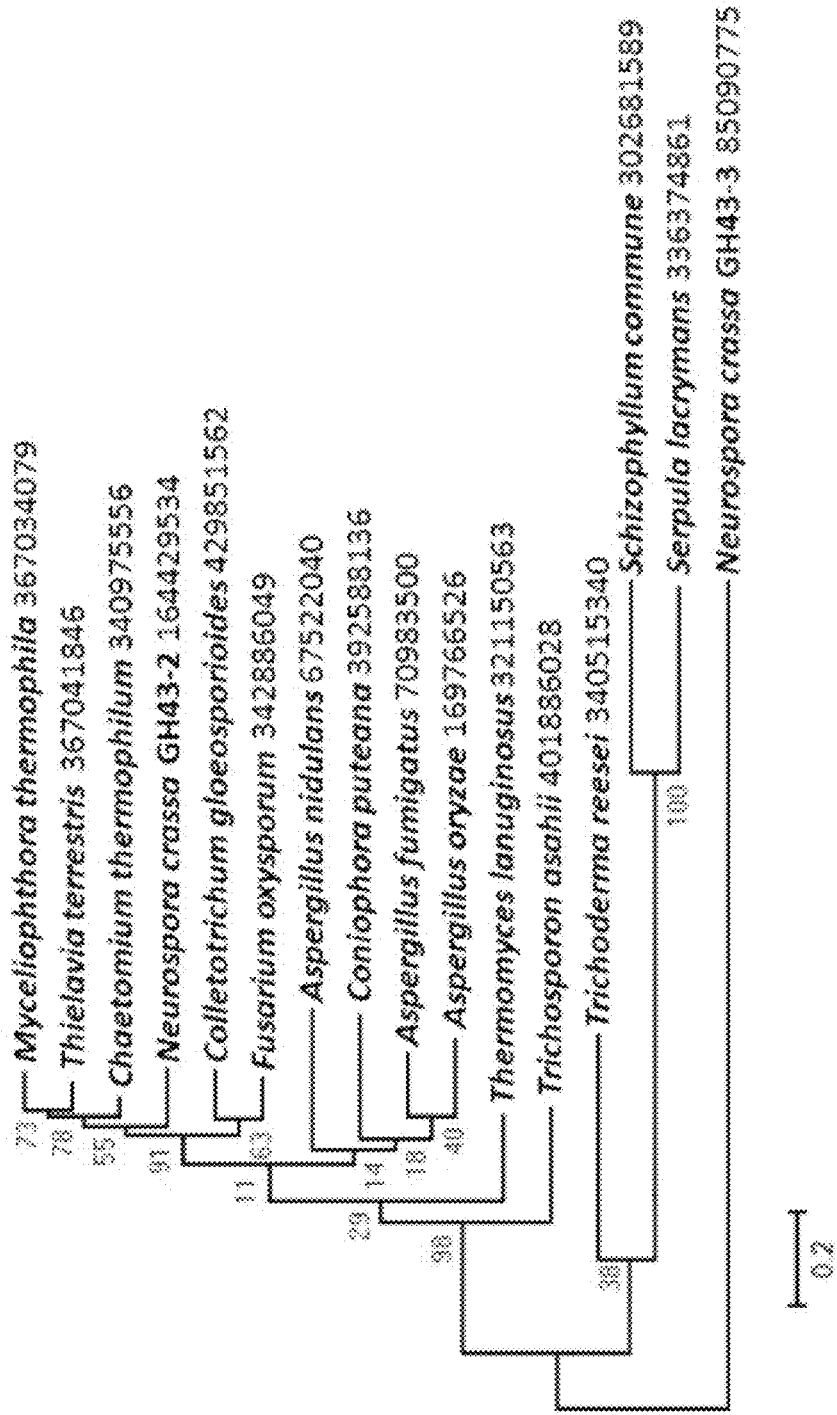
FIG. 21 illustrates the phylogenetic distribution of predicted intracellular β-xylosidases GH43-2 in filamentous fungi. Homologs of GH43-2 (NCU01900) were found with BLAST (Altschul et al. 1997) queries of respective sequence against NCBI protein database. Representative sequences from a diversified taxonomy were chosen and aligned with the MUSCLE algorithm (Edgar 2004). A maximum likelihood phylogenetic tree was calculated based on the alignment with the Jones-Taylor-Thornton model by using software MEGA v6.05 (Tamura et al. 2013). Xylan-induced extracellular GH43-3 (NCU05965) was used as an outgroup. The NCBI GI numbers of the sequences used to build the phylogenetic tree were indicated besides the species names. 1000 bootstrap replicates were performed to calculate the supporting values shown on the branches. The scale bar indicates 0.2 substitutions per amino acid residue.
Figure 22:
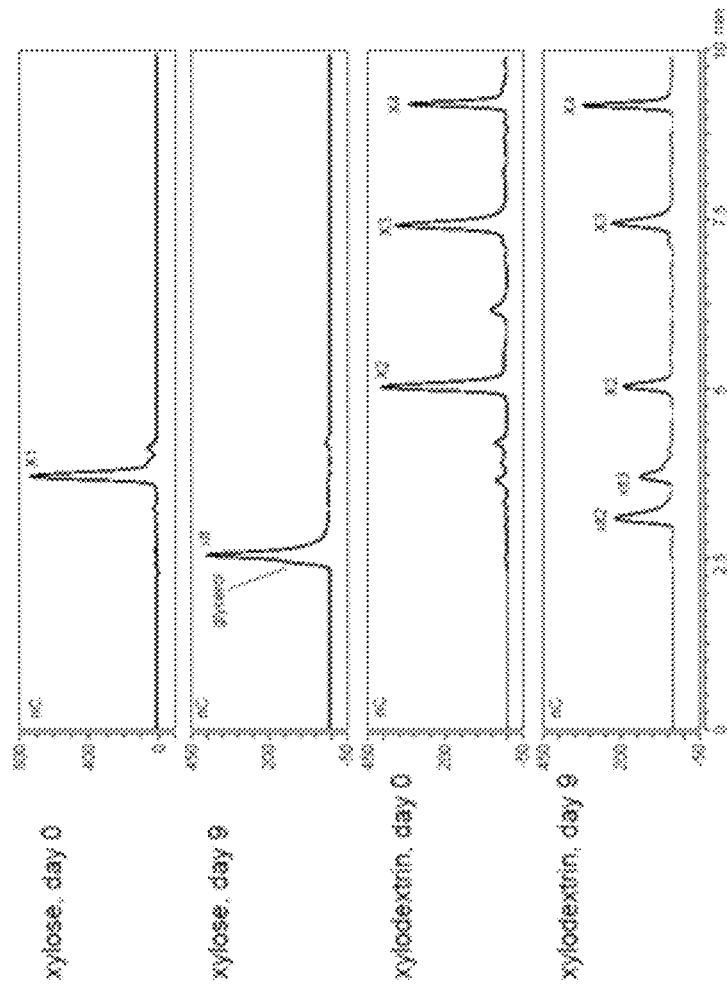
FIG. 22 illustrates carbohydrates from culture supernatants of strain SR8U expressing CDT-2 and GH43-2 (plasmid pXD8.4), resolved by HPAEC, abbreviated as follows: X1, xylose; X2, xylobiose; X3, xylotriose; X4, xylotetraose; xlt, xylitol; xlt2, xylosyl-xylitol; xlt3, xylosyl-xylosyl-xylitol.

In contrast to *S. cerevisiae*, many cellulolytic fungi including *Neurospora crassa* (Tian et al. 2009) naturally grow well on the cellulose and hemicellulose components of the plant cell wall. By using transcription profiling data (Tian et al. 2009) and by analyzing growth phenotypes of *N. crassa* knockout strains, Applicants identified separate pathways used by *N. crassa* to consume cellodextrins (Galazka et al. 2010) and xylodextrins released by its secreted enzymes (FIG. 18A and FIG. 18B). A strain carrying a deletion of a previously-identified cellodextrin transporter (CDT-2, NCU08114) (Galazka et al. 2010) was unable to grow on xylan (FIG. 19), and xylodextrins remained in the culture supernatant (See FIG. 7). As a direct test of transport function of CDT-2, *S. cerevisiae* strains expressing cdt-2 were able to import xylobiose, xylotriose and xylotetraose (See FIG. 1). Notably, *N. crassa* expresses a putative intracellular β-xylosidase, GH43-2 (NCU01900), when grown on xylan (Sun et al. 2012). Purified GH43-2 displayed robust hydrolase activity towards xylodextrins with a degree of polymerization (DP) spanning from 2 to 8, and with a pH optimum near 7 (FIG. 20A, FIG. 20B). The results with CDT-2 and GH43-2 confirm those obtained independently in (Cai et al. 2014). As with cdt-1, orthologues of cdt-2 are widely distributed in the fungal kingdom (Galazka et al. 2010), suggesting that many fungi consume xylodextrins derived from plant cell walls. Furthermore, as with intracellular β-glucosidases (Galazka et al. 2010), intracellular β-xylosidases are also widespread in fungi (Sun et al. 2012) (FIG. 21).

Cellodextrins and xylodextrins derived from plant cell walls are not catabolized by wild-type *S. cerevisiae* (Matsushika et al. 2009; Galazka et al. 2010; Young, Lee, and Alper 2010). Reconstitution of a cellodextrin transport and consumption pathway from *N. crassa* in *S. cerevisiae* enabled this yeast to ferment cellobiose (Galazka et al. 2010). Applicants therefore reasoned that expression of a functional xylodextrin transport and consumption system from *N. crassa* might further expand the capabilities of *S. cerevisiae* to utilize plant-derived xylodextrins. Previously, *S. cerevisiae* was engineered to consume xylose by introducing xylose isomerase (XI), or by introducing xylose reductase (XR) and xylitol dehydrogenase (XDH) (Jeffries 2006; van Maris et al. 2007; Matsushika et al. 2009). To test whether *S. cerevisiae* could utilize xylodextrins, a *S. cerevisiae* strain was engineered with the XR/XDH pathway derived from *Scheffersomyces stipitis*—similar to that in *N. crassa* (Sun et al. 2012)—and a xylodextrin transport (CDT-2) and consumption (GH43-2) pathway from *N. crassa*. The xylose utilizing yeast expressing CDT-2 along with the intracellular β-xylosidase GH43-2 was able to directly utilize xylodextrins with DPs of 2 or 3 (See FIG. 2A, FIG. 3A-FIG. 3D).

Notably, although high cell density cultures of the engineered yeast were capable of consuming xylodextrins with DPs up to 5, xylose levels remained high (See FIG. 2B), suggesting the existence of severe bottlenecks in the engineered yeast. These results are similar to those of a previous attempt to engineer *S. cerevisiae* for xylodextrin consumption, in which xylose was reported to accumulate in the culture medium (Fujii et al. 2011). Analyses of the supernatants from cultures of the yeast strains expressing CDT-2, GH43-2 and the *S. stipitis* XR/XDH pathway surprisingly revealed that the xylodextrins were converted into xylosyl-xylitol oligomers, a set of previously unknown compounds, rather than hydrolyzed to xylose and consumed (See FIG. 16, FIG. 4A-FIG. 4B, FIG. 22). The resulting xylosyl-xylitol oligomers were effectively dead-end products that could not be metabolized further.

Since the production of xylosyl-xylitol oligomers as intermediate metabolites has not been reported, the molecular components involved in their generation were examined To test whether the xylosyl-xylitol oligomers resulted from side reactions of xylodextrins with endogenous *S. cerevisiae* enzymes, Applicants used two separate yeast strains in a combined culture, one containing the xylodextrin hydrolysis pathway composed of CDT-2 and GH43-2, and the second with the XR/XDH xylose consumption pathway. The strain expressing CDT-2 and GH43-2 would cleave xylodextrins to xylose, which could then be secreted via endogenous transporters (Hamacher et al. 2002) and serve as a carbon source for the strain expressing the xylose consumption pathway (XR and XDH). The engineered yeast expressing XR and XDH is capable of consuming xylose (See FIG. 2A). When co-cultured, these strains consumed xylodextrins without producing the xylosyl-xylitol byproduct (See FIG. 5). These results suggest that endogenous yeast enzymes and GH43-2 transglycolysis activity are not responsible for generating the xylosyl-xylitol byproducts, and suggest that they must be generated by the XR from *S. stipitis* (SsXR).

Fungal xylose reductases such as SsXR have been widely used in industry for xylose fermentation. However, the structural details of substrate binding to the XR active site have not been established. To explore the molecular basis for XR reduction of oligomeric xylodextrins, the structure of *Candida tenuis* xylose reductase (CtXR) (Kavanagh et al. 2002), a close homologue of SsXR, was analyzed. CtXR contains an open active site cavity where xylose could bind, located near the binding site for the NADH co-factor (Kavanagh et al. 2002; Kratzer et al. 2006). Notably, the open shape of the active site can readily accommodate the binding of longer xylodextrin substrates (FIG. 17). Using computational docking algorithms (Trott and Olson 2010), xylobiose was found to fit well in the pocket. Furthermore, there are no obstructions in the protein that would prevent longer xylodextrin oligomers from binding (FIG. 17).

Figure 23:
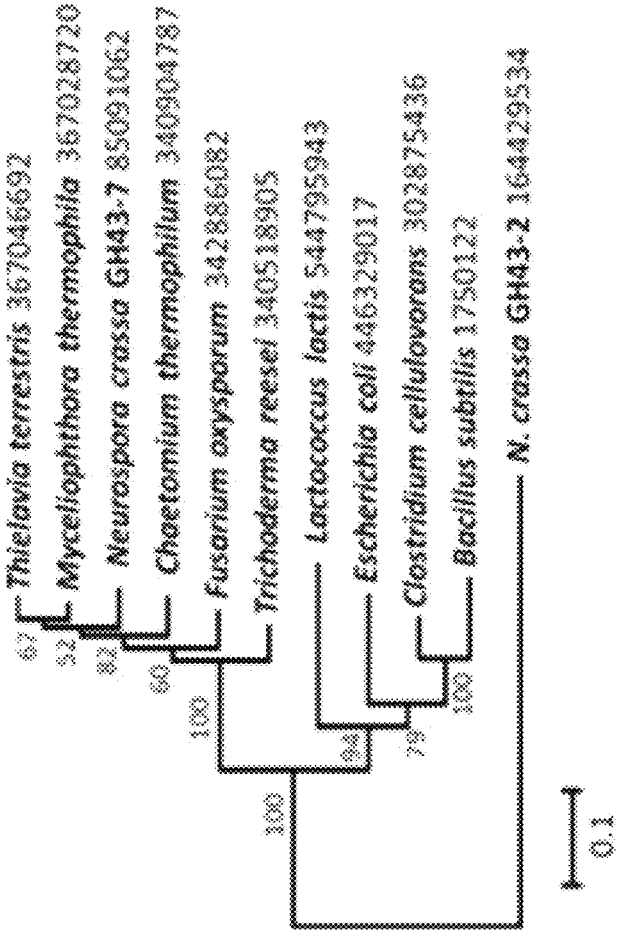
FIG. 23 illustrates phylogeny of GH43-7. N. crassa GH43-2 was used as an outgroup. 1000 bootstrap replicates were performed to calculate the supporting values shown on the branches. The scale bar indicates 0.1 substitutions per amino acid residue. The NCBI GI numbers of the sequences used to build the phylogenetic tree are indicated beside the species names.

Applicants reasoned that if the xylosyl-xylitol byproducts are generated by fungal XRs like that from *S. stipitis*, similar side products should be generated in *N. crassa*, thereby requiring an additional pathway for their consumption. Consistent with this hypothesis, xylose reductase XYR-1 (NCU08384) from *N. crassa* also generated xylosyl-xylitol products from xylodextrins (See FIG. 6A-FIG. 6B). However, when *N. crassa* was grown on xylan, no xylosyl-xylitol byproduct accumulated in the culture medium (See FIG. 7). Thus, *N. crassa* presumably expresses an additional enzymatic activity to consume xylosyl-xylitol oligomers. Consistent with this hypothesis, a second putative intracellular β-xylosidase upregulated when *N. crassa* was grown on xylan, GH43-7 (NCU09625) (Sun et al. 2012), had weak β-xylosidase activity but rapidly hydrolyzed xylosyl-xylitol into xylose and xylitol (See FIG. 8A-FIG. 8B). The newly-identified β-xylosidase GH43-7, capable of metabolizing xylosyl-xylitol, is widely distributed in fungi and bacteria (See FIG. 11, FIG. 23), suggesting that it is used by a variety of microbes in the consumption of xylodextrins. Indeed, GH43-7 enzymes from the bacteria *Bacillus subtilis* and *Escherichia coli* cleave both xylodextrin and xylosyl-xylitol (See FIG. 15).

Figure 24A:
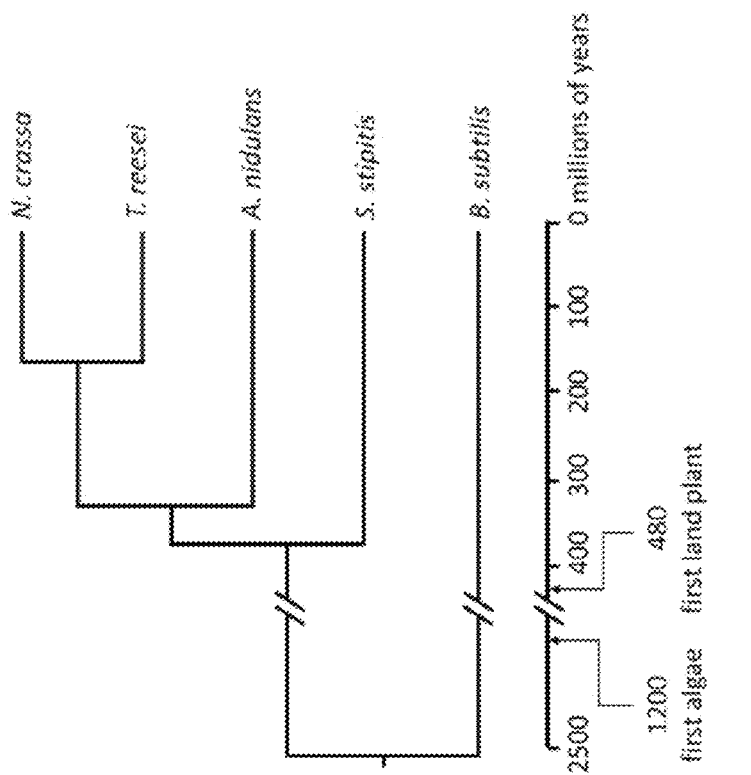
FIG. 24A-FIG. 24B illustrate xylosyl-xylitol and xylosyl-xylosyl-xylitol production by a range of microbes.
Figure 24B:
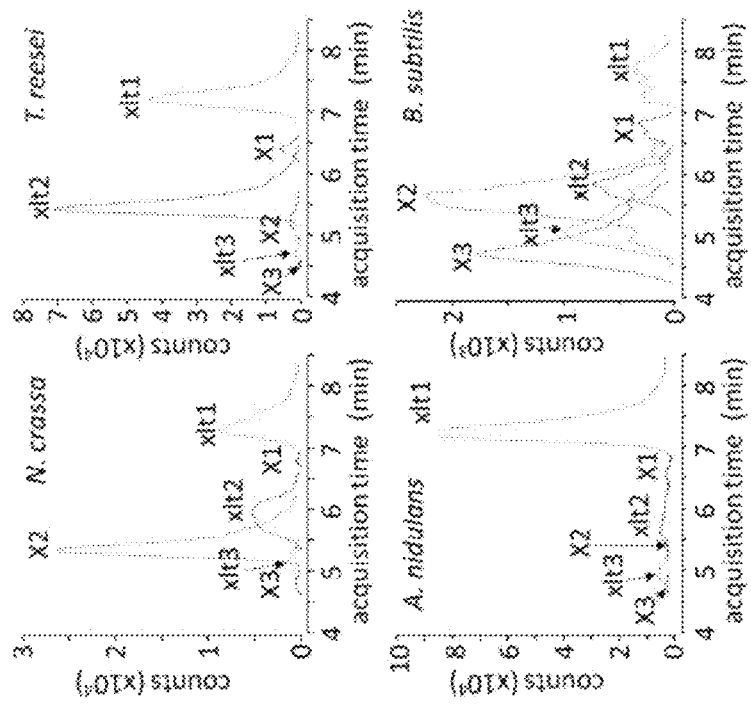
Figure 25:
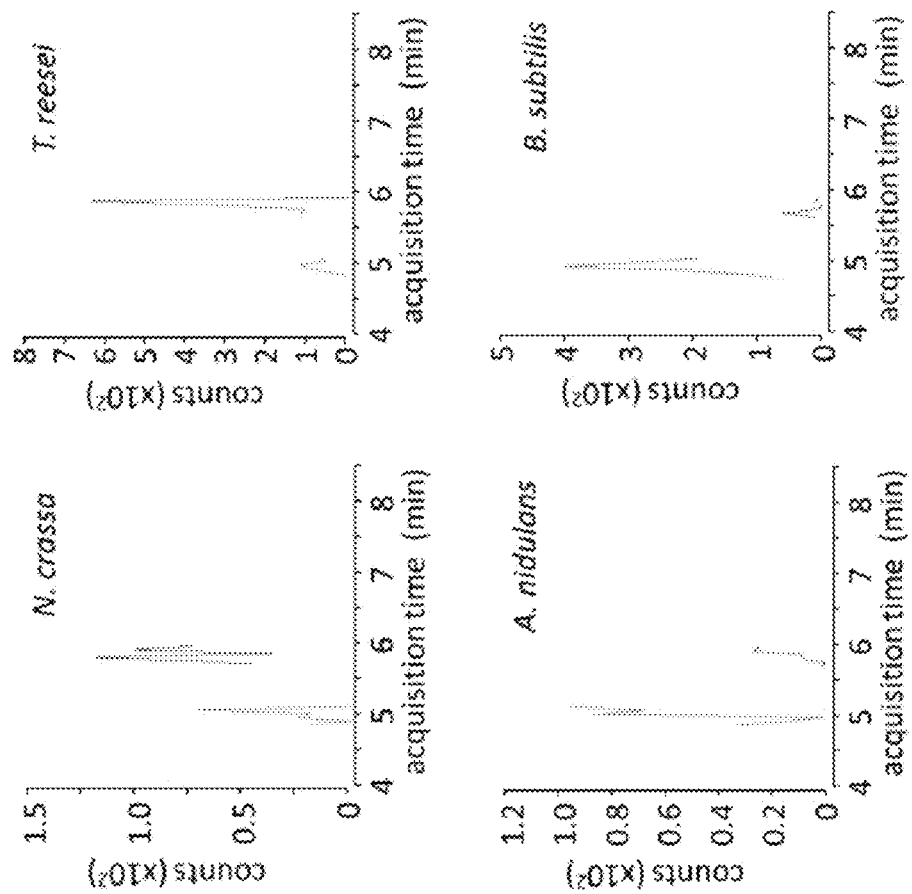
FIG. 25 illustrates LC-MS/MS multiple reaction monitoring chromatograms of xylosyl-xylitols from cultures of microbes grown on xylodextrins. Shown are MS/MS transitions for xylosyl-xylitol (in red, m/z 283.1035→151.0612 transition) and xylosyl-xylosyl-xylitol (in green, m/z 415.1457→151.0612 transition) analyzed from intracellular metabolites of N. crassa, T reesei, A. nidulans and B. subtilis grown on xylodextrins, after separation by liquid chromatography.
Figure 26:
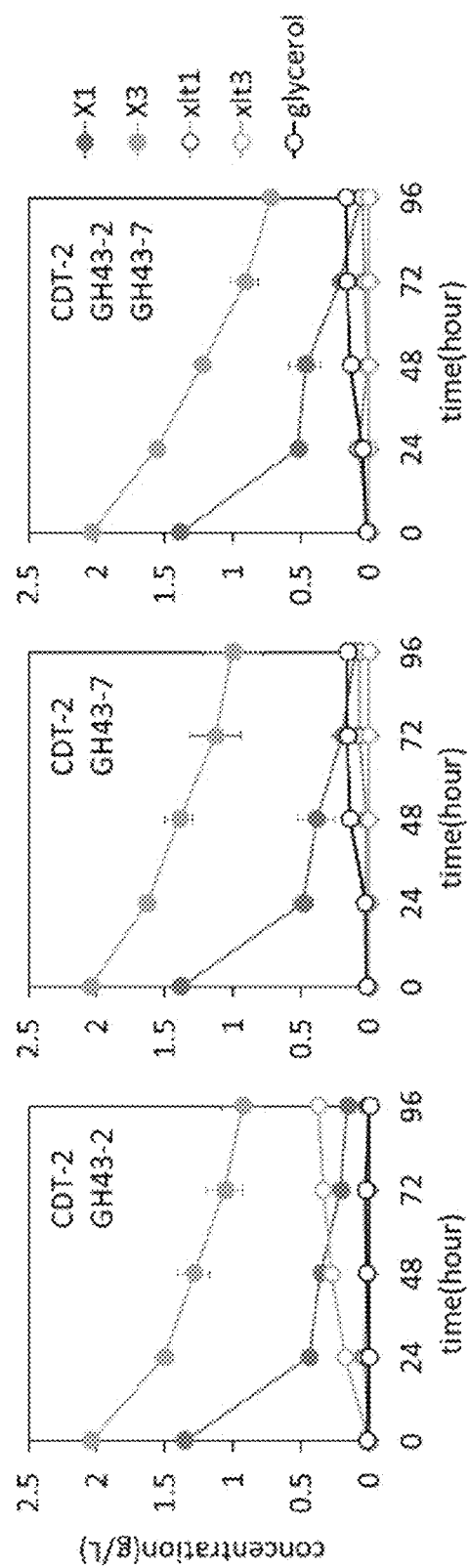
FIG. 26 illustrates carbohydrate and their derivatives profiling during yeast growth on xylodextrin. Yeast growth with xylodextrin as the sole carbon source (concentration g/L) under aerobic conditions with a cell density at OD600=20. Yeast strain SR8 transformed with plasmid expressing CDT-2 and GH43-2 (pXD8.4), CDT-2 and GH43-7 (pXD8.6), or all three genes (pXD8.7). All growth experiments were performed in biological triplicate and error bars indicate the standard deviation between experiments.

To test whether xylosyl-xylitol is produced generally by microbes as an intermediary metabolite during their growth on hemicellulose, Applicants extracted and analyzed the metabolites from a number of ascomycetes species and *B. subtilis* grown on xylodextrins. Notably, these widely-divergent fungi and *B. subtilis* all produce xylosyl-xylitols when grown on xylodextrins (FIG. 24A and FIG. 25). These organisms span over 1 billion years of evolution (FIG. 24B), indicating that the use of xylodextrin reductases to consume plant hemicellulose is widespread.

It was next tested whether integration of the complete xylodextrin consumption pathway would overcome the poor xylodextrin utilization by *S. cerevisiae* (See FIG. 2A-FIG. 2B) (Fujii et al. 2011). When combined with the original xylodextrin pathway (CDT-2 plus GH43-2), GH43-7 enabled *S. cerevisiae* to grow more rapidly on xylodextrin (See FIG. 9A) and eliminated accumulation of xylosyl-xylitol intermediates (See FIG. 9B-FIG. 9D, FIG. 10 and FIG. 26). The presence of xylose and glucose greatly improved anaerobic fermentation of xylodextrins (FIG. 27A-FIG. 27B, FIG. 28, and FIG. 29A-FIG. 29B), indicating that metabolic sensing in *S. cerevisiae* with the complete xylodextrin pathway may require additional tuning (Youk and van Oudenaarden 2009) for optimal xylodextrin fermentation. Taken together, these results reveal the XR/XDH pathway widely used in engineered *S. cerevisiae* naturally has broad substrate specificity for xylodextrins, and complete reconstitution of the naturally occurring xylodextrin pathway allows *S. cerevisiae* to efficiently consume xylodextrins.

Figure 27:
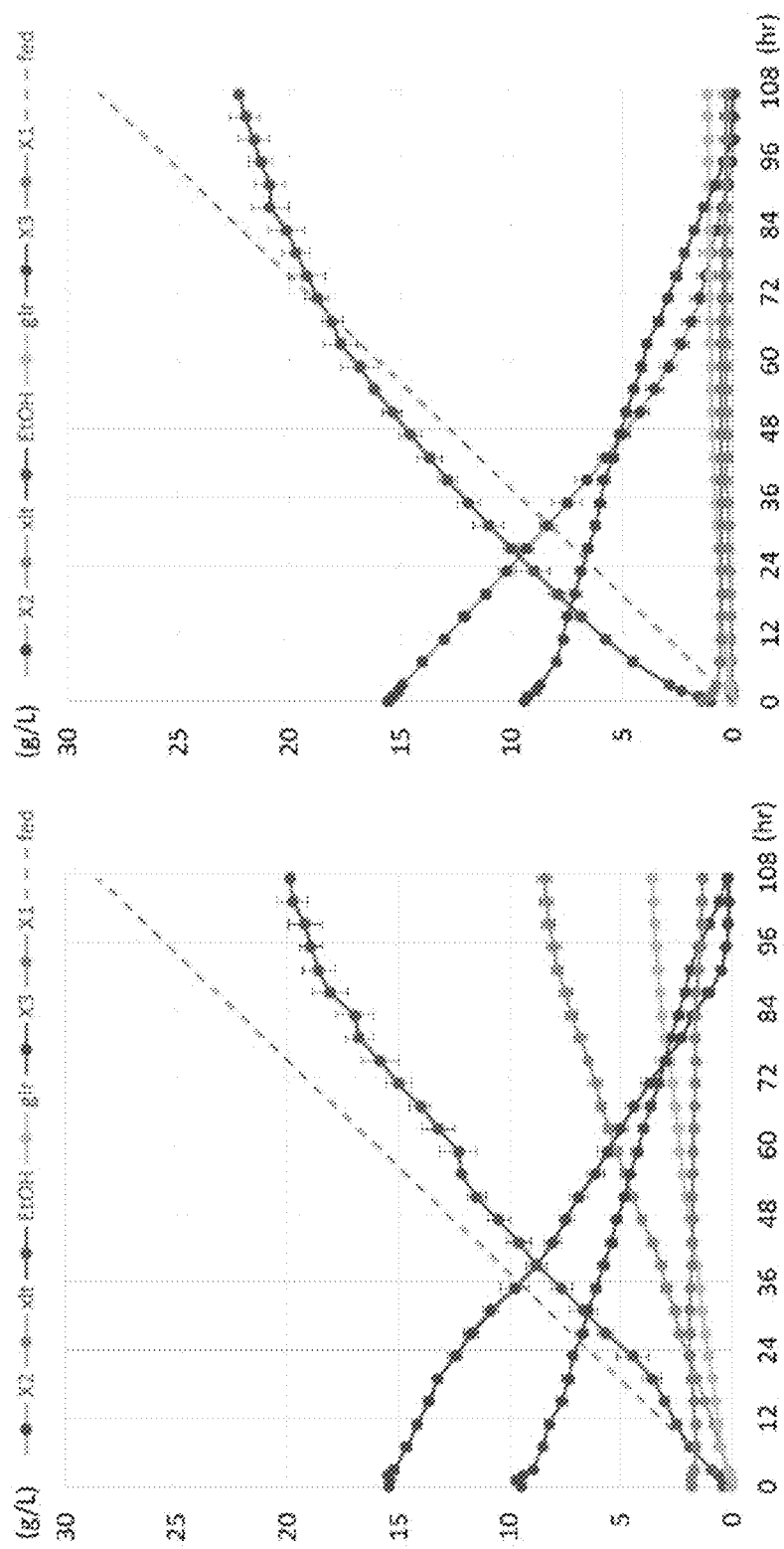
FIG. 27A-FIG. 27B illustrate anaerobic fermentation of xylodextrins in co-fermentations with xylose or glucose.
Figure 28:
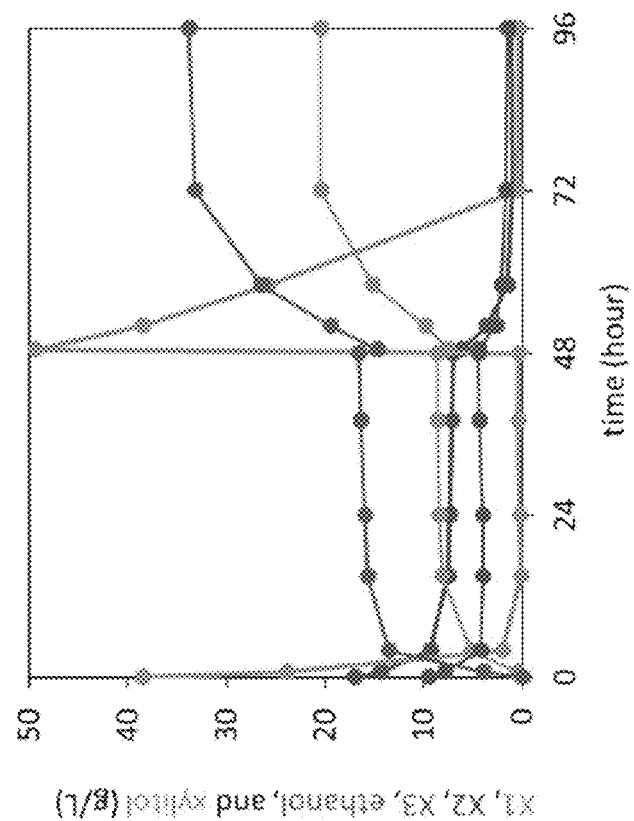
FIG. 28 illustrates anaerobic xylodextrin utilization in the presence of xylose. Strain carrying the complete xylodextrin pathway (CDT-2, GH43-2, GH43-7, XR/XDH) was grown under anaerobic conditions in oMM media (Lin et al. 2014) containing 4% xylose and 3% xylodextrin. The consumption of xylobiose (X2) and xylotriose (X3) stalled when xylose (X1) was depleted and resumed after supplying additional xylose at hour 48.
Figure 29:
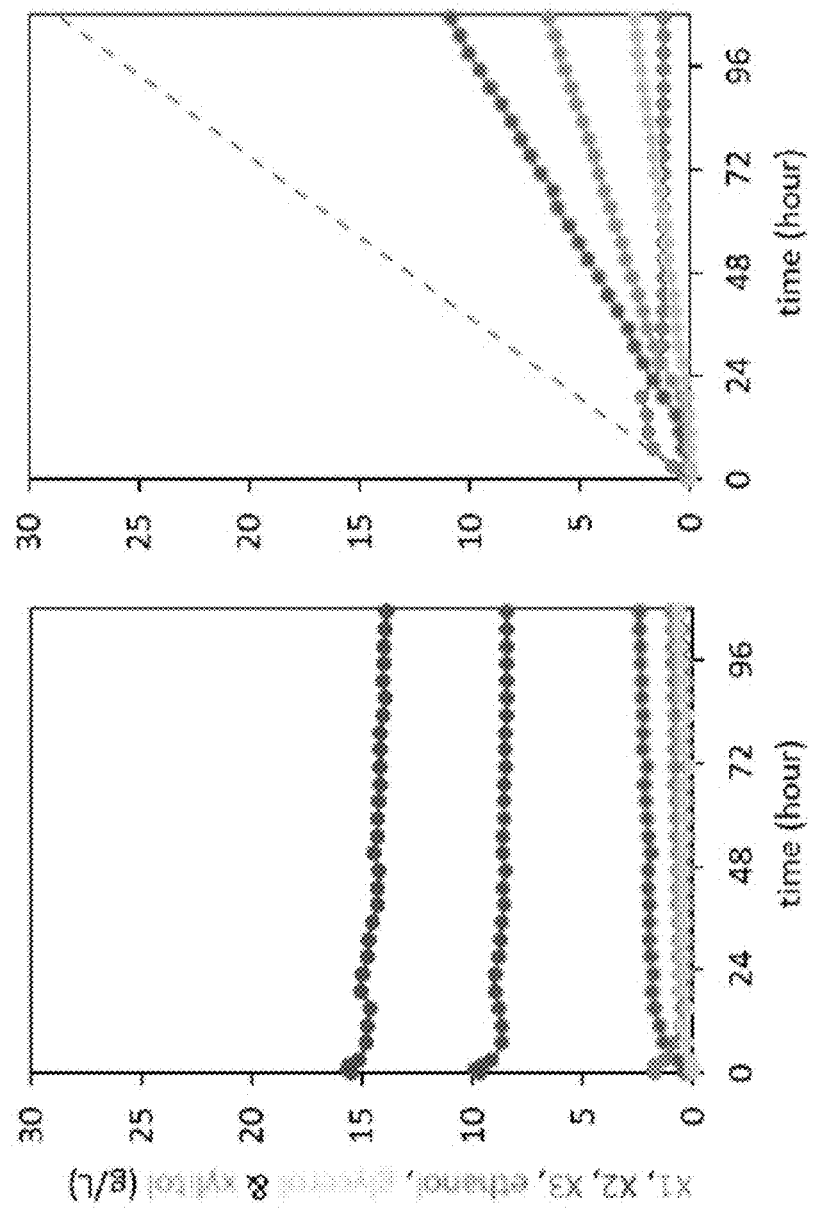
FIG. 29A-FIG. 29B illustrate control anaerobic fermentations with S. cerevisiae strain expressing the complete xylodextrin utilization pathway. Strain SR8 with plasmid pXD8.7 expressing CDT-2, GH43-2, and GH43-7 was used at an initial OD600 of 20. Solid lines represent concentrations of compounds in the media. Blue dotted line shows the total amount of xylose added to the culture over time.
Figure 30:
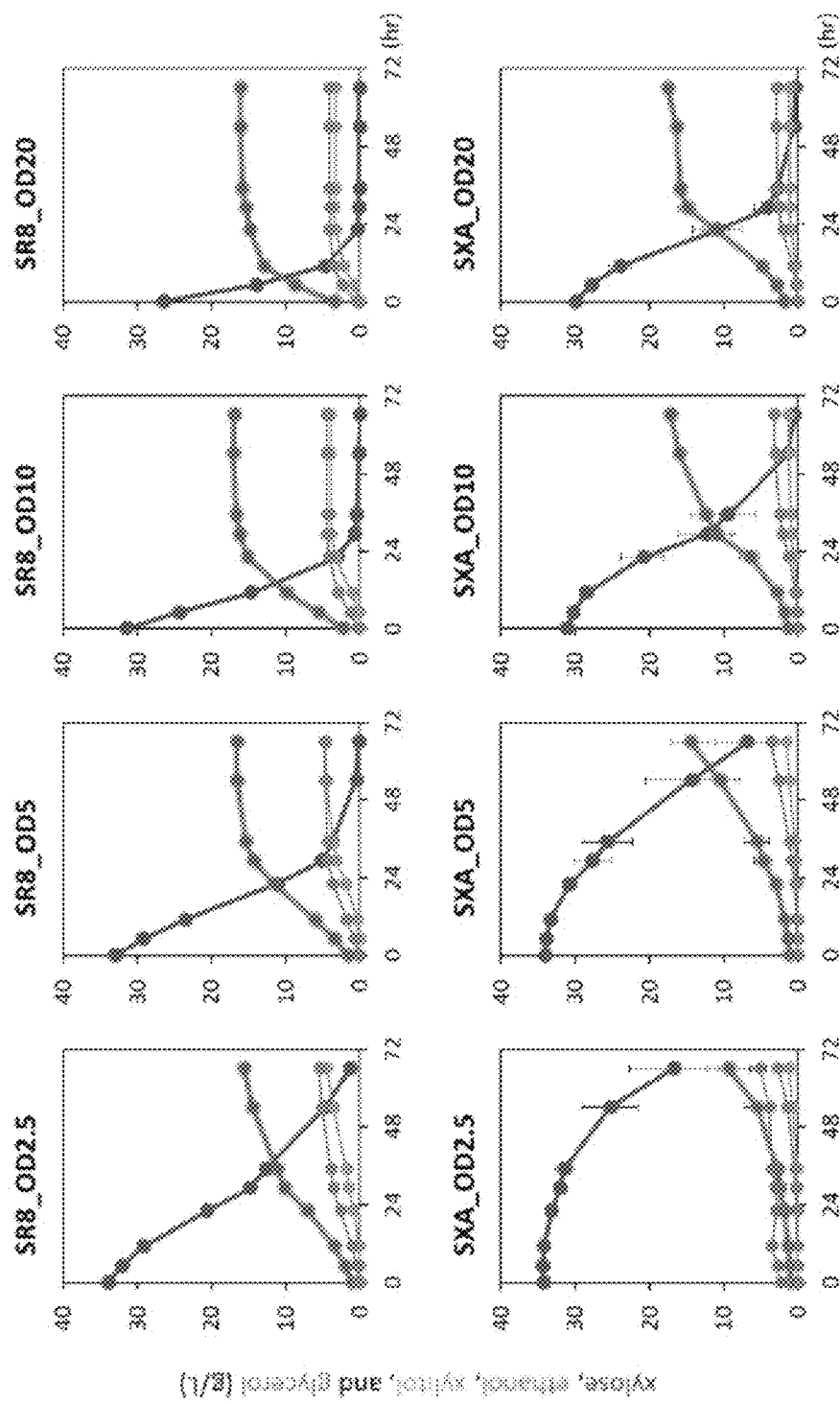
FIG. 30 illustrates a comparison of XI and XR/XDH pathway fermentation performance Xylose fermentations using strain SR8 (XR/XDH pathway) and strain SXA-R2P-E (XI pathway) with different starting cell loadings are shown. The medium used in these fermentations was oMM. Vertical axis, g/L; horizontal axis, time in hours.
Figure 31:
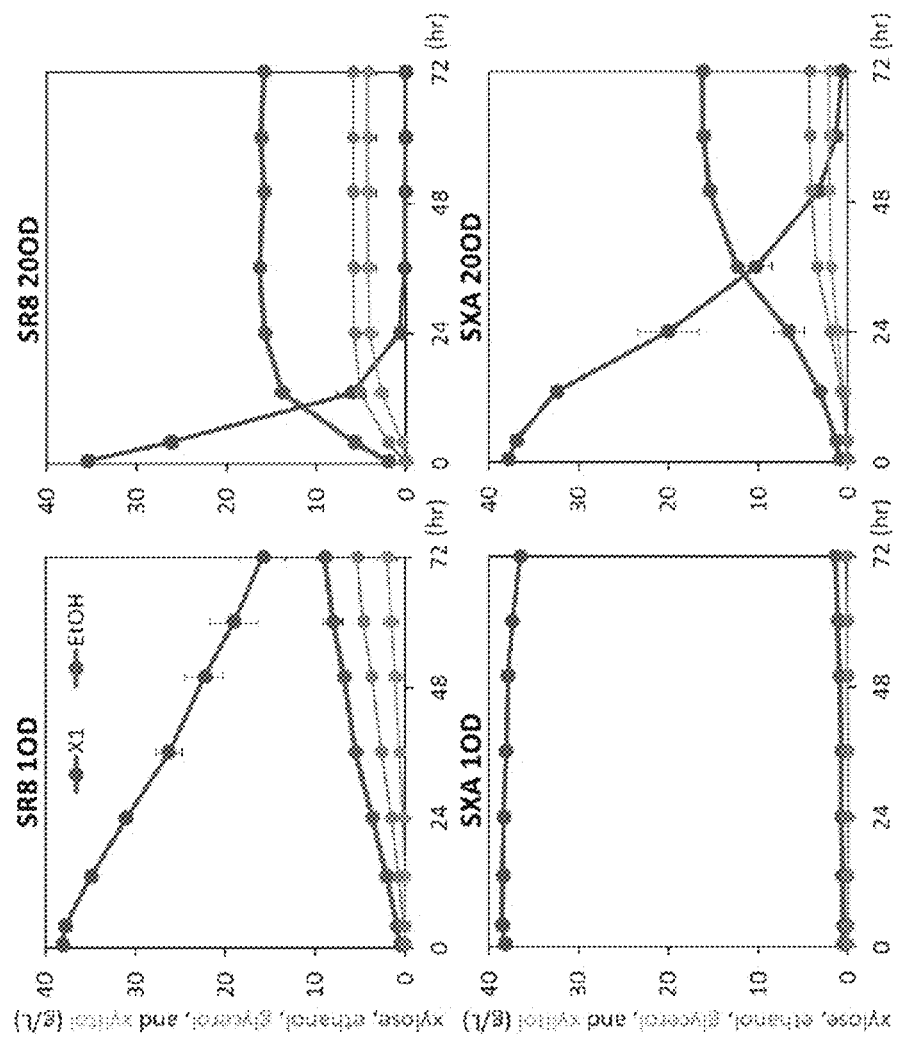
FIG. 31 illustrates xylose fermentation performance of strains SR8 (XR/XDH) and SXA-R2P-E (XI), using log-phase cultures as fermentation seeds. The strain and starting OD600 values are indicated above each panel. The medium used in these fermentations was oMM. Vertical axis, g/L; horizontal axis, time in hours.
Figure 32:
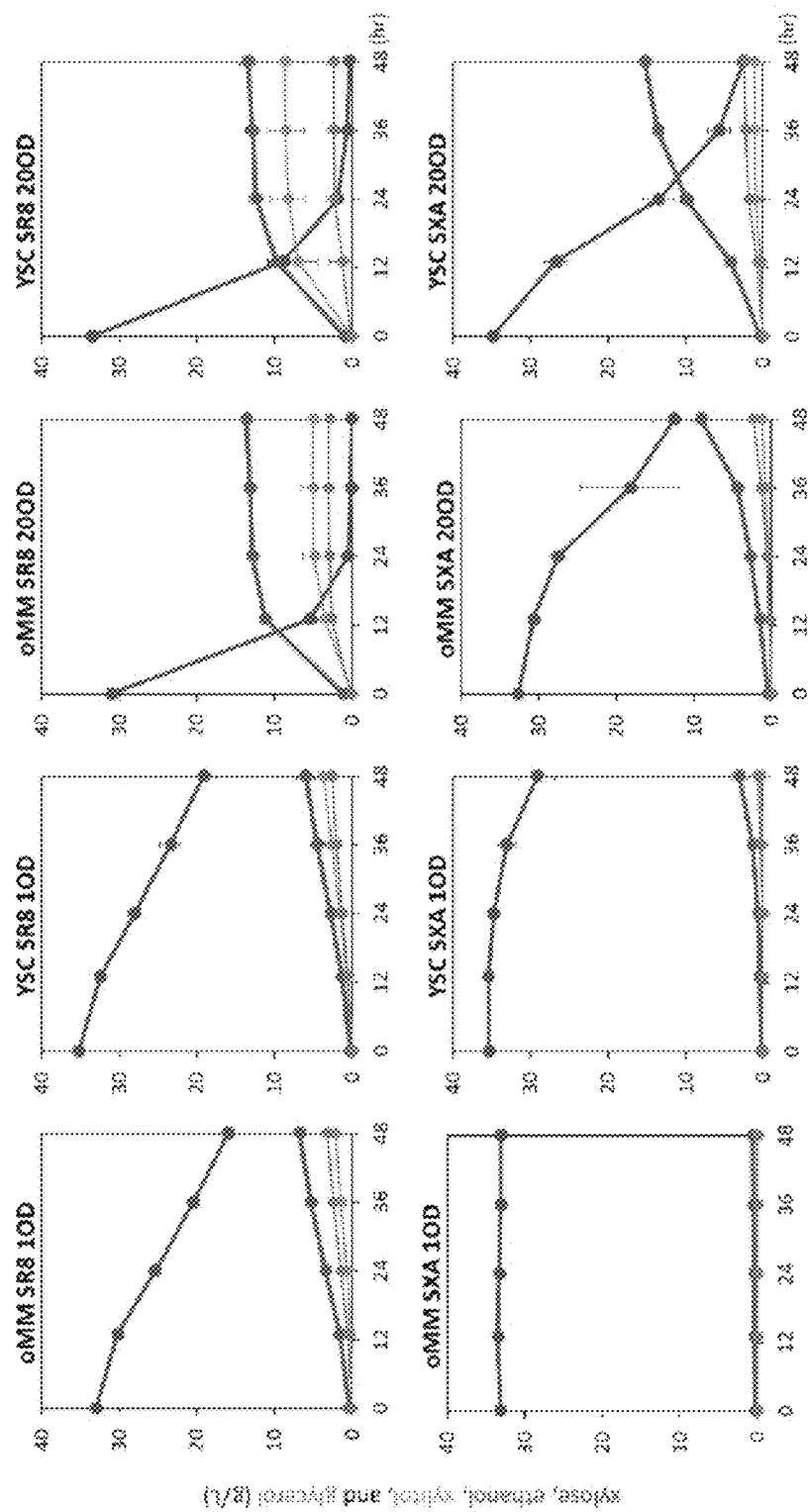
FIG. 32 illustrates xylose fermentation performance of strains SR8 (XR/XDH) and SXA-R2P-E (XI), using either oMM or YSC medium. The media, strain, and starting OD600 values are given above each panel. Vertical axis, g/L; horizontal axis, time in hours.

It has been proposed that the optimal means for fermenting xylose into biofuels would use XI instead of the XR/XDH pathway (van Maris et al. 2007; Zhou et al. 2012; Lee, Jellison, and Alper 2014). Although XI could in principle replace the XR/XDH part of the xylodextrin consumption pathway for producing intracellular xylulose, no clear comparisons of the best yeast strains engineered to use XI or XR/XDH have been published (Karhumaa et al. 2007). Applicants therefore compared two of the best-performing engineered yeast strains in the public domain; strain SR8, which uses XR/XDH (Kim et al. 2013) and strain SXA-R2P-E, which uses XI (Lee, Jellison, and Alper 2014), in anaerobic xylose fermentations. Over a range of cell loadings (2.5-20 OD600), strain SR8 expressing XR/XDH displayed much higher rates of ethanol production when compared to strain SXA-R2P-E expressing XI (FIG. 30, Table 2). This result was true with seed cultures prepared from mid-log or late-log cultures, and in two different defined media (Lin et al. 2014; Lee, Jellison, and Alper 2014) (FIG. 31). By contrast, strain SXA-R2P-E had slightly higher ethanol yields and produced less xylitol as a byproduct (FIG. 30, Table 2, and FIG. 31). Notably, it was observed that the XR/XDH pathway produced much less xylitol when xylodextrins were used in fermentations than from xylose (FIG. 27A-FIG. 27B and FIG. 29B). Thus, xylodextrin consumption by means of the XR/XDH pathway could result in yeast strains with both high ethanol productivity and yield without xylitol formation.

TABLE 2

Fermentation performance of the two xylose utilizing *S. cerevisiae* strains

| Medium[1] | Seed condition | Strain | Xylose consumption rate[2] (g xylose · g cells$^{-1}$ · h$^{-1}$) | Ethanol production rate[2] (g ethanol · g cells$^{-1}$ · h$^{-1}$) | Ethanol yield[3] (g ethanol · g xylose$^{-1}$) |
|---|---|---|---|---|---|
| oMM | middle-log phase, 20 OD | SR8 | 0.304 | 0.123 | 0.392 |

TABLE 2-continued

Fermentation performance of the two xylose utilizing *S. cerevisiae* strains

| Medium[1] | Seed condition | Strain | Xylose consumption rate[2] (g xylose · g cells$^{-1}$ · h$^{-1}$) | Ethanol production rate[2] (g ethanol · g cells$^{-1}$ · h$^{-1}$) | Ethanol yield[3] (g ethanol · g xylose$^{-1}$) |
|---|---|---|---|---|---|
| oMM | middle-log phase, 20 OD | SXA-R2p-E | 0.133 | 0.056 | 0.412 |
| oMM | middle-log phase, 1 OD | SR8 | 0.905 | 0.358 | 0.377 |
| oMM | middle-log phase, 1 OD | SXA-R2p-E | — | — | — |
| oMM | late-log phase, 2.5 OD | SR8 | 0.339 | 0.146 | 0.360 |
| oMM | late-log phase, 2.5 OD | SXA-R2p-E | — | — | — |
| oMM | late-log phase, 5 OD | SR8 | 0.293 | 0.144 | 0.369 |
| oMM | late-log phase, 5 OD | SXA-R2p-E | 0.169 | 0.09 | 0.402 |
| oMM | late-log phase, 10 OD | SR8 | 0.258 | 0.121 | 0.378 |
| oMM | late-log phase, 10 OD | SXA-R2p-E | 0.2 | 0.106 | 0.419 |
| oMM | late-log phase, 20 OD | SR8 | 0.237 | 0.102 | 0.390 |
| oMM | late-log phase, 20 OD | SXA-R2p-E | 0.108 | 0.052 | 0.430 |
| YSC | late-log phase, 1 OD | SR8 | 0.88 | 0.305 | 0.358 |
| YSC | late-log phase, 1 OD | SXA-R2p-E | — | — | — |
| YSC | late-log phase, 20 OD | SR8 | 0.219 | 0.078 | 0.378 |
| YSC | late-log phase, 20 OD | SXA-R2p-E | 0.108 | 0.048 | 0.453 |

[1]Fermentations were carried out anaerobically in batch conditions using flasks and 40 g/L xylose.
[2]Maximal values in g of xylose or ethanol per g of cell dry weight per hour.
[3]Grams of ethanol yield per g of xylose.

Figure 33A:
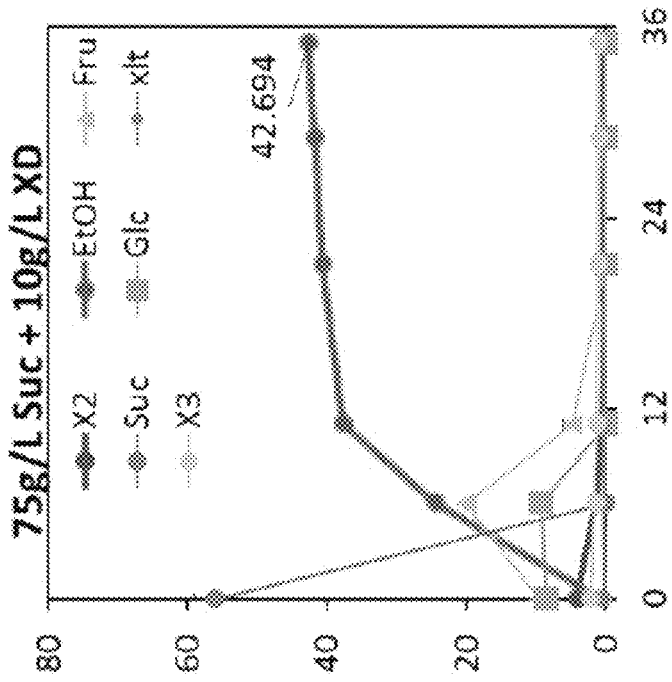
FIG. 33A-FIG. 33B illustrate xylodextrin and sucrose co-fermentations.
Figure 33B:
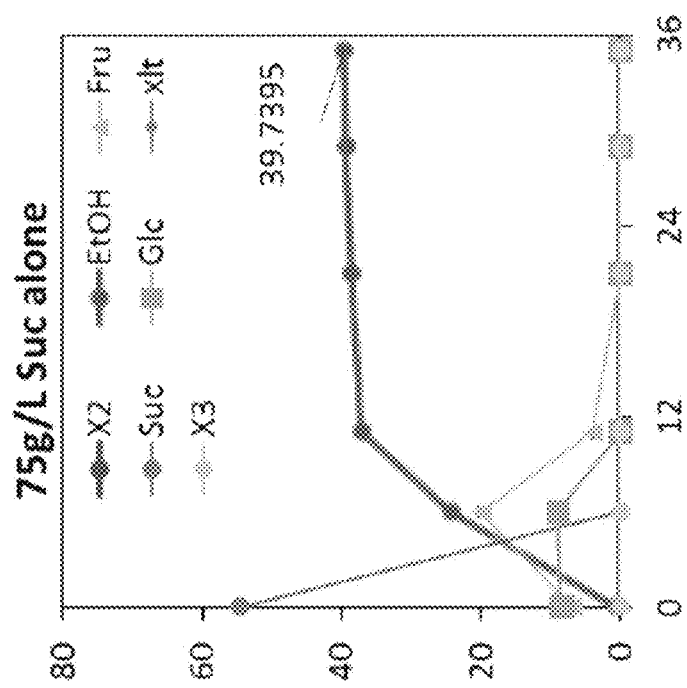

The observation that xylodextrin fermentation was stimulated by glucose (FIG. 27B) suggested that the xylodextrin pathway could serve more generally for cofermentations to enhance biofuel production. It was therefore tested whether xylodextrin fermentation could be carried out simultaneously with sucrose fermentation, as a means to augment ethanol yield from sugarcane. In this scenario, xylodextrins released by hot water treatment (Hendriks and Zeeman 2009; Agbor et al. 2011; Evangelina Vallejos et al. 2012) could be added to sucrose fermentations using yeast engineered with the xylodextrin consumption pathway. To test this, Applicants used strain SR8 engineered with the xylodextrin pathway (CDT-2, GH43-2, and GH43-7) in fermentations combining sucrose and xylodextrins. Applicants observed simultaneous fermentation of sucrose and xylodextrins, with increased ethanol yields (FIG. 33). Notably, the levels of xylitol production were found to be low (FIG. 33), as observed in cofermentations with glucose (FIG. 27B).

Using yeast as an exemplary platform, Applicants identified a xylodextrin consumption pathway in *N. crassa* (FIG. 12) that surprisingly involves a new metabolic intermediate widely produced by many fungi and bacteria. In bacteria such as *B. subtilis*, xylosyl-xylitol may be generated by aldo-keto reductases known to possess broad substrate specificity (Barski, Tipparaju, and Bhatnagar 2008). The discovery of the xylodextrin consumption pathway along with cellodextrin consumption (Galazka et al. 2010) in cellulolytic fungi for the two major sugar components of the plant cell wall now provides many modes of engineering yeast to ferment plant biomass-derived sugars (FIG. 12). The XR/XDH pathway may also provide significant advantages in realistic fermentation conditions with sugars derived from hemicellulose. The breakdown of hemicellulose, which is acetylated (Sun et al. 2012), releases highly-toxic acetate, degrading the performance of *S. cerevisiae* fermentations (Bellissimi et al. 2009; Sun et al. 2012). The excess reducing power generated by the XR/XDH pathway, initially deemed a problem, can be exploited to drive acetate reduction, thereby detoxifying the fermentation medium and increasing ethanol production (Wei et al. 2013).

With optimization, the newly-identified xylodextrin consumption pathway provides new opportunities to expand first-generation bioethanol production from cornstarch or sugarcane to include hemicellulose from the plant cell wall. For example, Applicants propose that xylodextrins released from the hemicellulose in sugarcane bagasse by using compressed hot water treatment (Hendriks and Zeeman 2009; Agbor et al. 2011; Evangelina Vallejos et al. 2012) could be directly fermented by yeast engineered to consume xylodextrins, as shown in the experiments described herein (FIG. 33). Xylodextrin consumption combined with glucose or cellodextrin consumption (FIG. 12) could also improve next-generation biofuel production from lignocellulosic feedstocks under a number of pretreatment scenarios (Hendriks and Zeeman 2009; Evangelina Vallejos et al. 2012). These pathways could find widespread use to overcome remaining bottlenecks to fermentation of lignocellulosic feedstocks as a sustainable and economical source of biofuels and renewable chemicals.

REFERENCES

D. C. Savage, Microbial ecology of the gastrointestinal tract. Annu Rev Microbiol 31, 107 (1977).

M. J. Vazquez, J. L. Alonso, H. Dominguez, J. C. Parajo, Xylooligosaccharides: manufacture and applications. Trends Food Sci Tech 11, 387 (November, 2000).

A. A. Aachary, S. G. Prapulla, Xylooligosaccharides (XOS) as an Emerging Prebiotic: Microbial Synthesis, Utilization, Structural Characterization, Bioactive Properties, and Applications. Compr Rev Food Sci F 10, 2 (January, 2011).

J. Schrezenmeir, M. de Vrese, Probiotics, prebiotics, and synbiotics—approaching a definition. American Journal of Clinical Nutrition 73, 361s (February, 2001).

G. R. Gibson, M. B. Roberfroid, Dietary modulation of the human colonic microbiota: introducing the concept of prebiotics. J Nutr 125, 1401 (June, 1995).

M. Okazaki, S. Fujikawa, N. Matsumoto, Effects of xylooligosaccharide on growth of bifidobacteria. Nippon Eiyo Shokuryo Gakkaishi=Journal of the Japanese Society of Nutrition and Food Science 43, 395 (1990).

C. K. Hsu, J. W. Liao, Y. C. Chung, C. P. Hsieh, Y. C. Chan, Xylooligosaccharides and fructooligosaccharides affect the intestinal microbiota and precancerous colonic lesion development in rats. J Nutr 134, 1523 (June, 2004).

A. Azarpazhooh, H. Limeback, H. P. Lawrence, P. S. Shah, Xylitol for preventing acute otitis media in children up to 12 years of age. Cochrane Database Syst Rev, CD007095 (2011).

A. Maguire, A. J. Rugg-Gunn, Xylitol and caries prevention—is it a magic bullet? Br Dent J 194, 429 (Apr. 26, 2003).

K. Mäkinen, Dietary prevention of dental caries by xylitol-clinical effectiveness and safety. J Appl Nutr 44, 16 (1992).

L. Hyvonen, P. Koivistoinen, F. Voirol, Food Technological Evaluation of Xylitol. Adv Food Res 28, 373 (1982).

T. B. Granström, K. Izumori, M. Leisola, A rare sugar xylitol. Part II: biotechnological production and future applications of xylitol. Applied microbiology and biotechnology 74, 273 (2007).

A. Carroll, C. Somerville, Cellulosic biofuels. *Annual Review of Plant Biology* 60, 165 (2009).

S. P. Chundawat, G. T. Beckham, M. E. Himmel, B. E. Dale, Deconstruction of lignocellulosic biomass to fuels and chemicals. *Annual Review of Chemical and Biomolecular Engineering* 2, 121 (2011).

C. Somerville et al., Toward a systems approach to understanding plant cell walls. Science 306, 2206 (2004).

M. E. Himmel et al., Biomass recalcitrance: engineering plants and enzymes for biofuels production. Science 315, 804 (2007).

L. R. Jarboe et al., Metabolic engineering for production of biorenewable fuels and chemicals: contributions of synthetic biology. Journal of Biomedicine & Biotechnology 2010, 761042 (2010).

L. R. Lynd, P. J. Weimer, W. H. van Zyl, I. S. Pretorius, Microbial cellulose utilization: fundamentals and biotechnology. Microbiology and Molecular Biology Reviews 66, 506 (2002).

K. K. Hong, J. Nielsen, Metabolic engineering of *Saccharomyces cerevisiae*: a key cell factory platform for future biorefineries. Cellular and Molecular Life Sciences 69, 2671 (2012).

S. J. Ha et al., Engineered *Saccharomyces cerevisiae* capable of simultaneous cellobiose and xylose fermentation. Proceedings of the National Academy of Sciences of the United States of America 108, 504 (2011).

M. Kuyper et al., Metabolic engineering of a xylose-isomerase-expressing *Saccharomyces cerevisiae* strain for rapid anaerobic xylose fermentation. FEMS Yeast Research 5, 399 (2005).

E. M. Young, A. Tong, H. Bui, C. Spofford, H. S. Alper, Rewiring yeast sugar transporter preference through modifying a conserved protein motif. Proceedings of the National Academy of Sciences of the United States of America 111, 131 (2014).

T. W. Jeffries, Engineering yeasts for xylose metabolism. Current Opinion in Biotechnology 17, 320 (2006).

C. Tian et al., Systems analysis of plant cell wall degradation by the model filamentous fungus *Neurospora crassa*. Proceedings of the National Academy of Sciences of the United States of America 106, 22157 (2009).

J. M. Galazka et al., Cellodextrin transport in yeast for improved biofuel production. Science 330, 84 (2010).

J. Sun, C. Tian, S. Diamond, N. L. Glass, Deciphering transcriptional regulatory mechanisms associated with hemicellulose degradation in *Neurospora crassa*. Eukaryotic Cell 11, 482 (2012).

E. Young, S. M. Lee, H. Alper, Optimizing pentose utilization in yeast: the need for novel tools and approaches. Biotechnology for Biofuels 3, 24 (2010).

A. Matsushika, H. Inoue, T. Kodaki, S. Sawayama, Ethanol production from xylose in engineered *Saccharomyces cerevisiae* strains: current state and perspectives. Applied Microbiology and Biotechnology 84, 37 (2009).

T. Fujii et al., Ethanol production from xylo-oligosaccharides by xylose-fermenting *Saccharomyces cerevisiae* expressing beta-xylosidase. Bioscience, Biotechnology, and Biochemistry 75, 1140 (2011).

K. McCluskey, The Fungal Genetics Stock Center: from molds to molecules. Advances in Applied Microbiology 52, 245 (2003).

S. Harju, H. Fedosyuk, K. R. Peterson, Rapid isolation of yeast genomic DNA: Bust n' Grab. BMC Biotechnol 4, 8 (2004).

Latimer, Luke N, Michael E Lee, Daniel Medina-Cleghorn, Rebecca A Kohnz, Daniel K Nomura, and John E Dueber. 2014. "Employing a Combinatorial Expression Approach to Characterize Xylose Utilization in *Saccharomyces cerevisiae*." Metabolic Engineering 25 (September): 20-29. doi: 10.1016/j.ymben.2014.06.002.

R. S. Sikorski, P. Hieter, A system of shuttle vectors and yeast host strains designed for efficient manipulation of DNA in *Saccharomyces cerevisiae*. Genetics 122, 19 (1989).

C. P. Kurtzman, Molecular taxonomy of the yeasts. Yeast 10, 1727 (1994).

Kim et al., Rational and evolutionary engineering approaches uncover a small set of genetic changes efficient for rapid xylose fermentation in *Saccharomyces cerevisiae*. PloS One 8, e57048 (2013).

Lin, Yuping, Kulika Chomvong, Ligia Acosta-Sampson, Raíssa Estrela, Jonathan M Galazka, Soo Rin Kim, Yong-Su Jin, and Jamie H D Cate. 2014. "Leveraging Transcription Factors to Speed Cellobiose Fermentation by *Saccharomyces cerevisiae*." Biotechnol Biofuels 7 (1): 126. doi:10.1186/s13068-014-0126-6.

O. Akpinar, K. Erdogan, S. Bostanci, Production of xylooligosaccharides by controlled acid hydrolysis of lignocellulosic materials. *Carbohydr Res* 344, 660 (2009).

S. F. Altschul et al., Gapped BLAST and PSI-BLAST: a new generation of protein database search programs. *Nucleic Acids Research* 25, 3389 (1997).

R. C. Edgar, MUSCLE: multiple sequence alignment with high accuracy and high throughput. *Nucleic Acids Research* 32, 1792 (2004).

K. Tamura, G. Stecher, D. Peterson, A. Filipski, S. Kumar, MEGA6: Molecular Evolutionary Genetics Analysis version 6.0. *Molecular Biology and Evolution* 30, 2725 (2013).

L. A. Kelley, M. J. Sternberg, Protein structure prediction on the Web: a case study using the Phyre server. *Nature Protocols* 4, 363 (2009).

K. L. Kavanagh, M. Klimacek, B. Nidetzky, D. K. Wilson, The structure of apo and holo forms of xylose reductase, a dimeric aldo-keto reductase from *Candida tenuis*. Biochemistry 41, 8785-8795 (2002).

R. Kratzer, S. Leitgeb, D. K. Wilson, B. Nidetzky, Probing the substrate binding site of *Candida tenuis* xylose reductase (AKR2B5) with site-directed mutagenesis. The Biochemical journal 393, 51-58 (2006).

O. Trott, A. J. Olson, AutoDock Vina: improving the speed and accuracy of docking with a new scoring function, efficient optimization, and multithreading. Journal of computational chemistry 31, 455-461 (2010).

Agbor, V B, N Cicek, R Sparling, A Berlin, and D B Levin. 2011. "Biomass Pretreatment: Fundamentals Toward Application." *Biotechnol Adv* 29 (6): 675-85. doi: 10.1016/j.biotechadv.2011.05.005.

Barski, Oleg A, Srinivas M Tipparaju, and Aruni Bhatnagar. 2008. "The Aldo-Keto Reductase Superfamily and Its Role in Drug Metabolism and Detoxification." *Drug Metabolism Reviews* 40 (4): 553-624. doi:10.1080/03602530802431439.

Bellissimi, Eleonora, Johannes P van Dijken, Jack T Fronk, and Antonius J A van Maris. 2009. "Effects of Acetic Acid on the Kinetics of Xylose Fermentation by an Engineered, Xylose-Isomerase-Based *Saccharomyces cerevisiae* Strain." *FEMS Yeast Research* 9 (3): 358-64. doi:10.1111/j.1567-1364.2009.00487.x.

Cai, Pengli, Ruimeng Gu, Bang Wang, Jingen Li, Li Wan, Chaoguang Tian, and Yanhe Ma. 2014. "Evidence of a Critical Role for Cellodextrin Transporte 2 (CDT-2) in Both Cellulose and Hemicellulose Degradation and Utilization in *Neurospora crassa*." Edited by Michael Freitag. *PloS One* 9 (2): e89330. doi:10.1371/journal.pone.0089330.

Colot, Hildur V, Gyungsoon Park, Gloria E Turner, Carol Ringelberg, Christopher M Crew, Liubov Litvinkova, Richard L Weiss, Katherine A Borkovich, and Jay C Dunlap. 2006. "A High-Throughput Gene Knockout Procedure for *Neurospora* Reveals Functions for Multiple Transcription Factors." *Proceedings of the National Academy of Sciences of the United States of America* 103 (27): 10352-57. doi:10.1073/pnas.0601456103.

Coradetti, Samuel T, James P Craig, Yi Xiong, Teresa Shock, Chaoguang Tian, and N Louise Glass. 2012. "Conserved and Essential Transcription Factors for Cellulase Gene Expression in Ascomycete Fungi." *Proceedings of the National Academy of Sciences of the United States of America* 109 (19): 7397-7402. doi:10.1073/pnas.1200785109.

Evangelina Vallejos, Maria, Marcia Dib Zambon, Maria Cristina Area, and Antonio Aprigio da Silva Curvelo. 2012. "Low Liquid-Solid Ratio (LSR) Hot Water Pretreatment of Sugarcane Bagasse." *Green Chemistry* 14 (7): 1982-89. doi:10.1039/c2gc35397k.

Galagan, James E, Matthew R Henn, Li-Jun Ma, Christina A Cuomo, and Bruce Birren. 2005. "Genomics of the Fungal Kingdom: Insights Into Eukaryotic Biology." *Genome Research* 15 (12): 1620-31. doi:10.1101/gr.3767105.

Hamacher, Tanja, Jessica Becker, Mark Gardonyi, Barbel Hahn-Hagerdal, and Eckhard Boles. 2002. "Characterization of the Xylose-Transporting Properties of Yeast Hexose Transporters and Their Influence on Xylose Utilization." *Microbiology (Reading, England)* 148 (Pt 9): 2783-88.

Hedges, S Blair, Joel Dudley, and Sudhir Kumar 2006. "TimeTree: a Public Knowledge-Base of Divergence Times Among Organisms." *Bioinformatics (Oxford, England)* 22 (23): 2971-72. doi:10.1093/bioinformatics/bt1505.

Hendriks, A T, and G Zeeman 2009. "Pretreatments to Enhance the Digestibility of Lignocellulosic Biomass." *Bioresour Technol* 100 (1): 10-18. doi:10.1016/j.biortech.2008.05.027.

Karhumaa, Kaisa, Rosa Garcia Sanchez, Barbel Hahn-Hägerdal, and Marie-F Gorwa-Grauslund. 2007. "Comparison of the Xylose Reductase-Xylitol Dehydrogenase and the Xylose Isomerase Pathways for Xylose Fermentation by Recombinant *Saccharomyces cerevisiae*." *Microbial Cell Factories* 6 (1): 5. doi:10.1186/1475-2859-6-5.

Lee, Sun-Mi, Taylor Jellison, and Hal S Alper. 2014. "Systematic and Evolutionary Engineering of a Xylose Isomerase-Based Pathway in *Saccharomyces cerevisiae* for Efficient Conversion Yields." *Biotechnol Biofuels* 7 (1): 122. doi:10.1186/s13068-014-0122-x.

McCluskey, K, A Wiest, and M Plamann. 2010. "The Fungal Genetics Stock Center: a Repository for 50 Years of Fungal Genetics Research." *Journal of Biosciences* 35 (1): 119-26.

Penttila, M, H Nevalainen, M Rättö, E Salminen, and J Knowles. 1987. "A Versatile Transformation System for the Cellulolytic Filamentous Fungus *Trichoderma reesei*." Gene 61 (2): 155-64.

Rabinowitz, Joshua D, and Elizabeth Kimball. 2007. "Acidic Acetonitrile for Cellular Metabolome Extraction From *Escherichia coli*." *Analytical Chemistry* 79 (16): 6167-73. doi:10.1021/ac070470c.

van Maris, Antonius J A, Aaron A Winkler, Marko Kuyper, Wim T A M de Laat, Johannes P van Dijken, and Jack T Pronk. 2007. "Development of Efficient Xylose Fermentation in *Saccharomyces cerevisiae*: Xylose Isomerase as a Key Component." *Advances in Biochemical Engineering/Biotechnology* 108 (Chapter 57). Berlin, Heidelberg: Springer Berlin Heidelberg: 179-204. doi:10.1007/10_2007_057.

Vogel, Henry J. 1956. "A Convenient Growth Medium for *Neurospora* (Medium N)." *Microbial Genetics Bulletin* 13: 42-43.

Wei, Na, Josh Quarterman, Soo Rin Kim, Jamie H D Cate, and Yong-Su Jin. 2013. "Enhanced Biofuel Production Through Coupled Acetic Acid and Xylose Consumption by Engineered Yeast." *Nature Communications* 4 (October). doi:10.1038/ncomms3580.

Wellman, Charles H, Peter L Osterloff, and Uzma Mohiuddin. 2003. "Fragments of the Earliest Land Plants." *Nature* 425 (6955): 282-85. doi:10.1038/nature01884.

Xiong, Yi, Samuel T Coradetti, Xin Li, Marina A Gritsenko, Therese Clauss, Vlad Petyuk, David Camp, et al. 2014. "The Proteome and Phosphoproteome of *Neurospora crassa* in Response to Cellulose, Sucrose and Carbon Starvation." *Fungal Genetics and Biology: FG & B* 72 (November): 21-33. doi:10.1016/j.fgb.2014.05.005.

Youk, Hyun, and Alexander van Oudenaarden. 2009. "Growth Landscape Formed by Perception and Import of Glucose in Yeast." *Nature* 462 (7275): 875-79. doi:10.1038/nature08653.

Zhou, Hang, Jing-Sheng Cheng, Benjamin L Wang, Gerald R Fink, and Gregory Stephanopoulos. 2012. "Xylose Isomerase Overexpression Along with Engineering of the Pentose Phosphate Pathway and Evolutionary Engineering Enable Rapid Xylose Utilization and Ethanol Production by *Saccharomyces cerevisiae*." *Metabolic Engineering* 14 (6): 611-22. doi:10.1016/j.ymben.2012.07.011.

What is claimed is:

1. A method of producing a xylosyl-xylitol oligomer, the method comprising:
   a) providing a microbial host cell transformed with
      a polynucleotide encoding a recombinant xylodextrin transporter polypeptide, and
      a polynucleotide encoding a recombinant xylose reductase polypeptide, wherein the xylose reductase polypeptide has xylodextrin reductase activity, which catalyzes the conversion of xylodextrin substrates to xylosyl-xylitol oligomers;
   b) culturing the host cell in a culture medium comprising xylodextrins, wherein the xylodextrin transporter polypeptide transports the xylodextrins into the host cell, and the host cell produces a xylosyl-xylitol oligomer from the xylodextrins; and
   c) purifying the xylosyl-xylitol oligomer from the culture medium.

2. The method of claim 1, wherein the host cell is a fungal host cell.

3. The method of claim 2, wherein the host cell is *Saccharomyces cerevisiae*.

4. The method of claim 1, wherein the recombinant xylodextrin transporter polypeptide comprises an amino acid sequence having at least 90% amino acid sequence identity to the amino acid sequence of SEQ ID NO: 1.

5. The method of claim 1, wherein the recombinant xylose reductase polypeptide comprises an amino acid sequence having at least 90% amino acid sequence identity to the amino acid sequence of SEQ ID NO: 2.

6. The method of claim 1, wherein one or more of the xylodextrins is xylobiose or xylotriose.

7. The method of claim 1, wherein at least one xylosyl-xylitol oligomer is xylosyl-xylitol or xylosyl-xylosyl-xylitol.

8. The method of claim 1, wherein one or more genes encoding a β-xylosidase polypeptide having xylosyl-xylitol hydrolase activity is inactivated or deleted in the chromosome of the host cell.

9. The method of claim 8, wherein the inactivation of the one or more genes encoding the β-xylosidase polypeptide is due to a mutation.

10. The method of claim 1, wherein one or more genes encoding a xylitol dehydrogenase polypeptide is inactivated or deleted in the chromosome of the host cell.

11. The method of claim 1, wherein the xylosyl-xylitol oligomer is purified by column chromatography.

12. A method of producing a xylosyl-xylitol oligomer, the method comprising:
  a) providing a microbial host cell comprising
    a xylodextrin transporter polypeptide, and
    a xylose reductase polypeptide, wherein the xylose reductase polypeptide has xylodextrin reductase activity, which catalyzes the conversion of xylodextrin substrates to xylosyl-xylitol oligomers,
    wherein one or more genes encoding a β-xylosidase polypeptide having xylosyl-xylitol hydrolase activity is inactivated or deleted in the chromosome of the host cell;
  b) culturing the host cell in a culture medium comprising xylodextrins, wherein the xylodextrin transporter polypeptide transports the xylodextrins into the host cell, and the host cell produces a xylosyl-xylitol oligomer from the xylodextrins; and
  c) purifying the xylosyl-xylitol oligomer from the culture medium.

13. The method of claim 12, wherein the host cell is a fungal host cell.

14. The method of claim 12, wherein the host cell is *Neurospora crassa*.

15. The method of claim 12, wherein the inactivation of the one or more genes encoding the β-xylosidase polypeptide is due to a mutation.

16. The method of claim 12, wherein one or more genes encoding a xylitol dehydrogenase polypeptide is inactivated or deleted in the chromosome of the host cell.

17. The method of claim 12, wherein one or more of the xylodextrins is xylobiose or xylotriose.

18. The method of claim 12, wherein at least one xylosyl-xylitol oligomer is xylosyl-xylitol or xylosyl-xylosyl-xylitol.

19. The method of claim 12, wherein the xylosyl-xylitol oligomer is purified by column chromatography.

* * * * *